US006194151B1

(12) United States Patent
Busfield

(10) Patent No.: US 6,194,151 B1
(45) Date of Patent: Feb. 27, 2001

(54) MOLECULES OF THE TNF RECEPTOR SUPERFAMILY AND USES THEREFOR

(75) Inventor: Samantha J. Busfield, Cambridge, MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/042,785

(22) Filed: Mar. 17, 1998

Related U.S. Application Data

(63) Continuation-in-part of application No. 08/938,896, filed on Sep. 26, 1997.

(51) Int. Cl.[7] ..................................................... C12P 21/02

(52) U.S. Cl. ............................ 435/6; 435/69.1; 435/325; 435/252.3; 435/320.1; 536/23.1; 536/23.5

(58) Field of Search ................................ 536/23.1, 23.5; 435/320.1, 325, 252.3, 69.1, 7.1, 6; 530/324, 325, 326, 387.1; 514/12, 13, 14

(56) References Cited

FOREIGN PATENT DOCUMENTS 0 869 179 A1 10/1998 (EP) .
98/56892 12/1998 (WO) .
99/11790 3/1999 (WO) .

OTHER PUBLICATIONS

Birkenmeier et al., "Complex patterns of sequence variation and multiple 5' and 3' ends are found among transcripts of the erythroid ankyrin gene," *Journal of Biological Chemistry,* 268(13):9533–9540 (May 1993).

Genbank® Accession No. M60847 for Mouse lipoprotein lipase (LPL) gene, exon 10.

Genbank® Accession No. X54209 for cloning vector pRSET6d (pBluescript KS plus derivative).

Genbank® Accession No. X69065, for M. musculus Ank–1 mRNA for erythroid ankyrin.

Lewis et al., "Cloning and expression of cDNAs for two distinct murine tumor necrosis factor receptors demonstrate one receptor is species specific," *Proc. Natl. Acad. Sci. USA.,* 88:2830–2834 (Apr. 1991).

Schoepfer et al., "The pRSET family of T7 promoter expression vectors for escherichia coli," *Gene,* 124:83–85 (1993).

Shalaby et al., "Binding and regulation of cellular functions by monoclonal antibodies against human tumor necrosis factor receptors," (Abstract 170065U), *Chemical Abstracts*, 113(19):534 (Nov. 1990).

Wallace et al., "Oligonucleotide probes for the screening of recombinant DNA libraries," *Methods in Enzymology,* 152:432–442 (1987).

Zechner et al., "The structure of the mouse lipoprotein lipase gene: A B1 repetitive element is inserted into the 3' untranslated region of the mRNA," *Genomics,* 11(1):62–76 (Sep. 1991).

Adams, M.D., et al. "Initial Assessment of Human Gene Diversity and Expression Patterns Based Upon 83 Million Nucleotides of cDNA Sequence" *Nature* 377 (6547 Suppl.):3–174 (1995).

Beltinger, C.P., et al. "Physical Mapping and Genomic Structure of the Human TNFR2 Gene" *Genomics* 35(1):94–100 (1996).

Dembic, A. et al., "Two Human TNF Receptors Have Similar Extracellular, But Distinct Intracellular, Domain Sequences" *Cytokine* 2(4):231–237 (1990).

Engelmann, H. et al., "Two Tumor Necrosis Factor–binding Proteins Purified from Human Urine" *J. Biol. Chem.* 265(3):1531–1536 (1990).

Gabay, C. et al. "Circulating Levels of Tumor Necrosis Factor Soluble Receptors in Systemic Lupus Erythematosus are Significantly Higher Than in Other Rheumatic Diseases and Correlated with Disease Activity" *J. Rheumatol.* 24:303–308 (1997).

GenBank® Accession No. 135962 for Tumor Necrosis Factor Receptor 2 Precursor (Tumor Necrosis Factor Binding Protein 2).

GenBank® Accession No. 2072181 for Rat osteoprotegerin (OPG) protein.

GenBank® Accession No. 207183 for Mouse osteoprotegerin (OPG) protein.

GenBank® Accession No. 207185 for Human osteoprotegerin (OPG) protein.

GenBank® Accession No. 235649 for tumor necrosis factor receptor, TNF receptor=75–kda.

GenBank® Accession No. AA072902 for Stratagene mouse macrophage (#937306) Mus musculus cDNA clone 533995 5'.

GenBank® Accession No. AA181032 for Stratagene endothelial cell 937223 Homo sapiens cDNA clone 625115 3'.

GenBank® Accession No. AA239755 for GuayWoodford Beier mouse kidney day 0 Mus musculus cDNA clone 656082 5'.

GenBank® Accession No. AA271351 for Soares mouse NML Mus musculus cDNA clone 738231 5'.

GenBank® Accession No. AA351536 for Infant brain Homo sapiens cDNA.

GenBank® Accession No. AA357231 for LNCAP cells I Homo sapiens cDNA.

(List continued on next page.)

*Primary Examiner*—James Martinell
(74) *Attorney, Agent, or Firm*—Lahive & Cockfield, LLP; DeAnn F. Smith; Debra J. Milasincic

(57) ABSTRACT

Novel TRL polypeptides, proteins, and nucleic acid molecules are disclosed. In addition to isolated, full-length TRL proteins, the invention further provides isolated TRL fusion proteins, antigenic peptides and anti-TRL antibodies. The invention also provides TRL nucleic acid molecules, recombinant expression vectors containing a nucleic acid molecule of the invention, host cells into which the expression vectors have been introduced and non-human transgenic animals in which a TRL gene has been introduced or disrupted. Diagnostic, screening and therapeutic methods utilizing compositions of the invention are also provided.

31 Claims, 22 Drawing Sheets

OTHER PUBLICATIONS

GenBank® Accession No. AA374471 for HSC172 cells I Homo sapiens cDNA.

GenBank® Accession No. AA554244 for NCI_CGAP_Co3 Homo sapiens cDNA clone IMAGE:1029164 3'.

GenBank® Accession No. AA555059 for NCI_CGAP_–Coll Homo sapiens cDNA clone IMAGE:1015210 3'.

GenBank® Accession No. AA621819 for NCI_CGAP_Co10 Homo sapiens cDNA clone IMAGE:1144858 3', mRNA sequence.

GenBank® Accession No. D59902 for Human fetal brain cDNA 5'–end GEN–073E08.

GenBank® Accession No. N49208 for Soares_multiple_sclerosis_2NbHMSP Homo sapiens cDNA clone 280262 3'.

GenBank® Accession No. N50261 for Soares_multiple_sclerosis_2NbHMSP Homo sapiens cDNA clone 280262 5'.

GenBank® Accession No. R74815 for Mouse brain, Stratagene Mus musculus cDNA 3' end.

Gruss, H–J. and S.K. Dower, "Tumor Necrosis Factor Ligand Superfamily: Involvement in the Pathology of Malignant Lymphomas" *Blood* 85(12):3378–3404 (1995).

Heller, R.A. et al., "Complementary DNA Cloning of a Receptor for Tumor Necrosis Factor and Demonstration of a Shed Form of the Receptor" *Proc. Natl. Acad. Sci. USA* 87(16):6151–6155 (1990).

Itoh, N. and S. Nagata, "A Novel Protein Domain Required for Apoptosis" *The Journal of Biochemistry* 268(15):10932–10937 (1993).

Kohno, T. et al., "A Second Tumor Necrosis Factor Receptor Gene Product Can Shed a Naturally Occurring Tumor Necrosis Factor Inhibitor" *Proc. Natl. Acad. Sci. USA* 87(21):8331–8335 (1990).

Loetscher, H. et al., "Purification and Partial Amino Acid Sequence Analysis of Two Distinct Tumor Necrosis Factor Receptors from HL60 Cells" *J. Biol. Chem.* 265(33):20131–20138 (1990).

Naismith, J.A. and S.R. Sprang, "Tumor Necrosis Factor Receptor Superfamily" *J. Inflamm.* 47:1–7 (1996).

Pennica, D. et al., "Biochemical Properties of the 75–kDa Tumor Necrosis Factor Receptor: Characterization of the Ligand Binding, Internalization, and Receptor Phosphorylation" *The Journal of Biological Chemistry* 267(29):21172–21178 (1992.

Reddi, A.H., "Bone Morphogenesis and Modeling: Soluble Signals Sculpt Osteosomes in the Solid State" *Cell* 89:159–161 (1997).

Simonet, W.E. et al., "Osteoprotegerin: A Novel Secreted Protein Involved in the Regulation of Bone Density" *Cell* 89(2):309–319 (1997).

Smith, C.A. et al., "A Receptor for Tumor Necrosis Factor Defines an Unusual Family of Cellular and Viral Proteins" *Science* 248(4958):1019–1022 (1990).

Tartaglia, L.A. et al., "A Novel Domain within the 55 kd TNF Receptor Signals Cell Death" *Cell* 74:845–853 (1993).

```
GTCGACCCACGGTCCGGGAGACTTACCACCAAGTAGCAGGATCTTCTCTTTCTCAATTTCCAATATGAAATTAAATTTC  79

CCAACAAGAAAACCAACCACTATCCATCGCCAACCACCTCTGCCCCTACTTTCAGACTCAGAAGGAAGAAAACTAAGTA  158

TATCGTAAACTCTAAGGAGGAAACCTCAAGAACCGCTTGGATTCCTCAGCACCATCACAGCTCAACCAGAACAAAAGAC  237

TCTGAGTCTCCCTGGCACCTACCGCCATGTTGACCGTACCACTGGCCAGGTGCTAACCTGCGACAAGTGCCCAGCAGGA  316

                             M   S   L   R   V   C   S   S   C   P   A   G   T    13
ACGTATGTCTCCGAGCACTGTACCAAC ATG AGC CTG CGA GTC TGC AGC AGC TGC CCC GCG GGG ACC  382

 F   T   R   H   E   N   G   I   E   R   C   H   D   C   S   Q   P   C   P   W    33
TTT ACC AGG CAC GAG AAC GGC ATA GAG AGA TGC CAT GAC TGT AGT CAG CCA TGT CCA TGG  442

 P   M   I   E   R   L   P   C   A   A   L   T   D   R   E   C   I   C   P   P    53
CCG ATG ATT GAG AGA TTA CCT TGT GCT GCC TTG ACT GAC CGA GAG TGC ATC TGC CCA CCT  502

 G   M   Y   Q   S   N   G   T   C   A   P   H   T   V   C   P   V   G   W   G    73
GGA ATG TAT CAG TCT AAT GGT ACC TGC GCT CCC CAT ACA GTG TGC CCC GTG GGC TGG GGT  562

 V   R   K   K   G   T   E   N   E   D   V   R   C   K   Q   C   A   R   G   T    93
GTG CGG AAG AAA GGG ACA GAG AAT GAA GAT GTG CGC TGT AAG CAG TGC GCT CGG GGT ACC  622

 F   S   D   V   P   S   S   V   M   K   C   K   A   H   T   D   C   L   G   Q   113
TTC TCT GAC GTG CCT TCC AGT GTG ATG AAG TGT AAA GCT CAC ACG GAC TGT CTG GGT CAG  682

 N   L   E   V   V   K   P   G   T   K   E   T   D   N   V   C   G   M   R   L   133
AAC CTG GAG GTG GTC AAG CCA GGG ACC AAG GAG ACA GAC AAC GTC TGT GGC ATG CGC CTG  742

 F   F   S   S   T   N   P   P   S   S   G   T   V   T   F   S   H   P   E   H   153
TTC TTC TCC AGC ACA AAC CCA CCT TCC TCT GGC ACA GTT ACC TTT TCT CAC CCT GAG CAT  802
```

FIG.1A

```
 M   E   S   H   D   V   P   S   S   T   Y   E   P   Q   G   M   N   S   T   D    173
ATG GAA TCC CAC GAT GTC CCT TCC TCC ACC TAT GAG CCC CAA GGC ATG AAC TCA ACA GAT   862

 S   N   S   T   A   S   V   R   T   K   V   P   S   G   I   E   E   G   T   V    193
TCC AAC TCT ACT GCC TCT GTT AGA ACT AAG GTA CCA AGT GGC ATC GAG GAA GGG ACA GTG   922

 P   D   N   T   S   S   T   S   G   K   E   G   T   N   R   T   L   P   N   P    213
CCT GAC AAT ACG AGC TCA ACC AGT GGG AAG GAA GGC ACT AAT AGG ACC CTG CCA AAC CCA   982

 P   Q   V   T   H   Q   Q   A   P   H   H   R   H   I   L   K   L   L   P   S    233
CCA CAA GTT ACC CAC CAG CAA GCC CCC CAC CAC AGA CAC ATT CTG AAG CTG CTG CCA TCG  1042

 S   M   E   A   T   G   E   K   S   S   T   A   I   K   A   P   K   R   G   H    253
TCC ATG GAG GCC ACG GGT GAG AAG TCC AGC ACA GCC ATC AAG GCC CCC AAG AGG GGT CAC  1102

 P   R   Q   N   A   H   K   H   F   D   I   N   E   H   L   P   W   M   I   V    273
CCC AGA CAG AAC GCT CAC AAG CAT TTC GAC ATC AAC GAG CAC TTG CCT TGG ATG ATC GTC  1162

 L   F   L   L   L   V   L   V   L   I   V   V   C   S   I   R   K   S   S   R    293
CTC TTC CTT CTG CTG GTC CTG GTG CTG ATA GTG GTG TGC AGT ATC CGA AAG AGC TCC AGG  1222

 T   L   K   K   G   P   R   Q   D   P   S   A   I   V   E   K   A   G   L   K    313
ACT CTC AAA AAG GGG CCC CGG CAG GAT CCC AGC GCC ATA GTG GAA AAG GCG GGG CTG AAG  1282

 K   S   L   T   P   T   Q   N   R   E   K   W   I   Y   Y   R   N   G   H   G    333
AAG TCC CTG ACT CCC ACC CAG AAC CGG GAG AAA TGG ATC TAC TAC CGC AAC GGC CAT GGT  1342

 I   D   I   L   K   L   V   A   A   Q   V   G   S   Q   W   K   D   I   Y   Q    353
ATT GAC ATC TTG AAG CTT GTA GCA GCC CAG GTG GGA AGC CAG TGG AAG GAC ATC TAT CAG  1402
```

FIG.1B

```
 F   L   C   N   A   S   E   R   E   V   A   A   F   S   N   G   Y   T   A   D    373
TTT CTT TGC AAC GCC AGT GAG AGG GAG GTG GCG GCC TTC TCC AAT GGA TAC ACT GCA GAT  1462

 H   E   R   A   Y   A   A   L   Q   H   W   T   I   R   G   P   E   A   S   L    393
CAT GAA CGG GCC TAC GCG GCT CTG CAG CAC TGG ACC ATC CGT GGC CCT GAG GCC AGC CTT  1522

 A   Q   L   I   S   A   L   R   Q   H   R   R   N   D   V   V   E   K   I   R    413
GCC CAG CTC ATT AGC GCC TTG CGC CAG CAC CGA CGC AAT GAT GTT GTG GAG AAG ATT CGT  1582

 G   L   M   E   D   T   T   Q   L   E   T   D   K   L   A   L   P   M   S   P    433
GGG CTG ATG GAA GAC ACC ACG CAG TTG GAA ACA GAC AAA CTG GCT CTC CCC ATG AGC CCC  1642

 S   P   L   S   P   S   P   I   P   S   P   N   V   K   L   E   N   S   T   L    453
AGT CCG CTG AGC CCG AGC CCC ATC CCC AGT CCT AAC GTG AAA CTT GAG AAT TCC ACT CTC  1702

 L   T   V   E   P   S   P   L   D   K   N   K   C   F   F   V   D   E   S   E    473
CTG ACA GTG GAG CCC TCA CCG CTG GAC AAG AAC AAG TGC TTC TTC GTG GAC GAG TCA GAG  1762

 P   L   L   R   C   D   S   T   S   S   G   S   S   A   L   S   R   N   G   S    493
CCC CTT CTG CGT TGC GAC TCC ACA TCC AGT GGC TCT TCA GCA CTG AGC AGA AAC GGC TCC  1822

 F   I   T   K   E   K   K   D   T   V   L   R   Q   V   R   L   D   P   C   D    513
TTT ATT ACC AAA GAA AAG AAG GAC ACA GTG TTG CGG CAG GTC CGC CTG GAC CCC TGT GAC  1882

 L   Q   P   I   F   D   D   M   L   H   I   L   N   P   E   E   L   R   V   I    533
TTG CAG CCC ATC TTT GAT GAC ATG CTG CAT ATC CTG AAC CCC GAG GAG CTG CGG GTG ATT  1942

 E   E   I   P   Q   A   E   D   K   L   D   R   L   F   E   I   I   G   V   K    553
GAA GAG ATT CCC CAG GCT GAG GAC AAA CTG GAC CGC CTC TTC GAG ATC ATT GGG GTC AAG  2002
```

FIG.1C

```
 S   Q   E   A   S   Q   T   L   L   D   S   V   Y   S   H   L   P   D   L   L    573
AGC CAA GAA GCC AGC CAG ACC CTC TTG GAC TCT GTG TAC AGT CAT CTT CCT GAC CTA TTG  2062

 *                                                                                574
TAG                                                                              2065

AACACAGGGGCACTGCATTCTGGGAATCAACCTACTGGCGGGGTGATTTCATTTCGTTTCTGACTTTTGTGTTTTGGTG  2144

TGTATGTATGTGTTTAACAGAGTGTATGGCCGGTGAGTTTGGGGTTCTTTCTTTCTTTCTTTCTTTCTTTCTTTCTTTC  2223

TTTCTTTCTTTCTTCCTTCCTTCCTTCCTTCCTTCCTTCCTTCCTTCCTTCCTTCCTGAAAGTGAATGTATAAAGCCTT  2302

TACAATGTATAACTGTTGGAAAATGCCCACCACTAAATTTTTTTTAAGTTCCATATATTCTCCATTTTTGCCTTCTTAT  2381

ATATATCTTCAACACTATTCTGTGCACTTTAAAAACTTAACATAAACGCAGTGTGACTTCTCCCATATGCTGGGTTCCG  2460

AGACTCTCAACTTCTTAAAAACCTAATGGCATCTTGTGACTCCTAGAAGTAGACATAAGTCTTTCAACCTTCACACCTA  2539

CTCTTTCTGTTTTAATTATTATTGCTATTTGTCTTATTGTTTGTGCTTTACAAGCGTTCTTGAGGACGGAGGGAATCTA  2618

CGACCCTGTTGATGACTGTAACTCTATTCGACTTTGAGTTGTCTTCTTCATGTCTTGTTATATAGTTCATATTCATGGC  2697

TGAAACTTGACCATACTCCCTAGCGCCGCTGATTGTATGGTTTTCGTCTGGACACCGTACACTGCCTGATAACTTGTGC  2776

ACCTCTTAACGCTACTATGCTCTGGGCTGGAGAATGAAATCTTTAAGTCACCAGGACTTGCTGTTTCAGTGGCTTGACA  2855

CCTGGGCCACCAAAGAACTCGATCTTCATCTTTTAGGGACACCTCTGCTGCACCTTGGAAAGCCAACCTTAAGTGCCAG  2934

TGGCACTTTATGCCCAGCTTTGCTTTGAAAGATATCTTTCTTGTTTTTTTTTATCCTTCTCTTTCTCTCTTTTTTTTAA  3013
```

FIG.1D

AAATACACATAGTCAATAGGTCCAGTCTGCCCTCAAGGCCTTGCTGGGTTTTTTCGTCATCCAATCACTTTCATTAAA 3092

AATGGCTGCAGCTGTAAGAACTCTTGTCTGATAAATTTTCAACTATGCTCTCATTTATCTACCTGCCCTCTGATGCTCA 3171

GTCGTCAGACTCTAATGCAAAGGTGGACGTCGGCTGCCTTTGCGTGGGCGGGCTTAGTGGTGAGGAACTGATATCAGAA 3250

AAAAATGCCTTCAAGTATACTAATTTATTAATAAATATTAGGTGTTTGTTAAAAAAAAAAAAAAAAAAAAAAAAAGCGG 3329

```
GCTCAGCGCCCCTAGACCCTCCCTTGCCGCCTCCCTCCTCTGCCCGGCCGTACCAGTGCACATGGGGTGTTGGAGGTAG  79

ATGGGCTCCCGGCCCGGGAGGCGGCGGTGGATGCGGCGCTGGGCAGAAGCAGCCGCCGATTCCAGCTGCCCCGCGCGCC 158

                                  M   G   T   S   P   S   S   S   T   A   L   A   12
CCGGGCGCCCCTGCGAGTCCCCGGTTCAGCC ATG GGG ACC TCT CCG AGC AGC AGC ACC GCC CTC GCC  225

 S   C   S   R   I   A   R   R   A   T   A   T   M   I   A   G   S   L   L   L   32
TCC TGC AGC CGC ATC GCC CGC CGA GCC ACA GCC ACG ATG ATC GCG GGC TCC CTT CTC CTG  285

 L   G   F   L   S   T   T   T   A   Q   P   E   Q   K   A   S   N   L   I   G   52
CTT GGA TTC CTT AGC ACC ACC ACA GCT CAG CCA GAA CAG AAG GCC TCG AAT CTC ATT GGC  345

 T   Y   R   H   V   D   R   A   T   G   Q   V   L   T   C   D   K   C   P   A   72
ACA TAC CGC CAT GTT GAC CGT GCC ACC GGC CAG GTG CTA ACC TGT GAC AAG TGT CCA GCA  405

 G   T   Y   V   S   E   H   C   T   N   T   S   L   R   V   C   S   S   C   P   92
GGA ACC TAT GTC TCT GAG CAT TGT ACC AAC ACA AGC CTG CGC GTC TGC AGC AGT TGC CCT  465

 V   G   T   F   T   R   H   E   N   G   I   E   K   C   H   D   C   S   Q   P  112
GTG GGG ACC TTT ACC AGG CAT GAG AAT GGC ATA GAG AAA TGC CAT GAC TGT AGT CAG CCA  525

 C   P   W   P   M   I   E   K   L   P   C   A   A   L   T   D   R   E   C   T  132
TGC CCA TGG CCA ATG ATT GAG AAA TTA CCT TGT GCT GCC TTG ACT GAC CGA GAA TGC ACT  585

 C   P   P   G   M   F   Q   S   N   A   T   C   A   P   H   T   V   C   P   V  152
TGC CCA CCT GGC ATG TTC CAG TCT AAC GCT ACC TGT GCC CCC CAT ACG GTG TGT CCT GTG  645

 G   W   G   V   R   K   K   G   T   E   T   E   D   V   R   C   K   Q   C   A  172
GGT TGG GGT GTG CGG AAG AAA GGG ACA GAG ACT GAG GAT GTG CGG TGT AAG CAG TGT GCT  705
```

FIG.2A

```
 R   G   T   F   S   D   V   P   S   S   V   M   K   C   K   A   Y   T   D   C   192
CGG GGT ACC TTC TCA GAT GTG CCT TCT AGT GTG ATG AAA TGC AAA GCA TAC ACA GAC TGT  765

 L   S   Q   N   L   V   V   I   K   P   G   T   K   E   T   D   N   V   C   G   212
CTG AGT CAG AAC CTG GTG GTG ATC AAG CCG GGG ACC AAG GAG ACA GAC AAC GTC TGT GGC  825

 T   L   P   S   F   S   S   S   T   S   P   S   P   G   T   A   I   F   P   R   232
ACA CTC CCG TCC TTC TCC AGC TCC ACC TCA CCT TCC CCT GGC ACA GCC ATC TTT CCA CGC  885

 P   E   H   M   E   T   H   E   V   P   S   S   T   Y   V   P   K   D   Q   R   252
CCT GAG CAC ATG GAA ACC CAT GAA GTC CCT TCC TCC ACT TAT GTT CCC AAA GAC CAA AGG  945

 Y   *                                                                           254
TAC TGA                                                                          951

GTAGCATCCAGGAAGGGACAGTCCCTGACAACACAAGCTCAGCAAGGGGGAAGGAAGACGTGAACAAGACCCTCCCAAA  1030

CCTTCAGGTAGTCAACCACCAGCAAGGCCCCCACCACAGACACATCCTGAAGCTGCTGCCGTCCATGGAGGCCACTGGG  1109

GGCGAGAAGTCCAGCACGCCCATCAAGGGCCCCAAGAGGGGACATCCTAGACAGAACCTACACAAGCATTTTGACATCA  1188

ATGAGCATTTGCCCTGGATGATTGTGCTTTTCCTGCTGCTGGTGCTTGTGGTGATTGTGGTGTGCAGTATCCGGAAAAG  1267

CTCGAGGACTCTGAAAAAGGGGCCCCGGCAGGATCCCAGTGCCATTGTGGAAAAGGCAGGGCTGAAGAAATCCATGACT  1346

CCAACCCAGAACCGGGAGAAATGGATCTACTACTGCAATGGCCATGGTATCGATATCCTGAAGCTTGTAGCAGCCCAAG  1425

TGGGAAGCCAGTGGAAAGATATCTATCAGTTTCTTTGCAATGCCAGTGAGAGGGAGGTTGCTGCTTTCTCCAATGGGTA  1504

CACAGCCGACCACGAGCGGGCCTACGCAGCTCTGCAGCACTGGACCATCCGGGGCCCCGAGGCCAGCCTCGCCCAGCTA  1583
```

FIG.2B

```
ATTAGCGCCCTGCGCCAGCACCGGAGAAACGATGTTGTGGAGAAGATTCGTGGGCTGATGGAAGACACCACCCAGGTAA  1662
TGGAGCCCTTGTTGTGTGTCATTACCACCGACCTATTGCCCCTATGCTTCAAATTTTATCAGTTGTATGGGAACAAAGA  1741
AAAATAACATATTCGGTGGATAGGCACACACACACACACACGCATACGCCTGCACACACACACACACACCCTACCTTCT  1820
AGGACGGGGGTTCTCAGTGGCCGTCTATTAGAATCATCTAGAAAACTTTAAAAAAAAATACTGATGCTCAGACCCTACC  1899
TGCAGACCAGTCACATCAGAATCTCCAGGGGGCAGAGCGTGAATCGGTATTTGTAAAAGCTCTTTGTTACTCCATTTAC  1978
AATCCATTTTGCATGACACACTTTGAACAAAACCAAGAAAAAATACTTTTTACTACACCGCCTCTCCTCCAGAGGGTGT  2057
TTTTGTGATGTGGCTTATGAAGGCAGCATTCTTGCCTCCTGAGGATGCAGGTGGTGCTAGCGGCAGTTGATGACAGAAC  2136
TGATTCTCCTCCTTGGGTTGTTCCGTGGAGCACATCAGATGGGAACTGAGGGGACCCAGGAGTGTGATTTCTTTATAGC  2215
TAATAAGCCCTGGCTTTGGAGCCAGACAGCGCTGGATTTGAATCCTGGCTCTGGTACATATTAGCTTAGGTGATGAAGG  2294
GTAAGTTACTTCAACTTTCCTTGCCTCTGTTATTCACATTTTCAAGTCTGCTATATAAGATTAAGATGAGAAATAAAGC  2373
ATATAAAATGCCTGACTCATTGAAAGTGTTCTACAAGTGGTAGTTACGACCATGATGTAACTCATTTTACTTAGCCTTT  2452
CTTTAATTGTATGTACTTCCCTGAAAGGCCATGAATAAAGTTCAGATTTGGATATTGAATCATATTTTCCACAGACTTC  2531
AATTCAGGTTTCAGAACATATTCCCAAAGTAAAGAAAATGCTGCCACTAAGACTAGATAAAACCCACTTCAGATTGGTA  2610
AC                                                                               2612
```

FIG.2C

```
Alignment of:
Sequence          Start     End   Sequence Type

huTango75 I        (1  >   253)    PROTEIN
huTango75 II       (1  >   605)    PROTEIN
muTANGO 75         (1  >   573)    PROTEIN
huTNFR2            (1  >   461)    PROTEIN
muTNFR2            (1  >   474)    PROTEIN
TNFR2soluble       (1  >   325)    PROTEIN
huCD40R            (1  >   277)    PROTEIN
muCD40R            (1  >   289)    PROTEIN
huOPG              (1  >   401)    PROTEIN
muOPG              (1  >   401)    PROTEIN


                 1                                                          60
huTango75 I      MGTSPSSSTALASCSRIARRATATMIAGSLLLLGFLSTTTAQPEQKASNLIGTYRHVDRA
huTango75 II     MGTSPSSSTALASCSRIARRATATMIAGSLLLLGFLSTTTAQPEQKASNLIGTYRHVDRA
muTANGO 75       M-----------------------------------------------------------
HuTNFR2          MAPVAVWAALAVG---LELWAAAHALPAQVAFTPYAPEPGS-----TCRL-REYYDQT--
MuTNFR2          MAPAALWVALVFE---LQLWATGHTVPAQVVLTPYKPEPGY-----ECQISQEYYDRK--
TNFR2 soluble    MLRL---IALLVC---V-VYVYGDDVP-------YSSNQG------KCG-GHDY--EK--
huCD40R          MVRLPLQCVLW----------------GCLLTAVHPEPPTACREKQ-------YLINSQC
muCD40R          MVSLPRLCALW----------------GCLLTAVHLGQCVTCSDKQ-------YLHDGQC
huOPG            MNKL--LCCAL----------------VFLDISIKWTTQETFPPK--------YLHYDEE
muOPG            MNKW--LCCAL----------------LVLLDIIEWTTQETLPPK--------YLHYDPE
```

FIG.3A

```
                   61                                                          120
huTango75 I        TGQVLTCDKCPAGTYVSEHCTNTSLRVCSSCPVGTFTRHENGIEKCHD---CSQPCPWPM
huTango75 II       TGQVLTCDKCPAGTYVSEHCTNTSLRVCSSCPVGTFTRHENGIEKCHD---CSQPCPWPM
MuTango75 II       -----------------------SLRVCSSCPAGTFTRHENGIERCHD---CSQPCPWPM
HuTNFR2            --AQMCCSKCSPGQHAKVFCTKTSDTVCDSCEDSTYTQLWNWVPECLS---CGSRCSSDQ
MuTNFR2            --AQMCCAKCPPGQYVKHFCNKTSDTVCADCEASMYTQVWNQFRTCLS---CSSSCTTDQ
TNFR2 soluble      --DGLCCASCHPGFYASRLCGPGSNTVCSPCEDGTFTASTNHAPACVS---CRGPCTGHL
huCD40R            ------CSLCQPGQKLVSDCTEFTETECLPCGESEFLDTWNRETHCHQHKYCDPN-LGLR
muCD40R            ------CDLCQPGSRLTSHCTALEKTQCHPCDSGEFSAQWNREIRCHQHRHCEPN-QGLR
huOPG              TSHQLLCDKCPPGTYLKQHCTAKWKTVCAPCPDHYYTDSWHTSDECL---YCSPVCKELQ
muOPG              TGHQLLCDKCAPGTYLKQHCTVRRKTLCVPCPDHSYTDSWHTSDECV---YCSPVCKELQ

                   121                                                         180
huTango75 I        IEKLPCAALTDRECTCPPGMFQS----NAT---CAPHTVCPVGWGVRKKGTETEDVRCKQ
huTango75 II       IEKLPCAALTDRECTCPPGMFQS----NAT---CAPHTVCPVGWGVRKKGTETEDVRCKQ
MuTango75 II       IERLPCAALTDRECICPPGMYQS----NGT---CAPHTVCPVGWGVRKKGTENEDVRCKQ
HuTNFR2            VETQACTREQNRICTCRPGWYCALSKQEG-CRLCAPLRKCRPGFGVARPGTETSDVVCKP
MuTNFR2            VEIRACTKQQNRVCACEAGRYCALKTHSGSCRQCMRLSKCGPGFGVASSRAPNGNVLCKA
TNFR2 soluble      SESQPCDRTHDRVCNCSTGNYCLLKGQNG-CRICAPQTKCPAGYGVS-GHTRAGDTLCEK
huCD40R            -VQQKGTSETDTICTCEEGWHCT----SEACESCVLHRSCSPGFGVKQIATGVSDTICEP
muCD40R            -VKKEGTAESDTVCTCKEGQHCT----SKDCEACAQHTPCIPGFGVMEMATETTDTVCHP
huOPG              YVKQECNRTHNRVCECKEGRY-------LEIEFCLKHRSCPPGFGVVQAGTPERNTVCKR
muOPG              SVKQECNRTHNRVCECEEGRY-------LEIEFCLKHRSCPPGSGVVQAGTPERNTVCKK
```

FIG.3B

```
                   181                                                        240
huTango75 I        CARGTFSDVPSSVMKCKAYTDCLSQNLVVIKPGTKETDNVCGTLPSFSSSTSPSPGTAIF
huTango75 II       CARGTFSDVPSSVMKCKAYTDCLSQNLVVIKPGTKETDNVCGTLPSFSSSTSPSPGTAIF
MuTango75 II       CARGTFSDVPSSVMKCKAHTDCLGQNLEVVKPGTKETDNVCGMRLFFSSTNPPSSGTVTF
HuTNFR2            CAPGTFSNTTSSTDICRPHQICNVVAI----PGNASRDAVCTSTSPTRSM----------
MuTNFR2            CAPGTFSDTTSSTDVCRPHRICSILAI----PGNASTDAVCAPESPTLSA----------
TNFR2 soluble      CPPHTYSDSLSPTERCGTSFNYISVGF----NLYPVNETSCTTTAGHNEV----------
huCD40R            CPVGFFSNVSSAFEKCHPWTSCETKDLVVQQAGTNKTDVVCGP----QDRLRALVVIPII
muCD40R            CPVGFFSNQSSLFEKCYPWTSCEDKNLEVLQKGTSQTNVICGL----KSRMRALLVIPVV
huOPG              CPDGFFSNETSSKAPCRKHTNCSVFGLLLTQKGNATHDNICSG----NSESTQKCGIDVT
muOPG              CPDGFFSGETSSKAPCIKHTNCSTFGLLLIQKGNATHDNVCSG----NREATQKCGIDVT

                   241                                                        300
huTango75 I        PRPEHMETHEVPSSTYVPK-----------------------------------------
huTango75 II       PRPEHMETHEVPSSTYVPKGMNSTESNSSASVRPKVLSSIQEGTVPDNTSSARGKEDVNK
MuTango75 II       SHPEHMESHDVPSSTYEPQGMNSTDSNSTASVRTKVPSGIEEGTVPDNTSSTSGKEGTNR
HuTNFR2            ----------APGAVHLPQ------------------------------------PVSTR
MuTNFR2            ----------IPRTLYVSQ------------------------------------PEPTR
TNFR2 soluble      ----------IKTKEFTVT------------------------------------LNYTD
huCD40R            F-GILFAILLV--------------------------------------------------
muCD40R            M-GILITIFGV--------------------------------------------------
huOPG              LCEEAFFRFAVPT-----------------------------------------------
muOPG              LCEEAFFRFAVPT-----------------------------------------------
```

FIG.3C

```
                 301                                                        360
huTango75 I      ------------------------------------------------------------
huTango75 II     TLPNLQVVNHQQGPHHRHILKLLPSMEATGGEKSSTPIKGPKRGHPRQNLHKHFDINEHL
MuTango75 II     TLPNPPQVTHQQAPHHRHILKLLPSSMEATGEKSSTAIKAPKRGHPRQNAHKHFDINEHL
HuTNFR2          SQHTQPTPEPSTAPSTSFLLPMGPSPPAEGST-GDFALPV--------------GLIVGV
MuTNFR2          SQPLDQEPGPSQTPS--ILTSLGSTPIIEQSTKGGISLPI--------------GLIVGV
TNFR2 soluble    CDPV-------------FHTEYYATSGKEGA--GGFFTGT--------------DIYQNT
huCD40R          ------------------------------------------------------------
muCD40R          ------------------------------------------------------------
huOPG            --------------------KFTPN-----------------------------------
muOPG            --------------------KIIPN-----------------------------------

                 361                                                        420
huTango75 I      ------------------------------------------------------------
huTango75 II     PWMIVLFLLLVLVVIVVCSIRKSSRTLKKGPRQDPSAIVEKAGLKKSMTPTQNREKWIYY
MuTango75 II     PWMIVLFLLLVLVLIVVCSIRKSSRTLKKGPRQDPSAIVEKAGLKKSLTPTQNREKWIYY
HuTNFR2          TALGLLIIGVVNCVI-MTQVKKKPLCLQ---REAKVPHLPADKARGTQGPEQQ-------
MuTNFR2          TSLGLLMLGLVNCII-LVQRKKKPSCLQ---RDAKVPHVPDEKSQDAVGLEQQ-------
TNFR2 soluble    TKVCTLNVE-IQCSE-GDDIHT----LQ---KTNGGSTMPHSETITVVG-----------
huCD40R          ---LVF-------IKKVAKKPTNKAPHP----KQEP------------------------
muCD40R          ---FLY-------IKKVVKKPKDNEMLPPAARRQDP------------------------
huOPG            -WLSVL-------VDNLPGTKVNAESVERIKRQHSS------------------------
muOPG            -WLSVL-------VDSLPGTKVNAESVERIKRRHSS------------------------
```

FIG.3D

```
                  421                                                        480
huTango75 I       ----------------------------------------------DQRY----------
huTango75 II      CNGHGIDILKLVAAQVGSQWKDIYQFLCNASEREVAAFSNGYTADHERAYAALQHWTIRG
MuTango75 II      RNGHGIDILKLVAAQVGSQWKDIYQFLCNASEREVAAFSNGYTADHERAYAALQHWTIRG
HuTNFR2           ------------------------HLLITAPSSSSSSLESSASALD-----------RRA
MuTNFR2           ------------------------HLLTTAPSSSSSSLESSASAGD-----------RRA
TNFR2 soluble     -----------------------------------SCL--SDVNVD-----------IMY
huCD40R           ---------------------------------------------QEINFP---------
muCD40R           ---------------------------------------------QEM------------
huOPG             ---------------------------------------------QEQTFQLLKLWK---
muOPG             ---------------------------------------------QEQTFQLLKLWK---

                  481                                                        540
huTango75 I       ------------------------------------------------------------
huTango75 II      PEASLAQLISALRQHRRNDVVEKIRGLMEDTTQLETDKLALPMSPSPLSPSPIPSPNAKL
MuTango75 II      PEASLAQLISALRQHRRNDVVEKIRGLMEDTTQLETDKLALPMSPSPLSPSPIPSPNVKL
HuTNFR2           PT----------RNQPQAPGV-EASGAGE------------ARASTGSSDSSPGGHGTQV
MuTNFR2           PP----------GGHPQARVMAEAQGFQE------------ARASSRISDSSHGSHGTHV
TNFR2 soluble     SD----------TNHP-----GEVDDFVE------------YH------------WGTRL
huCD40R           ------------------------------------------------------------
muCD40R           ------------------------------------------------------------
huOPG             ------------HQNKAQDIVKKII----QDIDLCENSVQRHIGHANLTFEQL-------
muOPG             ------------HQNRDQEMVKKII----QDIDLCESSVQRHLGHSNLTTEQL-------
```

FIG.3E

```
                   541                                                        600
huTango75 I        ------------------------------------------------------------
huTango75 II       ENSALLTVEPSPQD------------LL-----------FKWLDNWATKELELHLL----
MuTango75 II       ENSTLLTVEPSPLDKNKCFFVDESEPLLRCDSTSSGSSALSRNGSFITKEKKDTVLRQVR
HuTNFR2            NVTCIVNVCSSSDHSSQCS-SQASSTMGDTDSSPSESP-----------KDEQVPFSKEE
MuTNFR2            NVTCIVNVCSSSDHSSQCS-SQASATVGDPDAKPSASP-----------KDEQVPFSQEE
TNFR2 soluble      RFFPLPKRCTP-------------------------------------------------
huCD40R            ------DDLPGSNTAAP-----VQETLHGCQPVT---Q----------EDG---------
muCD40R            ------EDYPGHNTAAP-----VQETLHGCQPVT---Q----------EDG---------
huOPG              --RSLMESLPGKKVGAE----DIEKTIKACKPSD---QILKLLSLWRIKNGDQDTLKGLM
muOPG              --LALMESLPGKKISPE----EIERTRKTCKSSE---QLLKLLSLWRIKNGDQDTLKGLM

                   601                                                        660
huTango75 I        ------------------------------------------------------------
huTango75 II       ----GFELFWNTLLHFGKS---KSSASGALSIENLPS-FALKDV---------LFFIYT-
MuTango75 II       LDPCDLQPIFDDMLHILNPEELRVIEEIPQAEDKLDRLFEIIGVKSQEASQTLLDSVYSH
HuTNFR2            CAFRSQLETPETLLGSTEEKPLPLGVPDAGMKPS--------------------------
MuTNFR2            CPSQSPCETTETL--QSHEKPLPLGVPDMGMKPSQAGWFDQIAVKVA-------------
TNFR2 soluble      ---------------------------------------------VS-------------
huCD40R            ------KESRISVQERQ-------------------------------------------
muCD40R            ------KESRISVQERQVTDSI--ALRPL-------------------------------
huOPG              ---HALKHSKTYHFPKTVTQSLKKTIRFLHSFT-MYKLYQ----------KLFLEMIGNQ
muOPG              ---YALKHLKTSHFPKTVTHSLRKTMRFLHSFT-MYRLYQ----------KLFLEMIGNQ
```

FIG.3F

```
                 661     669
huTango75 I      ---------
huTango75 II     ---------
MuTango75 II     LPDL----L
HuTNFR2          ---------
MuTNFR2          ---------
TNFR2 soluble    ---------
huCD40R          ---------
muCD40R          --------V
huOPG            VQSVKISCL
muOPG            VQSVKISCL
```

FIG.3G

```
CGGGTCACGTTTGCGGGTACCCACCCACACCCGCCGCGCTTAATGCGCCGCTACAGGGCGCGTCCCATTCGCCATTCAG    79

GCTGCGCAACTGTTGGAAGGGCGATCGGGTGCGGGCCTCTTCGCTATTACGCCAAGCTGGCGAAAGGGGGATGTGCTGC   158

AAGGCGATTAAGTTGGGTAACGCCAAGGGTTTTCCCAGTCACGACGGTTGTAAAACGACGGCCAGTGAATTGAATTTAG   237

GTGACACTATAGAAGAGCTATGACGTCGCATGCACGCGTACGTAAGCTTGGATCCTCTAGAGCGGCCGCGCCGCTGGGC   316

AGGTGCTGAGCGCCCCTAGAGCCTCCCTTGCCGCCTCCCTCCTCTGCCCGGCCGCAGCAGTGCACATGGGGTGTTGGAG   395

GTAGATGGGCTCCCGGCCCGGGAGGCGGCGGTGGATGCGGCGCTGGGCAGAAGCAGCCGCCGATTCCAGCTGCCCCGCG   474

                                   M   G   T   S   P   S   S   S   T   A   L     11
CGCCCCGGGCGCCCCTGCGAGTCCCCGGTTCAGCC ATG GGG ACC TCT CCG AGC AGC AGC ACC GCC CTC   542

 A   S   C   S   R   I   A   R   R   A   T   A   T   M   I   A   G   S   L   L     31
GCC TCC TGC AGC CGC ATC GCC CGC CGA GCC ACA GCC ACG ATG ATC GCG GGC TCC CTT CTC   602

 L   L   G   F   L   S   T   T   T   A   Q   P   E   Q   K   A   S   N   L   I     51
CTG CTT GGA TTC CTT AGC ACC ACC ACA GCT CAG CCA GAA CAG AAG GCC TCG AAT CTC ATT   662

 G   T   Y   R   H   V   D   R   A   T   G   Q   V   L   T   C   D   K   C   P     71
GGC ACA TAC CGC CAT GTT GAC CGT GCC ACC GGC CAG GTG CTA ACC TGT GAC AAG TGT CCA   722

 A   G   T   Y   V   S   E   H   C   T   N   T   S   L   R   V   C   S   S   C     91
GCA GGA ACC TAT GTC TCT GAG CAT TGT ACC AAC ACA AGC CTG CGC GTC TGC AGC AGT TGC   782

 P   V   G   T   F   T   R   H   E   N   G   I   E   K   C   H   D   C   S   Q    111
CCT GTG GGG ACC TTT ACC AGG CAT GAG AAT GGC ATA GAG AAA TGC CAT GAC TGT AGT CAG   842
```

FIG.4A

```
 P   C   P   W   P   M   I   E   K   L   P   C   A   A   L   T   D   R   E   C     131
CCA TGC CCA TGG CCA ATG ATT GAG AAA TTA CCT TGT GCT GCC TTG ACT GAC CGA GAA TGC    902

 T   C   P   P   G   M   F   Q   S   N   A   T   C   A   P   H   T   V   C   P     151
ACT TGC CCA CCT GGC ATG TTC CAG TCT AAC GCT ACC TGT GCC CCC CAT ACG GTG TGT CCT    962

 V   G   W   G   V   R   K   K   G   T   E   T   E   D   V   R   C   K   Q   C     171
GTG GGT TGG GGT GTG CGG AAG AAA GGG ACA GAG ACT GAG GAT GTG CGG TGT AAG CAG TGT   1022

 A   R   G   T   F   S   D   V   P   S   S   V   M   K   C   K   A   Y   T   D     191
GCT CGG GGT ACC TTC TCA GAT GTG CCT TCT AGT GTG ATG AAA TGC AAA GCA TAC ACA GAC   1082

 C   L   S   Q   N   L   V   V   I   K   P   G   T   K   E   T   D   N   V   C     211
TGT CTG AGT CAG AAC CTG GTG GTG ATC AAG CCG GGG ACC AAG GAG ACA GAC AAC GTC TGT   1142

 G   T   L   P   S   F   S   S   S   T   S   P   S   P   G   T   A   I   F   P     231
GGC ACA CTC CCG TCC TTC TCC AGC TCC ACC TCA CCT TCC CCT GGC ACA GCC ATC TTT CCA   1202

 R   P   E   H   M   E   T   H   E   V   P   S   S   T   Y   V   P   K   G   M     251
CGC CCT GAG CAC ATG GAA ACC CAT GAA GTC CCT TCC TCC ACT TAT GTT CCC AAA GGC ATG   1262

 N   S   T   E   S   N   S   S   A   S   V   R   P   K   V   L   S   S   I   Q     271
AAC TCA ACA GAA TCC AAC TCT TCT GCC TCT GTT AGA CCA AAG GTA CTG AGT AGC ATC CAG   1322

 E   G   T   V   P   D   N   T   S   S   A   R   G   K   E   D   V   N   K   T     291
GAA GGG ACA GTC CCT GAC AAC ACA AGC TCA GCA AGG GGG AAG GAA GAC GTG AAC AAG ACC   1382

 L   P   N   L   Q   V   V   N   H   Q   Q   G   P   H   H   R   H   I   L   K     311
CTC CCA AAC CTT CAG GTA GTC AAC CAC CAG CAA GGC CCC CAC CAC AGA CAC ATC CTG AAG   1442
```

FIG.4B

```
 L   L   P   S   M   E   A   T   G   G   E   K   S   S   T   P   I   K   G   P    331
CTG CTG CCG TCC ATG GAG GCC ACT GGG GGC GAG AAG TCC AGC ACG CCC ATC AAG GGC CCC  1502

 K   R   G   H   P   R   Q   N   L   H   K   H   F   D   I   N   E   H   L   P    351
AAG AGG GGA CAT CCT AGA CAG AAC CTA CAC AAG CAT TTT GAC ATC AAT GAG CAT TTG CCC  1562

 W   M   I   V   L   F   L   L   L   V   L   V   V   I   V   V   C   S   I   R    371
TGG ATG ATT GTG CTT TTC CTG CTG CTG GTG CTT GTG GTG ATT GTG GTG TGC AGT ATC CGG  1622

 K   S   S   R   T   L   K   K   G   P   R   Q   D   P   S   A   I   V   E   K    391
AAA AGC TCG AGG ACT CTG AAA AAG GGG CCC CGG CAG GAT CCC AGT GCC ATT GTG GAA AAG  1682

 A   G   L   K   K   S   M   T   P   T   Q   N   R   E   K   W   I   Y   Y   C    411
GCA GGG CTG AAG AAA TCC ATG ACT CCA ACC CAG AAC CGG GAG AAA TGG ATC TAC TAC TGC  1742

 N   G   H   G   I   D   I   L   K   L   V   A   A   Q   V   G   S   Q   W   K    431
AAT GGC CAT GGT ATC GAT ATC CTG AAG CTT GTA GCA GCC CAA GTG GGA AGC CAG TGG AAA  1802

 D   I   Y   Q   F   L   C   N   A   S   E   R   E   V   A   A   F   S   N   G    451
GAT ATC TAT CAG TTT CTT TGC AAT GCC AGT GAG AGG GAG GTT GCT GCT TTC TCC AAT GGG  1862

 Y   T   A   D   H   E   R   A   Y   A   A   L   Q   H   W   T   I   R   G   P    471
TAC ACA GCC GAC CAC GAG CGG GCC TAC GCA GCT CTG CAG CAC TGG ACC ATC CGG GGC CCC  1922

 E   A   S   L   A   Q   L   I   S   A   L   R   Q   H   R   R   N   D   V   V    491
GAG GCC AGC CTC GCC CAG CTA ATT AGC GCC CTG CGC CAG CAC CGG AGA AAC GAT GTT GTG  1982

 E   K   I   R   G   L   M   E   D   T   T   Q   L   E   T   D   K   L   A   L    511
GAG AAG ATT CGT GGG CTG ATG GAA GAC ACC ACC CAG CTG GAA ACT GAC AAA CTA GCT CTC  2042
```

FIG.4C

```
 P   M   S   P   S   P   L   S   P   S   P   I   P   S   P   N   A   K   L   E    531
CCG ATG AGC CCC AGC CCG CTT AGC CCG AGC CCC ATC CCC AGC CCC AAC GCG AAA CTT GAG  2102

 N   S   A   L   L   T   V   E   P   S   P   Q   D   L   L   F   K   W   L   D    551
AAT TCC GCT CTC CTG ACG GTG GAG CCT TCC CCA CAG GAT TTG CTA TTT AAG TGG CTT GAC  2162

 N   W   A   T   K   E   L   E   L   H   L   L   G   F   E   L   F   W   N   T    571
AAC TGG GCC ACC AAA GAA CTT GAA CTT CAC CTT TTA GGA TTT GAG CTG TTC TGG AAC ACA  2222

 L   L   H   F   G   K   S   K   S   S   A   S   G   A   L   S   I   E   N   L    591
TTG CTG CAC TTT GGA AAG TCA AAA TCA AGT GCC AGT GGC GCC CTT TCC ATA GAG AAT TTG  2282

 P   S   F   A   L   K   D   V   L   F   F   I   Y   T   *                        606
CCC AGC TTT GCT TTA AAA GAT GTC TTG TTT TTT ATA TAC ACA TAA                      2327

TCAATAGGTCCAATCTGCTCTCAAGGCCTTGGTCCTGGTGGGATTCCTTCACCAATTACTTTAATTAAAAATGGCTGCA  2406

ACTGTAAGAACCCTTGTCTGATATATTTGCAACTATGCTCCCATTTACAAATGTACCTTCTAATGCTCAGTTGCCAGGT  2485

TCCAATGCAAAGGTGGCGTGGACTCCCTTTGTGTGGGTGGGGTTTGTGGGTAGTGGTGAAGGACCGATATCAGAAAAAT  2564

GCCTTCAAGTGTACTAATTTATTAATAAACATTAGGTGTTTGTTACTTAAAAAAAAAAAAAAAAGGGCGGCCGC        2638
```

FIG.4D

```
Sequence         Start   End   Sequencetype
huTango75 II      (1  >  605)    PROTEIN
huTango75 I       (1  >  253)    PROTEIN
muTango 75        (1  >  573)    PROTEIN

                  1                                                         60
huTango75 II      MGTSPSSSTALASCSRIARRATATMIAGSLLLLGFLSTTTAQPEQKASNLIGTYRHVDRA
huTango75 I       MGTSPSSSTALASCSRIARRATATMIAGSLLLLGFLSTTTAQPEQKASNLIGTYRHVDRA
muTango 75        M-----------------------------------------------------------

                  61                                                       120
huTango75 II      TGQVLTCDKCPAGTYVSEHCTNTSLRVCSSCPVGTFTRHENGIEKCHDCSQPCPWPMIEK
huTango75 I       TGQVLTCDKCPAGTYVSEHCTNTSLRVCSSCPVGTFTRHENGIEKCHDCSQPCPWPMIEK
muTango 75        -----------------------SLRVCSSCPAGTFTRHENGIERCHDCSQPCPWPMIER

                  121                                                      180
huTango75 II      LPCAALTDRECTCPPGMFQSNATCAPHTVCPVGWGVRKKGTETEDVRCKQCARGTFSDVP
huTango75 I       LPCAALTDRECTCPPGMFQSNATCAPHTVCPVGWGVRKKGTETEDVRCKQCARGTFSDVP
muTango 75        LPCAALTDRECICPPGMYQSNGTCAPHTVCPVGWGVRKKGTENEDVRCKQCARGTFSDVP

                  181                                                      240
huTango75 II      SSVMKCKAYTDCLSQNLVVIKPGTKETDNVCGTLPSFSSSTSPSPGTAIFPRPEHMETHE
huTango75 I       SSVMKCKAYTDCLSQNLVVIKPGTKETDNVCGTLPSFSSSTSPSPGTAIFPRPEHMETHE
muTango 75        SSVMKCKAHTDCLGQNLEVVKPGTKETDNVCGMRLFFSSTNPPSSGTVTFSHPEHMESHD

                  241                                                      300
huTango75 II      VPSSTYVPKGMNSTESNSSASVRPKVLSSIQEGTVPDNTSSARGKEDVNKTLPNLQVVNH
huTango75 I       VPSSTYVPK---------------------------------------------------
muTango 75        VPSSTYEPQGMNSTDSNSTASVRTKVPSGIEEGTVPDNTSSTSGKEGTNRTLPNPPQVTH
```

FIG.5A

```
               301                                                        360
huTango75 II   QQGPHHRHILKLLPSMEATGGEKSSTPIKGPKRGHPRQNLHKHFDINEHLPWMIVLFLLL
huTango75 I    ------------------------------------------------------------
muTango 75     QQAPHHRHILKLLPSSMEATGEKSSTAIKAPKRGHPRQNAHKHFDINEHLPWMIVLFLLL

               361                                                        420
huTango75 II   VLVVIVVCSIRKSSRTLKKGPRQDPSAIVEKAGLKKSMTPTQNREKWIYYCNGHGIDILK
huTango75 I    ------------------------------------------------------------
muTango 75     VLVLIVVCSIRKSSRTLKKGPRQDPSAIVEKAGLKKSLTPTQNREKWIYYRNGHGIDILK

               421                                                        480
huTango75 II   LVAAQVGSQWKDIYQFLCNASEREVAAFSNGYTADHERAYAALQHWTIRGPEASLAQLIS
huTango75 I    ------------------------------------DQRY--------------------
muTango 75     LVAAQVGSQWKDIYQFLCNASEREVAAFSNGYTADHERAYAALQHWTIRGPEASLAQLIS

               481                                                        540
huTango75 II   ALRQHRRNDVVEKIRGLMEDTTQLETDKLALPMSPSPLSPSPIPSPNAKLENSALLTVEP
huTango75 I    ------------------------------------------------------------
muTango 75     ALRQHRRNDVVEKIRGLMEDTTQLETDKLALPMSPSPLSPSPIPSPNVKLENSTLLTVEP

               541                                                        600
huTango75 II   SPQD------------LL-----------FKWLDNWATKELELHLL--------GFELFW
huTango75 I    ------------------------------------------------------------
muTango 75     SPLDKNKCFFVDESEPLLRCDSTSSGSSALSRNGSFITKEKKDTVLRQVRLDPCDLQPIF

               601                                      655
huTango75 II   NTLLHFGKS---KSSASGALSIENLPS-FALKDV---------LFFIYT------
huTango75 I    -------------------------------------------------------
muTango 75     DDMLHILNPEELRVIEEIPQAEDKLDRLFEIIGVKSQEASQTLLDSVYSHLPDLL
```

FIG.5B

```
Alignment of:
Sequence                  Start   End  Sequencetype

human TNFR1 DD            (1  >   86)   PROTEIN
human FAS DD              (1  >   85)   PROTEIN
human TRADD DD            (1  >   91)   PROTEIN
human FADD DD             (1  >   85)   PROTEIN
human RIP DD              (1  >   87)   PROTEIN
human TRL II DD           (1  >   84)   PROTEIN
murine TRL DD             (1  >   84)   PROTEIN

                          1        10      *  20        30        40        50     *  * 60

human TNFR1 DD            PATLYAVVENVPPLRWKEFVRRLGLSDHEIDRLELQNGR------CLREAQYSMLATWRR
human FAS DD              SKYITTIAGVMTLSQVKGFVRKNGVNEAKIDEIKNDNVQ------DTAEQKVQLLRNWHQ
human TRADD DD            SLKDQQTFARSVGLKWRKVGRSLQRGCRALRDPALDSLAYEYEREGLYEQAFQLLRRFVQ
human FADD DD             LCAAFNVICDNVGKDWRRLARQLKVSDTKIDSIEDRYPR------NLTERVRESLRIWKN
human RIP DD              TDKHLDPIRENLGKHWKNCARKLGFTQSQIDEIDHDYERD-----GLKEKVYQMLQKWVM
human TRL II DD           GIDILKLVAAQVGSQWKDIYQFLCNASEREVAAFSNGYTAD------HERAYAALQHWTI
murine TRL DD             GIDILKLVAAQVGSQWKDIYQFLCNASEREVAAFSNGYTAD------HERAYAALQHWTI

                                   70 *    *  80
human TNFR1 DD            RTPRREATLELLGRVLRDMDLLGCLEDIEEAL
human FAS DD              LHG-KKEAYDTLIKDLKKANLCTLAEKIQTII
human TRADD DD            AEG-RRATLQRLVEALEENELTSLAEDLLGLT
human FADD DD             TEK-ENATVAHLVGALRSCQMNLVADLVQEVQ
human RIP DD              REGIKGATVGKLAQALHQCSRIDLLSSLIYVS
human TRL DD              R-GP-EASLAQLISALRQHRRNDVVEKIRGLM
murine TRL DD             R-GP-EASLAQLISALRQHRRNDVVEKIRGLM
```

FIG.6

```
                        SEQUENCE LISTING

(1) GENERAL INFORMATION:

   (iii) NUMBER OF SEQUENCES: 31

(2) INFORMATION FOR SEQ ID NO:1:

     (i) SEQUENCE CHARACTERISTICS:
          (A) LENGTH: 3331 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 344..2065

    (xi) SEQUENCE DESCRIPTION: SEQ ID NO:1:

GTCGACCCAC GGTCCGGGAG ACTTACCACC AAGTAGCAGG ATCTTCTCTT TCTCAATTTC     60

CAATATGAAA TTAAATTTCC CAACAAGAAA ACCAACCACT ATCCATCGCC AACCACCTCT    120

GCCCCTACTT TCAGACTCAG AAGGAAGAAA ACTAAGTATA TCGTAAACTC TAAGGAGGAA    180

ACCTCAAGAA CCGCTTGGAT TCCTCAGCAC CATCACAGCT CAACCAGAAC AAAAGACTCT    240

GAGTCTCCCT GGCACCTACC GCCATGTTGA CCGTACCACT GGCCAGGTGC TAACCTGCGA    300

CAAGTGCCCA GCAGGAACGT ATGTCTCCGA GCACTGTACC AAC ATG AGC CTG CGA      355
                                                Met Ser Leu Arg
                                                  1

GTC TGC AGC AGC TGC CCC GCG GGG ACC TTT ACC AGG CAC GAG AAC GGC      403
Val Cys Ser Ser Cys Pro Ala Gly Thr Phe Thr Arg His Glu Asn Gly
  5                  10                  15                  20

ATA GAG AGA TGC CAT GAC TGT AGT CAG CCA TGT CCA TGG CCG ATG ATT      451
Ile Glu Arg Cys His Asp Cys Ser Gln Pro Cys Pro Trp Pro Met Ile
                 25                  30                  35

GAG AGA TTA CCT TGT GCT GCC TTG ACT GAC CGA GAG TGC ATC TGC CCA      499
Glu Arg Leu Pro Cys Ala Ala Leu Thr Asp Arg Glu Cys Ile Cys Pro
             40                  45                  50

CCT GGA ATG TAT CAG TCT AAT GGT ACC TGC GCT CCC CAT ACA GTG TGC      547
Pro Gly Met Tyr Gln Ser Asn Gly Thr Cys Ala Pro His Thr Val Cys
         55                  60                  65

CCC GTG GGC TGG GGT GTG CGG AAG AAA GGG ACA GAG AAT GAA GAT GTG      595
Pro Val Gly Trp Gly Val Arg Lys Lys Gly Thr Glu Asn Glu Asp Val
     70                  75                  80
```

-continued

```
CGC TGT AAG CAG TGC GCT CGG GGT ACC TTC TCT GAC GTG CCT TCC AGT      643
Arg Cys Lys Gln Cys Ala Arg Gly Thr Phe Ser Asp Val Pro Ser Ser
 85                  90                  95                 100

GTG ATG AAG TGT AAA GCT CAC ACG GAC TGT CTG GGT CAG AAC CTG GAG      691
Val Met Lys Cys Lys Ala His Thr Asp Cys Leu Gly Gln Asn Leu Glu
                105                 110                 115

GTG GTC AAG CCA GGG ACC AAG GAG ACA GAC AAC GTC TGT GGC ATG CGC      739
Val Val Lys Pro Gly Thr Lys Glu Thr Asp Asn Val Cys Gly Met Arg
            120                 125                 130

CTG TTC TTC TCC AGC ACA AAC CCA CCT TCC TCT GGC ACA GTT ACC TTT      787
Leu Phe Phe Ser Ser Thr Asn Pro Pro Ser Ser Gly Thr Val Thr Phe
        135                 140                 145

TCT CAC CCT GAG CAT ATG GAA TCC CAC GAT GTC CCT TCC TCC ACC TAT      835
Ser His Pro Glu His Met Glu Ser His Asp Val Pro Ser Ser Thr Tyr
    150                 155                 160

GAG CCC CAA GGC ATG AAC TCA ACA GAT TCC AAC TCT ACT GCC TCT GTT      883
Glu Pro Gln Gly Met Asn Ser Thr Asp Ser Asn Ser Thr Ala Ser Val
165                 170                 175                 180

AGA ACT AAG GTA CCA AGT GGC ATC GAG GAA GGG ACA GTG CCT GAC AAT      931
Arg Thr Lys Val Pro Ser Gly Ile Glu Glu Gly Thr Val Pro Asp Asn
                185                 190                 195

ACG AGC TCA ACC AGT GGG AAG GAA GGC ACT AAT AGG ACC CTG CCA AAC      979
Thr Ser Ser Thr Ser Gly Lys Glu Gly Thr Asn Arg Thr Leu Pro Asn
            200                 205                 210

CCA CCA CAA GTT ACC CAC CAG CAA GCC CCC CAC CAC AGA CAC ATT CTG     1027
Pro Pro Gln Val Thr His Gln Gln Ala Pro His His Arg His Ile Leu
        215                 220                 225

AAG CTG CTG CCA TCG TCC ATG GAG GCC ACG GGT GAG AAG TCC AGC ACA     1075
Lys Leu Leu Pro Ser Ser Met Glu Ala Thr Gly Glu Lys Ser Ser Thr
    230                 235                 240

GCC ATC AAG GCC CCC AAG AGG GGT CAC CCC AGA CAG AAC GCT CAC AAG     1123
Ala Ile Lys Ala Pro Lys Arg Gly His Pro Arg Gln Asn Ala His Lys
245                 250                 255                 260

CAT TTC GAC ATC AAC GAG CAC TTG CCT TGG ATG ATC GTC CTC TTC CTT     1171
His Phe Asp Ile Asn Glu His Leu Pro Trp Met Ile Val Leu Phe Leu
                265                 270                 275

CTG CTG GTC CTG GTG CTG ATA GTG GTG TGC AGT ATC CGA AAG AGC TCC     1219
Leu Leu Val Leu Val Leu Ile Val Val Cys Ser Ile Arg Lys Ser Ser
            280                 285                 290

AGG ACT CTC AAA AAG GGG CCC CGG CAG GAT CCC AGC GCC ATA GTG GAA     1267
Arg Thr Leu Lys Lys Gly Pro Arg Gln Asp Pro Ser Ala Ile Val Glu
        295                 300                 305

AAG GCG GGG CTG AAG AAG TCC CTG ACT CCC ACC CAG AAC CGG GAG AAA     1315
Lys Ala Gly Leu Lys Lys Ser Leu Thr Pro Thr Gln Asn Arg Glu Lys
    310                 315                 320

TGG ATC TAC TAC CGC AAC GGC CAT GGT ATT GAC ATC TTG AAG CTT GTA     1363
Trp Ile Tyr Tyr Arg Asn Gly His Gly Ile Asp Ile Leu Lys Leu Val
325                 330                 335                 340

GCA GCC CAG GTG GGA AGC CAG TGG AAG GAC ATC TAT CAG TTT CTT TGC     1411
Ala Ala Gln Val Gly Ser Gln Trp Lys Asp Ile Tyr Gln Phe Leu Cys
                345                 350                 355

AAC GCC AGT GAG AGG GAG GTG GCG GCC TTC TCC AAT GGA TAC ACT GCA     1459
Asn Ala Ser Glu Arg Glu Val Ala Ala Phe Ser Asn Gly Tyr Thr Ala
            360                 365                 370

GAT CAT GAA CGG GCC TAC GCG GCT CTG CAG CAC TGG ACC ATC CGT GGC     1507
Asp His Glu Arg Ala Tyr Ala Ala Leu Gln His Trp Thr Ile Arg Gly
        375                 380                 385

CCT GAG GCC AGC CTT GCC CAG CTC ATT AGC GCC TTG CGC CAG CAC CGA     1555
Pro Glu Ala Ser Leu Ala Gln Leu Ile Ser Ala Leu Arg Gln His Arg
    390                 395                 400
```

-continued

```
CGC AAT GAT GTT GTG GAG AAG ATT CGT GGG CTG ATG GAA GAC ACC ACG     1603
Arg Asn Asp Val Val Glu Lys Ile Arg Gly Leu Met Glu Asp Thr Thr
405                 410                 415                 420

CAG TTG GAA ACA GAC AAA CTG GCT CTC CCC ATG AGC CCC AGT CCG CTG     1651
Gln Leu Glu Thr Asp Lys Leu Ala Leu Pro Met Ser Pro Ser Pro Leu
                425                 430                 435

AGC CCG AGC CCC ATC CCC AGT CCT AAC GTG AAA CTT GAG AAT TCC ACT     1699
Ser Pro Ser Pro Ile Pro Ser Pro Asn Val Lys Leu Glu Asn Ser Thr
            440                 445                 450

CTC CTG ACA GTG GAG CCC TCA CCG CTG GAC AAG AAC AAG TGC TTC TTC     1747
Leu Leu Thr Val Glu Pro Ser Pro Leu Asp Lys Asn Lys Cys Phe Phe
        455                 460                 465

GTG GAC GAG TCA GAG CCC CTT CTG CGT TGC GAC TCC ACA TCC AGT GGC     1795
Val Asp Glu Ser Glu Pro Leu Leu Arg Cys Asp Ser Thr Ser Ser Gly
    470                 475                 480

TCT TCA GCA CTG AGC AGA AAC GGC TCC TTT ATT ACC AAA GAA AAG AAG     1843
Ser Ser Ala Leu Ser Arg Asn Gly Ser Phe Ile Thr Lys Glu Lys Lys
485                 490                 495                 500

GAC ACA GTG TTG CGG CAG GTC CGC CTG GAC CCC TGT GAC TTG CAG CCC     1891
Asp Thr Val Leu Arg Gln Val Arg Leu Asp Pro Cys Asp Leu Gln Pro
                505                 510                 515

ATC TTT GAT GAC ATG CTG CAT ATC CTG AAC CCC GAG GAG CTG CGG GTG     1939
Ile Phe Asp Asp Met Leu His Ile Leu Asn Pro Glu Glu Leu Arg Val
            520                 525                 530

ATT GAA GAG ATT CCC CAG GCT GAG GAC AAA CTG GAC CGC CTC TTC GAG     1987
Ile Glu Glu Ile Pro Gln Ala Glu Asp Lys Leu Asp Arg Leu Phe Glu
        535                 540                 545

ATC ATT GGG GTC AAG AGC CAA GAA GCC AGC CAG ACC CTC TTG GAC TCT     2035
Ile Ile Gly Val Lys Ser Gln Glu Ala Ser Gln Thr Leu Leu Asp Ser
    550                 555                 560

GTG TAC AGT CAT CTT CCT GAC CTA TTG TAGAACACAG GGCACTGCA           2082
Val Tyr Ser His Leu Pro Asp Leu Leu
565                 570

TTCTGGGAAT CAACCTACTG GCGGGGTGAT TTCATTTCGT TTCTGACTTT TGTGTTTTGG   2142

TGTGTATGTA TGTGTTTAAC AGAGTGTATG GCCGGTGAGT TTGGGGTTCT TTCTTTCTTT   2202

CTTTCTTTCT TTCTTTCTTT CTTTCTTTCT TTCTTCCTTC CTTCCTTCCT TCCTTCCTTC   2262

CTTCCTTCCT TCCTTCCTGA AAGTGAATGT ATAAAGCCTT TACAATGTAT AACTGTTGGA   2322

AAATGCCCAC CACTAAATTT TTTTTAAGTT CCATATATTC TCCATTTTTG CCTTCTTATA   2382

TATATCTTCA ACACTATTCT GTGCACTTTA AAAACTTAAC ATAAACGCAG TGTGACTTCT   2442

CCCATATGCT GGGTTCCGAG ACTCTCAACT TCTTAAAAAC CTAATGGCAT CTTGTGACTC   2502

CTAGAAGTAG ACATAAGTCT TTCAACCTTC ACACCTACTC TTTCTGTTTT AATTATTATT   2562

GCTATTTGTC TTATTGTTTG TGCTTTACAA GCGTTCTTGA GGACGGAGGG AATCTACGAC   2622

CCTGTTGATG ACTGTAACTC TATTCGACTT TGAGTTGTCT TCTTCATGTC TTGTTATATA   2682

GTTCATATTC ATGGCTGAAA CTTGACCATA CTCCCTAGCG CCGCTGATTG TATGGTTTTC   2742

GTCTGGACAC CGTACACTGC CTGATAACTT GTGCACCTCT TAACGCTACT ATGCTCTGGG   2802

CTGGAGAATG AAATCTTTAA GTCACCAGGA CTTGCTGTTT CAGTGGCTTG ACACCTGGGC   2862

CACCAAAGAA CTCGATCTTC ATCTTTTAGG GACACCTCTG CTGCACCTTG GAAAGCCAAC   2922

CTTAAGTGCC AGTGGCACTT TATGCCCAGC TTTGCTTTGA AAGATATCTT TCTTGTTTTT   2982

TTTTATCCTT CTCTTTCTCT CTTTTTTTTA AAAATACACA TAGTCAATAG GTCCAGTCTG   3042

CCCTCAAGGC CTTGCTGGGT TTTTTTCGTC ATCCAATCAC TTTCATTAAA AATGGCTGCA   3102
```

-continued

```
GCTGTAAGAA CTCTTGTCTG ATAAATTTTC AACTATGCTC TCATTTATCT ACCTGCCCTC   3162

TGATGCTCAG TCGTCAGACT CTAATGCAAA GGTGGACGTC GGCTGCCTTT GCGTGGGCGG   3222

GCTTAGTGGT GAGGAACTGA TATCAGAAAA AAATGCCTTC AAGTATACTA ATTTATTAAT   3282

AAATATTAGG TGTTTGTTAA AAAAAAAAAA AAAAAAAAAA AAAGCGGCC               3331
```

(2) INFORMATION FOR SEQ ID NO:2:

(i) SEQUENCE CHARACTERISTICS:
(A) LENGTH: 573 amino acids
(B) TYPE: amino acid
(D) TOPOLOGY: linear (ii) MOLECULE TYPE: protein (xi) SEQUENCE DESCRIPTION: SEQ ID NO:2:

```
Met Ser Leu Arg Val Cys Ser Ser Cys Pro Ala Gly Thr Phe Thr Arg
  1               5                  10                  15

His Glu Asn Gly Ile Glu Arg Cys His Asp Cys Ser Gln Pro Cys Pro
             20                  25                  30

Trp Pro Met Ile Glu Arg Leu Pro Cys Ala Ala Leu Thr Asp Arg Glu
         35                  40                  45

Cys Ile Cys Pro Pro Gly Met Tyr Gln Ser Asn Gly Thr Cys Ala Pro
     50                  55                  60

His Thr Val Cys Pro Val Gly Trp Gly Val Arg Lys Lys Gly Thr Glu
 65                  70                  75                  80

Asn Glu Asp Val Arg Cys Lys Gln Cys Ala Arg Gly Thr Phe Ser Asp
                 85                  90                  95

Val Pro Ser Ser Val Met Lys Cys Lys Ala His Thr Asp Cys Leu Gly
            100                 105                 110

Gln Asn Leu Glu Val Val Lys Pro Gly Thr Lys Glu Thr Asp Asn Val
        115                 120                 125

Cys Gly Met Arg Leu Phe Phe Ser Ser Thr Asn Pro Pro Ser Ser Gly
    130                 135                 140

Thr Val Thr Phe Ser His Pro Glu His Met Glu Ser His Asp Val Pro
145                 150                 155                 160

Ser Ser Thr Tyr Glu Pro Gln Gly Met Asn Ser Thr Asp Ser Asn Ser
                165                 170                 175

Thr Ala Ser Val Arg Thr Lys Val Pro Ser Gly Ile Glu Glu Gly Thr
            180                 185                 190

Val Pro Asp Asn Thr Ser Ser Thr Ser Gly Lys Glu Gly Thr Asn Arg
        195                 200                 205

Thr Leu Pro Asn Pro Pro Gln Val Thr His Gln Gln Ala Pro His His
    210                 215                 220

Arg His Ile Leu Lys Leu Leu Pro Ser Ser Met Glu Ala Thr Gly Glu
225                 230                 235                 240

Lys Ser Ser Thr Ala Ile Lys Ala Pro Lys Arg Gly His Pro Arg Gln
                245                 250                 255

Asn Ala His Lys His Phe Asp Ile Asn Glu His Leu Pro Trp Met Ile
            260                 265                 270

Val Leu Phe Leu Leu Leu Val Leu Val Leu Ile Val Val Cys Ser Ile
        275                 280                 285

Arg Lys Ser Ser Arg Thr Leu Lys Lys Gly Pro Arg Gln Asp Pro Ser
    290                 295                 300

Ala Ile Val Glu Lys Ala Gly Leu Lys Lys Ser Leu Thr Pro Thr Gln
305                 310                 315                 320
```

-continued

```
Asn Arg Glu Lys Trp Ile Tyr Tyr Arg Asn Gly His Gly Ile Asp Ile
                325                 330                 335

Leu Lys Leu Val Ala Ala Gln Val Gly Ser Gln Trp Lys Asp Ile Tyr
            340                 345                 350

Gln Phe Leu Cys Asn Ala Ser Glu Arg Glu Val Ala Ala Phe Ser Asn
        355                 360                 365

Gly Tyr Thr Ala Asp His Glu Arg Ala Tyr Ala Ala Leu Gln His Trp
    370                 375                 380

Thr Ile Arg Gly Pro Glu Ala Ser Leu Ala Gln Leu Ile Ser Ala Leu
385                 390                 395                 400

Arg Gln His Arg Arg Asn Asp Val Val Glu Lys Ile Arg Gly Leu Met
                405                 410                 415

Glu Asp Thr Thr Gln Leu Glu Thr Asp Lys Leu Ala Leu Pro Met Ser
            420                 425                 430

Pro Ser Pro Leu Ser Pro Ser Pro Ile Pro Ser Pro Asn Val Lys Leu
        435                 440                 445

Glu Asn Ser Thr Leu Leu Thr Val Glu Pro Ser Pro Leu Asp Lys Asn
    450                 455                 460

Lys Cys Phe Phe Val Asp Glu Ser Glu Pro Leu Leu Arg Cys Asp Ser
465                 470                 475                 480

Thr Ser Ser Gly Ser Ser Ala Leu Ser Arg Asn Gly Ser Phe Ile Thr
                485                 490                 495

Lys Glu Lys Lys Asp Thr Val Leu Arg Gln Val Arg Leu Asp Pro Cys
            500                 505                 510

Asp Leu Gln Pro Ile Phe Asp Asp Met Leu His Ile Leu Asn Pro Glu
        515                 520                 525

Glu Leu Arg Val Ile Glu Glu Ile Pro Gln Ala Glu Asp Lys Leu Asp
    530                 535                 540

Arg Leu Phe Glu Ile Ile Gly Val Lys Ser Gln Glu Ala Ser Gln Thr
545                 550                 555                 560

Leu Leu Asp Ser Val Tyr Ser His Leu Pro Asp Leu Leu
                565                 570

(2) INFORMATION FOR SEQ ID NO:3:

     (i) SEQUENCE CHARACTERISTICS:
          (A) LENGTH: 2612 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 190..951

    (xi) SEQUENCE DESCRIPTION: SEQ ID NO:3:

GCTCAGCGCC CCTAGACCCT CCCTTGCCGC CTCCCTCCTC TGCCCGGCCG TACCAGTGCA      60

CATGGGGTGT TGGAGGTAGA TGGGCTCCCG GCCCGGGAGG CGGCGGTGGA TGCGGCGCTG     120

GGCAGAAGCA GCCGCCGATT CCAGCTGCCC CGCGCGCCCC GGGCGCCCCT GCGAGTCCCC     180

GGTTCAGCC ATG GGG ACC TCT CCG AGC AGC AGC ACC GCC CTC GCC TCC         228
          Met Gly Thr Ser Pro Ser Ser Ser Thr Ala Leu Ala Ser
            1               5                  10

TGC AGC CGC ATC GCC CGC CGA GCC ACA GCC ACG ATG ATC GCG GGC TCC       276
Cys Ser Arg Ile Ala Arg Arg Ala Thr Ala Thr Met Ile Ala Gly Ser
     15                  20                  25
```

-continued

```
CTT CTC CTG CTT GGA TTC CTT AGC ACC ACC ACA GCT CAG CCA GAA CAG      324
Leu Leu Leu Leu Gly Phe Leu Ser Thr Thr Thr Ala Gln Pro Glu Gln
 30                  35                  40                  45

AAG GCC TCG AAT CTC ATT GGC ACA TAC CGC CAT GTT GAC CGT GCC ACC      372
Lys Ala Ser Asn Leu Ile Gly Thr Tyr Arg His Val Asp Arg Ala Thr
                 50                  55                  60

GGC CAG GTG CTA ACC TGT GAC AAG TGT CCA GCA GGA ACC TAT GTC TCT      420
Gly Gln Val Leu Thr Cys Asp Lys Cys Pro Ala Gly Thr Tyr Val Ser
             65                  70                  75

GAG CAT TGT ACC AAC ACA AGC CTG CGC GTC TGC AGC AGT TGC CCT GTG      468
Glu His Cys Thr Asn Thr Ser Leu Arg Val Cys Ser Ser Cys Pro Val
         80                  85                  90

GGG ACC TTT ACC AGG CAT GAG AAT GGC ATA GAG AAA TGC CAT GAC TGT      516
Gly Thr Phe Thr Arg His Glu Asn Gly Ile Glu Lys Cys His Asp Cys
     95                 100                 105

AGT CAG CCA TGC CCA TGG CCA ATG ATT GAG AAA TTA CCT TGT GCT GCC      564
Ser Gln Pro Cys Pro Trp Pro Met Ile Glu Lys Leu Pro Cys Ala Ala
110                 115                 120                 125

TTG ACT GAC CGA GAA TGC ACT TGC CCA CCT GGC ATG TTC CAG TCT AAC      612
Leu Thr Asp Arg Glu Cys Thr Cys Pro Pro Gly Met Phe Gln Ser Asn
                130                 135                 140

GCT ACC TGT GCC CCC CAT ACG GTG TGT CCT GTG GGT TGG GGT GTG CGG      660
Ala Thr Cys Ala Pro His Thr Val Cys Pro Val Gly Trp Gly Val Arg
            145                 150                 155

AAG AAA GGG ACA GAG ACT GAG GAT GTG CGG TGT AAG CAG TGT GCT CGG      708
Lys Lys Gly Thr Glu Thr Glu Asp Val Arg Cys Lys Gln Cys Ala Arg
        160                 165                 170

GGT ACC TTC TCA GAT GTG CCT TCT AGT GTG ATG AAA TGC AAA GCA TAC      756
Gly Thr Phe Ser Asp Val Pro Ser Ser Val Met Lys Cys Lys Ala Tyr
    175                 180                 185

ACA GAC TGT CTG AGT CAG AAC CTG GTG GTG ATC AAG CCG GGG ACC AAG      804
Thr Asp Cys Leu Ser Gln Asn Leu Val Val Ile Lys Pro Gly Thr Lys
190                 195                 200                 205

GAG ACA GAC AAC GTC TGT GGC ACA CTC CCG TCC TTC TCC AGC TCC ACC      852
Glu Thr Asp Asn Val Cys Gly Thr Leu Pro Ser Phe Ser Ser Ser Thr
                210                 215                 220

TCA CCT TCC CCT GGC ACA GCC ATC TTT CCA CGC CCT GAG CAC ATG GAA      900
Ser Pro Ser Pro Gly Thr Ala Ile Phe Pro Arg Pro Glu His Met Glu
            225                 230                 235

ACC CAT GAA GTC CCT TCC TCC ACT TAT GTT CCC AAA GAC CAA AGG TAC      948
Thr His Glu Val Pro Ser Ser Thr Tyr Val Pro Lys Asp Gln Arg Tyr
        240                 245                 250

TGAGTAGCAT CCAGGAAGGG ACAGTCCCTG ACAACACAAG CTCAGCAAGG GGGAAGGAAG   1008

ACGTGAACAA GACCCTCCCA AACCTTCAGG TAGTCAACCA CCAGCAAGGC CCCCACCACA   1068

GACACATCCT GAAGCTGCTG CCGTCCATGG AGGCCACTGG GGGCGAGAAG TCCAGCACGC   1128

CCATCAAGGG CCCCAAGAGG GGACATCCTA GACAGAACCT ACACAAGCAT TTTGACATCA   1188

ATGAGCATTT GCCCTGGATG ATTGTGCTTT TCCTGCTGCT GGTGCTTGTG GTGATTGTGG   1248

TGTGCAGTAT CCGGAAAAGC TCGAGGACTC TGAAAAAGGG GCCCCGGCAG GATCCCAGTG   1308

CCATTGTGGA AAAGGCAGGG CTGAAGAAAT CCATGACTCC AACCCAGAAC CGGGAGAAAT   1368

GGATCTACTA CTGCAATGGC CATGGTATCG ATATCCTGAA GCTTGTAGCA GCCCAAGTGG   1428

GAAGCCAGTG GAAAGATATC TATCAGTTTC TTTGCAATGC CAGTGAGAGG GAGGTTGCTG   1488

CTTTCTCCAA TGGGTACACA GCCGACCACG AGCGGGCCTA CGCAGCTCTG CAGCACTGGA   1548

CCATCCGGGG CCCCGAGGCC AGCCTCGCCC AGCTAATTAG CGCCCTGCGC CAGCACCGGA   1608
```

-continued

```
GAAACGATGT TGTGGAGAAG ATTCGTGGGC TGATGGAAGA CACCACCCAG GTAATGGAGC   1668

CCTTGTTGTG TGTCATTACC ACCGACCTAT TGCCCCTATG CTTCAAATTT TATCAGTTGT   1728

ATGGGAACAA AGAAAAATAA CATATTCGGT GGATAGGCAC ACACACACAC ACACGCATAC   1788

GCCTGCACAC ACACACACAC ACCCTACCTT CTAGGACGGG GGTTCTCAGT GGCCGTCTAT   1848

TAGAATCATC TAGAAAACTT TAAAAAAAAA TACTGATGCT CAGACCCTAC CTGCAGACCA   1908

GTCACATCAG AATCTCCAGG GGGCAGAGCG TGAATCGGTA TTTGTAAAAG CTCTTTGTTA   1968

CTCCATTTAC AATCCATTTT GCATGACACA CTTTGAACAA AACCAAGAAA AAATACTTTT   2028

TACTACACCG CCTCTCCTCC AGAGGGTGTT TTTGTGATGT GGCTTATGAA GGCAGCATTC   2088

TTGCCTCCTG AGGATGCAGG TGGTGCTAGC GGCAGTTGAT GACAGAACTG ATTCTCCTCC   2148

TTGGGTTGTT CCGTGGAGCA CATCAGATGG GAACTGAGGG GACCCAGGAG TGTGATTTCT   2208

TTATAGCTAA TAAGCCCTGG CTTTGGAGCC AGACAGCGCT GGATTTGAAT CCTGGCTCTG   2268

GTACATATTA GCTTAGGTGA TGAAGGGTAA GTTACTTCAA CTTTCCTTGC CTCTGTTATT   2328

CACATTTTCA AGTCTGCTAT ATAAGATTAA GATGAGAAAT AAAGCATATA AAATGCCTGA   2388

CTCATTGAAA GTGTTCTACA AGTGGTAGTT ACGACCATGA TGTAACTCAT TTTACTTAGC   2448

CTTTCTTTAA TTGTATGTAC TTCCCTGAAA GGCCATGAAT AAAGTTCAGA TTTGGATATT   2508

GAATCATATT TTCCACAGAC TTCAATTCAG GTTTCAGAAC ATATTCCCAA AGTAAAGAAA   2568

ATGCTGCCAC TAAGACTAGA TAAAACCCAC TTCAGATTGG TAAC                    2612
```

(2) INFORMATION FOR SEQ ID NO:4:

(i) SEQUENCE CHARACTERISTICS:
(A) LENGTH: 253 amino acids
(B) TYPE: amino acid
(D) TOPOLOGY: linear (ii) MOLECULE TYPE: protein (xi) SEQUENCE DESCRIPTION: SEQ ID NO:4:

```
Met Gly Thr Ser Pro Ser Ser Ser Thr Ala Leu Ala Ser Cys Ser Arg
  1               5                  10                  15

Ile Ala Arg Arg Ala Thr Ala Thr Met Ile Ala Gly Ser Leu Leu Leu
             20                  25                  30

Leu Gly Phe Leu Ser Thr Thr Thr Ala Gln Pro Glu Gln Lys Ala Ser
         35                  40                  45

Asn Leu Ile Gly Thr Tyr Arg His Val Asp Arg Ala Thr Gly Gln Val
     50                  55                  60

Leu Thr Cys Asp Lys Cys Pro Ala Gly Thr Tyr Val Ser Glu His Cys
 65                  70                  75                  80

Thr Asn Thr Ser Leu Arg Val Cys Ser Ser Cys Pro Val Gly Thr Phe
                 85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
        115                 120                 125

Arg Glu Cys Thr Cys Pro Pro Gly Met Phe Gln Ser Asn Ala Thr Cys
    130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175
```

-continued

```
Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
        195                 200                 205

Asn Val Cys Gly Thr Leu Pro Ser Phe Ser Ser Ser Thr Ser Pro Ser
    210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Asp Gln Arg Tyr
                245                 250
```

(2) INFORMATION FOR SEQ ID NO:5:

(i) SEQUENCE CHARACTERISTICS:
(A) LENGTH: 1719 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..1719

(xi) SEQUENCE DESCRIPTION: SEQ ID NO:5:

```
ATG AGC CTG CGA GTC TGC AGC AGC TGC CCC GCG GGG ACC TTT ACC AGG       48
Met Ser Leu Arg Val Cys Ser Ser Cys Pro Ala Gly Thr Phe Thr Arg
  1               5                  10                  15

CAC GAG AAC GGC ATA GAG AGA TGC CAT GAC TGT AGT CAG CCA TGT CCA       96
His Glu Asn Gly Ile Glu Arg Cys His Asp Cys Ser Gln Pro Cys Pro
             20                  25                  30

TGG CCG ATG ATT GAG AGA TTA CCT TGT GCT GCC TTG ACT GAC CGA GAG      144
Trp Pro Met Ile Glu Arg Leu Pro Cys Ala Ala Leu Thr Asp Arg Glu
         35                  40                  45

TGC ATC TGC CCA CCT GGA ATG TAT CAG TCT AAT GGT ACC TGC GCT CCC      192
Cys Ile Cys Pro Pro Gly Met Tyr Gln Ser Asn Gly Thr Cys Ala Pro
     50                  55                  60

CAT ACA GTG TGC CCC GTG GGC TGG GGT GTG CGG AAG AAA GGG ACA GAG      240
His Thr Val Cys Pro Val Gly Trp Gly Val Arg Lys Lys Gly Thr Glu
 65                  70                  75                  80

AAT GAA GAT GTG CGC TGT AAG CAG TGC GCT CGG GGT ACC TTC TCT GAC      288
Asn Glu Asp Val Arg Cys Lys Gln Cys Ala Arg Gly Thr Phe Ser Asp
                 85                  90                  95

GTG CCT TCC AGT GTG ATG AAG TGT AAA GCT CAC ACG GAC TGT CTG GGT      336
Val Pro Ser Ser Val Met Lys Cys Lys Ala His Thr Asp Cys Leu Gly
            100                 105                 110

CAG AAC CTG GAG GTG GTC AAG CCA GGG ACC AAG GAG ACA GAC AAC GTC      384
Gln Asn Leu Glu Val Val Lys Pro Gly Thr Lys Glu Thr Asp Asn Val
        115                 120                 125

TGT GGC ATG CGC CTG TTC TTC TCC AGC ACA AAC CCA CCT TCC TCT GGC      432
Cys Gly Met Arg Leu Phe Phe Ser Ser Thr Asn Pro Pro Ser Ser Gly
    130                 135                 140

ACA GTT ACC TTT TCT CAC CCT GAG CAT ATG GAA TCC CAC GAT GTC CCT      480
Thr Val Thr Phe Ser His Pro Glu His Met Glu Ser His Asp Val Pro
145                 150                 155                 160

TCC TCC ACC TAT GAG CCC CAA GGC ATG AAC TCA ACA GAT TCC AAC TCT      528
Ser Ser Thr Tyr Glu Pro Gln Gly Met Asn Ser Thr Asp Ser Asn Ser
                165                 170                 175

ACT GCC TCT GTT AGA ACT AAG GTA CCA AGT GGC ATC GAG GAA GGG ACA      576
Thr Ala Ser Val Arg Thr Lys Val Pro Ser Gly Ile Glu Glu Gly Thr
            180                 185                 190
```

-continued

```
GTG CCT GAC AAT ACG AGC TCA ACC AGT GGG AAG GAA GGC ACT AAT AGG      624
Val Pro Asp Asn Thr Ser Ser Thr Ser Gly Lys Glu Gly Thr Asn Arg
        195                 200                 205

ACC CTG CCA AAC CCA CCA CAA GTT ACC CAC CAG CAA GCC CCC CAC CAC      672
Thr Leu Pro Asn Pro Pro Gln Val Thr His Gln Gln Ala Pro His His
    210                 215                 220

AGA CAC ATT CTG AAG CTG CTG CCA TCG TCC ATG GAG GCC ACG GGT GAG      720
Arg His Ile Leu Lys Leu Leu Pro Ser Ser Met Glu Ala Thr Gly Glu
225                 230                 235                 240

AAG TCC AGC ACA GCC ATC AAG GCC CCC AAG AGG GGT CAC CCC AGA CAG      768
Lys Ser Ser Thr Ala Ile Lys Ala Pro Lys Arg Gly His Pro Arg Gln
                245                 250                 255

AAC GCT CAC AAG CAT TTC GAC ATC AAC GAG CAC TTG CCT TGG ATG ATC      816
Asn Ala His Lys His Phe Asp Ile Asn Glu His Leu Pro Trp Met Ile
            260                 265                 270

GTC CTC TTC CTT CTG CTG GTC CTG GTG CTG ATA GTG GTG TGC AGT ATC      864
Val Leu Phe Leu Leu Leu Val Leu Val Leu Ile Val Val Cys Ser Ile
        275                 280                 285

CGA AAG AGC TCC AGG ACT CTC AAA AAG GGG CCC CGG CAG GAT CCC AGC      912
Arg Lys Ser Ser Arg Thr Leu Lys Lys Gly Pro Arg Gln Asp Pro Ser
    290                 295                 300

GCC ATA GTG GAA AAG GCG GGG CTG AAG AAG TCC CTG ACT CCC ACC CAG      960
Ala Ile Val Glu Lys Ala Gly Leu Lys Lys Ser Leu Thr Pro Thr Gln
305                 310                 315                 320

AAC CGG GAG AAA TGG ATC TAC TAC CGC AAC GGC CAT GGT ATT GAC ATC     1008
Asn Arg Glu Lys Trp Ile Tyr Tyr Arg Asn Gly His Gly Ile Asp Ile
                325                 330                 335

TTG AAG CTT GTA GCA GCC CAG GTG GGA AGC CAG TGG AAG GAC ATC TAT     1056
Leu Lys Leu Val Ala Ala Gln Val Gly Ser Gln Trp Lys Asp Ile Tyr
            340                 345                 350

CAG TTT CTT TGC AAC GCC AGT GAG AGG GAG GTG GCG GCC TTC TCC AAT     1104
Gln Phe Leu Cys Asn Ala Ser Glu Arg Glu Val Ala Ala Phe Ser Asn
        355                 360                 365

GGA TAC ACT GCA GAT CAT GAA CGG GCC TAC GCG GCT CTG CAG CAC TGG     1152
Gly Tyr Thr Ala Asp His Glu Arg Ala Tyr Ala Ala Leu Gln His Trp
    370                 375                 380

ACC ATC CGT GGC CCT GAG GCC AGC CTT GCC CAG CTC ATT AGC GCC TTG     1200
Thr Ile Arg Gly Pro Glu Ala Ser Leu Ala Gln Leu Ile Ser Ala Leu
385                 390                 395                 400

CGC CAG CAC CGA CGC AAT GAT GTT GTG GAG AAG ATT CGT GGG CTG ATG     1248
Arg Gln His Arg Arg Asn Asp Val Val Glu Lys Ile Arg Gly Leu Met
                405                 410                 415

GAA GAC ACC ACG CAG TTG GAA ACA GAC AAA CTG GCT CTC CCC ATG AGC     1296
Glu Asp Thr Thr Gln Leu Glu Thr Asp Lys Leu Ala Leu Pro Met Ser
            420                 425                 430

CCC AGT CCG CTG AGC CCG AGC CCC ATC CCC AGT CCT AAC GTG AAA CTT     1344
Pro Ser Pro Leu Ser Pro Ser Pro Ile Pro Ser Pro Asn Val Lys Leu
        435                 440                 445

GAG AAT TCC ACT CTC CTG ACA GTG GAG CCC TCA CCG CTG GAC AAG AAC     1392
Glu Asn Ser Thr Leu Leu Thr Val Glu Pro Ser Pro Leu Asp Lys Asn
    450                 455                 460

AAG TGC TTC TTC GTG GAC GAG TCA GAG CCC CTT CTG CGT TGC GAC TCC     1440
Lys Cys Phe Phe Val Asp Glu Ser Glu Pro Leu Leu Arg Cys Asp Ser
465                 470                 475                 480

ACA TCC AGT GGC TCT TCA GCA CTG AGC AGA AAC GGC TCC TTT ATT ACC     1488
Thr Ser Ser Gly Ser Ser Ala Leu Ser Arg Asn Gly Ser Phe Ile Thr
                485                 490                 495
```

-continued

```
AAA GAA AAG AAG GAC ACA GTG TTG CGG CAG GTC CGC CTG GAC CCC TGT     1536
Lys Glu Lys Lys Asp Thr Val Leu Arg Gln Val Arg Leu Asp Pro Cys
            500                 505                 510

GAC TTG CAG CCC ATC TTT GAT GAC ATG CTG CAT ATC CTG AAC CCC GAG     1584
Asp Leu Gln Pro Ile Phe Asp Asp Met Leu His Ile Leu Asn Pro Glu
        515                 520                 525

GAG CTG CGG GTG ATT GAA GAG ATT CCC CAG GCT GAG GAC AAA CTG GAC     1632
Glu Leu Arg Val Ile Glu Glu Ile Pro Gln Ala Glu Asp Lys Leu Asp
    530                 535                 540

CGC CTC TTC GAG ATC ATT GGG GTC AAG AGC CAA GAA GCC AGC CAG ACC     1680
Arg Leu Phe Glu Ile Ile Gly Val Lys Ser Gln Glu Ala Ser Gln Thr
545                 550                 555                 560

CTC TTG GAC TCT GTG TAC AGT CAT CTT CCT GAC CTA TTG                 1719
Leu Leu Asp Ser Val Tyr Ser His Leu Pro Asp Leu Leu
                565                 570
```

(2) INFORMATION FOR SEQ ID NO:6:

(i) SEQUENCE CHARACTERISTICS:
(A) LENGTH: 759 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..759

(xi) SEQUENCE DESCRIPTION: SEQ ID NO:6:

```
ATG GGG ACC TCT CCG AGC AGC AGC ACC GCC CTC GCC TCC TGC AGC CGC       48
Met Gly Thr Ser Pro Ser Ser Ser Thr Ala Leu Ala Ser Cys Ser Arg
  1               5                  10                  15

ATC GCC CGC CGA GCC ACA GCC ACG ATG ATC GCG GGC TCC CTT CTC CTG       96
Ile Ala Arg Arg Ala Thr Ala Thr Met Ile Ala Gly Ser Leu Leu Leu
             20                  25                  30

CTT GGA TTC CTT AGC ACC ACC ACA GCT CAG CCA GAA CAG AAG GCC TCG      144
Leu Gly Phe Leu Ser Thr Thr Thr Ala Gln Pro Glu Gln Lys Ala Ser
         35                  40                  45

AAT CTC ATT GGC ACA TAC CGC CAT GTT GAC CGT GCC ACC GGC CAG GTG      192
Asn Leu Ile Gly Thr Tyr Arg His Val Asp Arg Ala Thr Gly Gln Val
     50                  55                  60

CTA ACC TGT GAC AAG TGT CCA GCA GGA ACC TAT GTC TCT GAG CAT TGT      240
Leu Thr Cys Asp Lys Cys Pro Ala Gly Thr Tyr Val Ser Glu His Cys
 65                  70                  75                  80

ACC AAC ACA AGC CTG CGC GTC TGC AGC AGT TGC CCT GTG GGG ACC TTT      288
Thr Asn Thr Ser Leu Arg Val Cys Ser Ser Cys Pro Val Gly Thr Phe
                 85                  90                  95

ACC AGG CAT GAG AAT GGC ATA GAG AAA TGC CAT GAC TGT AGT CAG CCA      336
Thr Arg His Glu Asn Gly Ile Glu Lys Cys His Asp Cys Ser Gln Pro
            100                 105                 110

TGC CCA TGG CCA ATG ATT GAG AAA TTA CCT TGT GCT GCC TTG ACT GAC      384
Cys Pro Trp Pro Met Ile Glu Lys Leu Pro Cys Ala Ala Leu Thr Asp
        115                 120                 125

CGA GAA TGC ACT TGC CCA CCT GGC ATG TTC CAG TCT AAC GCT ACC TGT      432
Arg Glu Cys Thr Cys Pro Pro Gly Met Phe Gln Ser Asn Ala Thr Cys
    130                 135                 140

GCC CCC CAT ACG GTG TGT CCT GTG GGT TGG GGT GTG CGG AAG AAA GGG      480
Ala Pro His Thr Val Cys Pro Val Gly Trp Gly Val Arg Lys Lys Gly
145                 150                 155                 160
```

-continued

```
ACA GAG ACT GAG GAT GTG CGG TGT AAG CAG TGT GCT CGG GGT ACC TTC       528
Thr Glu Thr Glu Asp Val Arg Cys Lys Gln Cys Ala Arg Gly Thr Phe
                165                 170                 175

TCA GAT GTG CCT TCT AGT GTG ATG AAA TGC AAA GCA TAC ACA GAC TGT       576
Ser Asp Val Pro Ser Ser Val Met Lys Cys Lys Ala Tyr Thr Asp Cys
            180                 185                 190

CTG AGT CAG AAC CTG GTG GTG ATC AAG CCG GGG ACC AAG GAG ACA GAC       624
Leu Ser Gln Asn Leu Val Val Ile Lys Pro Gly Thr Lys Glu Thr Asp
        195                 200                 205

AAC GTC TGT GGC ACA CTC CCG TCC TTC TCC AGC TCC ACC TCA CCT TCC       672
Asn Val Cys Gly Thr Leu Pro Ser Phe Ser Ser Ser Thr Ser Pro Ser
    210                 215                 220

CCT GGC ACA GCC ATC TTT CCA CGC CCT GAG CAC ATG GAA ACC CAT GAA       720
Pro Gly Thr Ala Ile Phe Pro Arg Pro Glu His Met Glu Thr His Glu
225                 230                 235                 240

GTC CCT TCC TCC ACT TAT GTT CCC AAA GAC CAA AGG TAC                   759
Val Pro Ser Ser Thr Tyr Val Pro Lys Asp Gln Arg Tyr
                245                 250
```

(2) INFORMATION FOR SEQ ID NO:7:

(i) SEQUENCE CHARACTERISTICS:
(A) LENGTH: 461 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:7:

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220
```

```
Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460
```

(2) INFORMATION FOR SEQ ID NO:8:

(i) SEQUENCE CHARACTERISTICS:
(A) LENGTH: 474 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:8:

```
Met Ala Pro Ala Ala Leu Trp Val Ala Leu Val Phe Glu Leu Gln Leu
1               5                   10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
        35                  40                  45

Arg Lys Ala Gln Met Cys Cys Ala Lys Cys Pro Pro Gly Gln Tyr Val
    50                  55                  60

Lys His Phe Cys Asn Lys Thr Ser Asp Thr Val Cys Ala Asp Cys Glu
65                  70                  75                  80

Ala Ser Met Tyr Thr Gln Val Trp Asn Gln Phe Arg Thr Cys Leu Ser
                85                  90                  95
```

-continued

```
Cys Ser Ser Ser Cys Thr Thr Asp Gln Val Glu Ile Arg Ala Cys Thr
            100                 105                 110

Lys Gln Gln Asn Arg Val Cys Ala Cys Glu Ala Gly Arg Tyr Cys Ala
        115                 120                 125

Leu Lys Thr His Ser Gly Ser Cys Arg Gln Cys Met Arg Leu Ser Lys
    130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Pro Glu Ser Pro Thr
        195                 200                 205

Leu Ser Ala Ile Pro Arg Thr Leu Tyr Val Ser Gln Pro Glu Pro Thr
    210                 215                 220

Arg Ser Gln Pro Leu Asp Gln Glu Pro Gly Pro Ser Gln Thr Pro Ser
225                 230                 235                 240

Ile Leu Thr Ser Leu Gly Ser Thr Pro Ile Ile Glu Gln Ser Thr Lys
                245                 250                 255

Gly Gly Ile Ser Leu Pro Ile Gly Leu Ile Val Gly Val Thr Ser Leu
            260                 265                 270

Gly Leu Leu Met Leu Gly Leu Val Asn Cys Ile Ile Leu Val Gln Arg
        275                 280                 285

Lys Lys Lys Pro Ser Cys Leu Gln Arg Asp Ala Lys Val Pro His Val
    290                 295                 300

Pro Asp Glu Lys Ser Gln Asp Ala Val Gly Leu Glu Gln Gln His Leu
305                 310                 315                 320

Leu Thr Thr Ala Pro Ser Ser Ser Ser Ser Ser Leu Glu Ser Ser Ala
                325                 330                 335

Ser Ala Gly Asp Arg Arg Ala Pro Pro Gly Gly His Pro Gln Ala Arg
            340                 345                 350

Val Met Ala Glu Ala Gln Gly Phe Gln Glu Ala Arg Ala Ser Ser Arg
        355                 360                 365

Ile Ser Asp Ser Ser His Gly Ser His Gly Thr His Val Asn Val Thr
    370                 375                 380

Cys Ile Val Asn Val Cys Ser Ser Ser Asp His Ser Ser Gln Cys Ser
385                 390                 395                 400

Ser Gln Ala Ser Ala Thr Val Gly Asp Pro Asp Ala Lys Pro Ser Ala
                405                 410                 415

Ser Pro Lys Asp Glu Gln Val Pro Phe Ser Gln Glu Glu Cys Pro Ser
            420                 425                 430

Gln Ser Pro Cys Glu Thr Thr Glu Thr Leu Gln Ser His Glu Lys Pro
        435                 440                 445

Leu Pro Leu Gly Val Pro Asp Met Gly Met Lys Pro Ser Gln Ala Gly
    450                 455                 460

Trp Phe Asp Gln Ile Ala Val Lys Val Ala
465                 470
```

(2) INFORMATION FOR SEQ ID NO:9:

(i) SEQUENCE CHARACTERISTICS:
(A) LENGTH: 325 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:9:

```
Met Leu Arg Leu Ile Ala Leu Leu Val Cys Val Val Tyr Val Tyr Gly
1               5                   10                  15

Asp Asp Val Pro Tyr Ser Ser Asn Gln Gly Lys Cys Gly Gly His Asp
            20                  25                  30

Tyr Glu Lys Asp Gly Leu Cys Cys Ala Ser Cys His Pro Gly Phe Tyr
        35                  40                  45

Ala Ser Arg Leu Cys Gly Pro Gly Ser Asn Thr Val Cys Ser Pro Cys
    50                  55                  60

Glu Asp Gly Thr Phe Thr Ala Ser Thr Asn His Ala Pro Ala Cys Val
65                  70                  75                  80

Ser Cys Arg Gly Pro Cys Thr Gly His Leu Ser Glu Ser Gln Pro Cys
                85                  90                  95

Asp Arg Thr His Asp Arg Val Cys Asn Cys Ser Thr Gly Asn Tyr Cys
            100                 105                 110

Leu Leu Lys Gly Gln Asn Gly Cys Arg Ile Cys Ala Pro Gln Thr Lys
        115                 120                 125

Cys Pro Ala Gly Tyr Gly Val Ser Gly His Thr Arg Ala Gly Asp Thr
    130                 135                 140

Leu Cys Glu Lys Cys Pro Pro His Thr Tyr Ser Asp Ser Leu Ser Pro
145                 150                 155                 160

Thr Glu Arg Cys Gly Thr Ser Phe Asn Tyr Ile Ser Val Gly Phe Asn
                165                 170                 175

Leu Tyr Pro Val Asn Glu Thr Ser Cys Thr Thr Thr Ala Gly His Asn
            180                 185                 190

Glu Val Ile Lys Thr Lys Glu Phe Thr Val Thr Leu Asn Tyr Thr Asp
        195                 200                 205

Cys Asp Pro Val Phe His Thr Glu Tyr Tyr Ala Thr Ser Gly Lys Glu
    210                 215                 220

Gly Ala Gly Gly Phe Phe Thr Gly Thr Asp Ile Tyr Gln Asn Thr Thr
225                 230                 235                 240

Lys Val Cys Thr Leu Asn Val Glu Ile Gln Cys Ser Glu Gly Asp Asp
                245                 250                 255

Ile His Thr Leu Gln Lys Thr Asn Gly Gly Ser Thr Met Pro His Ser
            260                 265                 270

Glu Thr Ile Thr Val Val Gly Ser Cys Leu Ser Asp Val Asn Val Asp
        275                 280                 285

Ile Met Tyr Ser Asp Thr Asn His Pro Gly Glu Val Asp Asp Phe Val
    290                 295                 300

Glu Tyr His Trp Gly Thr Arg Leu Arg Phe Phe Pro Leu Pro Lys Arg
305                 310                 315                 320

Cys Thr Pro Val Ser
                325
```

(2) INFORMATION FOR SEQ ID NO:10:

(i) SEQUENCE CHARACTERISTICS:
(A) LENGTH: 277 amino acids
(B) TYPE: amino acid
(D) TOPOLOGY: linear (ii) MOLECULE TYPE: peptide -continued (v) FRAGMENT TYPE: internal (xi) SEQUENCE DESCRIPTION: SEQ ID NO:10:

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275
```

(2) INFORMATION FOR SEQ ID NO:11:

(i) SEQUENCE CHARACTERISTICS:
(A) LENGTH: 289 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:11:

```
Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30
```

-continued

```
His Asp Gly Gln Cys Cys Asp Leu Cys Gln Pro Gly Ser Arg Leu Thr
        35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
        115                 120                 125

Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val Ile Pro Val Val Met Gly Ile Leu Ile Thr Ile
        195                 200                 205

Phe Gly Val Phe Leu Tyr Ile Lys Lys Val Val Lys Lys Pro Lys Asp
    210                 215                 220

Asn Glu Met Leu Pro Pro Ala Ala Arg Arg Gln Asp Pro Gln Glu Met
225                 230                 235                 240

Glu Asp Tyr Pro Gly His Asn Thr Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln Val Thr Asp Ser Ile Ala Leu Arg Pro Leu
        275                 280                 285

Val
```

(2) INFORMATION FOR SEQ ID NO:12:

(i) SEQUENCE CHARACTERISTICS:
(A) LENGTH: 401 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:12:

```
Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80
```

-continued

```
Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Ala Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
    370                 375                 380

Phe Leu Glu Met Ile Gly Asn Gln Val Gln Ser Val Lys Ile Ser Cys
385                 390                 395                 400

Leu
```

(2) INFORMATION FOR SEQ ID NO:13:

(i) SEQUENCE CHARACTERISTICS:
(A) LENGTH: 401 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:13:

```
Met Asn Lys Trp Leu Cys Cys Ala Leu Leu Val Leu Leu Asp Ile Ile
1               5                   10                  15
```

-continued

```
Glu Trp Thr Thr Gln Glu Thr Leu Pro Pro Lys Tyr Leu His Tyr Asp
            20                  25                  30

Pro Glu Thr Gly His Gln Leu Leu Cys Asp Lys Cys Ala Pro Gly Thr
        35                  40                  45

Tyr Leu Lys Gln His Cys Thr Val Arg Arg Lys Thr Leu Cys Val Pro
    50                  55                  60

Cys Pro Asp His Ser Tyr Thr Asp Ser Trp His Thr Ser Asp Glu Cys
65                  70                  75                  80

Val Tyr Cys Ser Pro Val Cys Lys Glu Leu Gln Ser Val Lys Gln Glu
                85                  90                  95

Cys Asn Arg Thr His Asn Arg Val Cys Glu Cys Glu Glu Gly Arg Tyr
            100                 105                 110

Leu Glu Ile Glu Phe Cys Leu Lys His Arg Ser Cys Pro Pro Gly Ser
        115                 120                 125

Gly Val Val Gln Ala Gly Thr Pro Glu Arg Asn Thr Val Cys Lys Lys
    130                 135                 140

Cys Pro Asp Gly Phe Phe Ser Gly Glu Thr Ser Ser Lys Ala Pro Cys
145                 150                 155                 160

Ile Lys His Thr Asn Cys Ser Thr Phe Gly Leu Leu Leu Ile Gln Lys
                165                 170                 175

Gly Asn Ala Thr His Asp Asn Val Cys Ser Gly Asn Arg Glu Ala Thr
            180                 185                 190

Gln Lys Cys Gly Ile Asp Val Thr Leu Cys Glu Glu Ala Phe Phe Arg
        195                 200                 205

Phe Ala Val Pro Thr Lys Ile Ile Pro Asn Trp Leu Ser Val Leu Val
    210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
                245                 250                 255

Trp Lys His Gln Asn Arg Asp Gln Glu Met Val Lys Lys Ile Ile Gln
            260                 265                 270

Asp Ile Asp Leu Cys Glu Ser Ser Val Gln Arg His Leu Gly His Ser
        275                 280                 285

Asn Leu Thr Thr Glu Gln Leu Leu Ala Leu Met Glu Ser Leu Pro Gly
    290                 295                 300

Lys Lys Ile Ser Pro Glu Glu Ile Glu Arg Thr Arg Lys Thr Cys Lys
305                 310                 315                 320

Ser Ser Glu Gln Leu Leu Lys Leu Leu Ser Leu Trp Arg Ile Lys Asn
                325                 330                 335

Gly Asp Gln Asp Thr Leu Lys Gly Leu Met Tyr Ala Leu Lys His Leu
            340                 345                 350

Lys Thr Ser His Phe Pro Lys Thr Val Thr His Ser Leu Arg Lys Thr
        355                 360                 365

Met Arg Phe Leu His Ser Phe Thr Met Tyr Arg Leu Tyr Gln Lys Leu
    370                 375                 380

Phe Leu Glu Met Ile Gly Asn Gln Val Gln Ser Val Lys Ile Ser Cys
385                 390                 395                 400

Leu
```

-continued (2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:14:

TCCCTGACAA CACAAGCTCA 20

(2) INFORMATION FOR SEQ ID NO:15:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

TCCATTTCTC CCGGTTCTG 19

(2) INFORMATION FOR SEQ ID NO:16:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

CCATGTTGAC CGTACCAC 18

(2) INFORMATION FOR SEQ ID NO:17:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

GCACTCTCGG TCAGTCAA 18

(2) INFORMATION FOR SEQ ID NO:18:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:18:

TTTTGAATTC CAGCCAGAAC AGAAGGCCTC GA 32

(2) INFORMATION FOR SEQ ID NO:19:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:19:

TTTTTCTAGA TACCTTTGGT CTTTGGGAAC 30

(2) INFORMATION FOR SEQ ID NO:20:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:20:

AAAAAAGAAT TCGCCGCCAT GGGGACCTCT 30

(2) INFORMATION FOR SEQ ID NO:21:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: peptide (xi) SEQUENCE DESCRIPTION: SEQ ID NO:21:

CTTGTCGTCG TCGTCCTTGT AGTCGTACCT TTG 33

(2) INFORMATION FOR SEQ ID NO:22:

(i) SEQUENCE CHARACTERISTICS:
(A) LENGTH: 2638 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 510..2327

(xi) SEQUENCE DESCRIPTION: SEQ ID NO:22:

CGGGTCACGT TTGCGGGTAC CCACCCACAC CCGCCGCGCT TAATGCGCCG CTACAGGGCG 60

CGTCCCATTC GCCATTCAGG CTGCGCAACT GTTGGAAGGG CGATCGGGTG CGGGCCTCTT 120

CGCTATTACG CCAAGCTGGC GAAAGGGGGA TGTGCTGCAA GGCGATTAAG TTGGGTAACG 180

CCAAGGGTTT TCCCAGTCAC GACGGTTGTA AAACGACGGC CAGTGAATTG AATTTAGGTG 240

ACACTATAGA AGAGCTATGA CGTCGCATGC ACGCGTACGT AAGCTTGGAT CCTCTAGAGC 300

GGCCGCGCCG CTGGGCAGGT GCTGAGCGCC CCTAGAGCCT CCCTTGCCGC CTCCCTCCTC 360

TGCCCGGCCG CAGCAGTGCA CATGGGGTGT TGGAGGTAGA TGGGCTCCCG GCCCGGGAGG 420

CGGCGGTGGA TGCGGCGCTG GGCAGAAGCA GCCGCCGATT CCAGCTGCCC CGCGCGCCCC 480

-continued

```
GGGCGCCCCT GCGAGTCCCC GGTTCAGCC ATG GGG ACC TCT CCG AGC AGC AGC      533
                                Met Gly Thr Ser Pro Ser Ser Ser
                                  1               5

ACC GCC CTC GCC TCC TGC AGC CGC ATC GCC CGC CGA GCC ACA GCC ACG      581
Thr Ala Leu Ala Ser Cys Ser Arg Ile Ala Arg Arg Ala Thr Ala Thr
     10                  15                  20

ATG ATC GCG GGC TCC CTT CTC CTG CTT GGA TTC CTT AGC ACC ACC ACA      629
Met Ile Ala Gly Ser Leu Leu Leu Leu Gly Phe Leu Ser Thr Thr Thr
 25                  30                  35                  40

GCT CAG CCA GAA CAG AAG GCC TCG AAT CTC ATT GGC ACA TAC CGC CAT      677
Ala Gln Pro Glu Gln Lys Ala Ser Asn Leu Ile Gly Thr Tyr Arg His
                 45                  50                  55

GTT GAC CGT GCC ACC GGC CAG GTG CTA ACC TGT GAC AAG TGT CCA GCA      725
Val Asp Arg Ala Thr Gly Gln Val Leu Thr Cys Asp Lys Cys Pro Ala
             60                  65                  70

GGA ACC TAT GTC TCT GAG CAT TGT ACC AAC ACA AGC CTG CGC GTC TGC      773
Gly Thr Tyr Val Ser Glu His Cys Thr Asn Thr Ser Leu Arg Val Cys
         75                  80                  85

AGC AGT TGC CCT GTG GGG ACC TTT ACC AGG CAT GAG AAT GGC ATA GAG      821
Ser Ser Cys Pro Val Gly Thr Phe Thr Arg His Glu Asn Gly Ile Glu
     90                  95                 100

AAA TGC CAT GAC TGT AGT CAG CCA TGC CCA TGG CCA ATG ATT GAG AAA      869
Lys Cys His Asp Cys Ser Gln Pro Cys Pro Trp Pro Met Ile Glu Lys
105                 110                 115                 120

TTA CCT TGT GCT GCC TTG ACT GAC CGA GAA TGC ACT TGC CCA CCT GGC      917
Leu Pro Cys Ala Ala Leu Thr Asp Arg Glu Cys Thr Cys Pro Pro Gly
                125                 130                 135

ATG TTC CAG TCT AAC GCT ACC TGT GCC CCC CAT ACG GTG TGT CCT GTG      965
Met Phe Gln Ser Asn Ala Thr Cys Ala Pro His Thr Val Cys Pro Val
            140                 145                 150

GGT TGG GGT GTG CGG AAG AAA GGG ACA GAG ACT GAG GAT GTG CGG TGT     1013
Gly Trp Gly Val Arg Lys Lys Gly Thr Glu Thr Glu Asp Val Arg Cys
        155                 160                 165

AAG CAG TGT GCT CGG GGT ACC TTC TCA GAT GTG CCT TCT AGT GTG ATG     1061
Lys Gln Cys Ala Arg Gly Thr Phe Ser Asp Val Pro Ser Ser Val Met
    170                 175                 180

AAA TGC AAA GCA TAC ACA GAC TGT CTG AGT CAG AAC CTG GTG GTG ATC     1109
Lys Cys Lys Ala Tyr Thr Asp Cys Leu Ser Gln Asn Leu Val Val Ile
185                 190                 195                 200

AAG CCG GGG ACC AAG GAG ACA GAC AAC GTC TGT GGC ACA CTC CCG TCC     1157
Lys Pro Gly Thr Lys Glu Thr Asp Asn Val Cys Gly Thr Leu Pro Ser
                205                 210                 215

TTC TCC AGC TCC ACC TCA CCT TCC CCT GGC ACA GCC ATC TTT CCA CGC     1205
Phe Ser Ser Ser Thr Ser Pro Ser Pro Gly Thr Ala Ile Phe Pro Arg
            220                 225                 230

CCT GAG CAC ATG GAA ACC CAT GAA GTC CCT TCC TCC ACT TAT GTT CCC     1253
Pro Glu His Met Glu Thr His Glu Val Pro Ser Ser Thr Tyr Val Pro
        235                 240                 245

AAA GGC ATG AAC TCA ACA GAA TCC AAC TCT TCT GCC TCT GTT AGA CCA     1301
Lys Gly Met Asn Ser Thr Glu Ser Asn Ser Ser Ala Ser Val Arg Pro
    250                 255                 260

AAG GTA CTG AGT AGC ATC CAG GAA GGG ACA GTC CCT GAC AAC ACA AGC     1349
Lys Val Leu Ser Ser Ile Gln Glu Gly Thr Val Pro Asp Asn Thr Ser
265                 270                 275                 280

TCA GCA AGG GGG AAG GAA GAC GTG AAC AAG ACC CTC CCA AAC CTT CAG     1397
Ser Ala Arg Gly Lys Glu Asp Val Asn Lys Thr Leu Pro Asn Leu Gln
                285                 290                 295

GTA GTC AAC CAC CAG CAA GGC CCC CAC CAC AGA CAC ATC CTG AAG CTG     1445
Val Val Asn His Gln Gln Gly Pro His His Arg His Ile Leu Lys Leu
            300                 305                 310
```

-continued

```
CTG CCG TCC ATG GAG GCC ACT GGG GGC GAG AAG TCC AGC ACG CCC ATC     1493
Leu Pro Ser Met Glu Ala Thr Gly Gly Glu Lys Ser Ser Thr Pro Ile
        315                 320                 325

AAG GGC CCC AAG AGG GGA CAT CCT AGA CAG AAC CTA CAC AAG CAT TTT     1541
Lys Gly Pro Lys Arg Gly His Pro Arg Gln Asn Leu His Lys His Phe
    330                 335                 340

GAC ATC AAT GAG CAT TTG CCC TGG ATG ATT GTG CTT TTC CTG CTG CTG     1589
Asp Ile Asn Glu His Leu Pro Trp Met Ile Val Leu Phe Leu Leu Leu
345                 350                 355                 360

GTG CTT GTG GTG ATT GTG GTG TGC AGT ATC CGG AAA AGC TCG AGG ACT     1637
Val Leu Val Val Ile Val Val Cys Ser Ile Arg Lys Ser Ser Arg Thr
                365                 370                 375

CTG AAA AAG GGG CCC CGG CAG GAT CCC AGT GCC ATT GTG GAA AAG GCA     1685
Leu Lys Lys Gly Pro Arg Gln Asp Pro Ser Ala Ile Val Glu Lys Ala
            380                 385                 390

GGG CTG AAG AAA TCC ATG ACT CCA ACC CAG AAC CGG GAG AAA TGG ATC     1733
Gly Leu Lys Lys Ser Met Thr Pro Thr Gln Asn Arg Glu Lys Trp Ile
        395                 400                 405

TAC TAC TGC AAT GGC CAT GGT ATC GAT ATC CTG AAG CTT GTA GCA GCC     1781
Tyr Tyr Cys Asn Gly His Gly Ile Asp Ile Leu Lys Leu Val Ala Ala
    410                 415                 420

CAA GTG GGA AGC CAG TGG AAA GAT ATC TAT CAG TTT CTT TGC AAT GCC     1829
Gln Val Gly Ser Gln Trp Lys Asp Ile Tyr Gln Phe Leu Cys Asn Ala
425                 430                 435                 440

AGT GAG AGG GAG GTT GCT GCT TTC TCC AAT GGG TAC ACA GCC GAC CAC     1877
Ser Glu Arg Glu Val Ala Ala Phe Ser Asn Gly Tyr Thr Ala Asp His
                445                 450                 455

GAG CGG GCC TAC GCA GCT CTG CAG CAC TGG ACC ATC CGG GGC CCC GAG     1925
Glu Arg Ala Tyr Ala Ala Leu Gln His Trp Thr Ile Arg Gly Pro Glu
            460                 465                 470

GCC AGC CTC GCC CAG CTA ATT AGC GCC CTG CGC CAG CAC CGG AGA AAC     1973
Ala Ser Leu Ala Gln Leu Ile Ser Ala Leu Arg Gln His Arg Arg Asn
        475                 480                 485

GAT GTT GTG GAG AAG ATT CGT GGG CTG ATG GAA GAC ACC ACC CAG CTG     2021
Asp Val Val Glu Lys Ile Arg Gly Leu Met Glu Asp Thr Thr Gln Leu
    490                 495                 500

GAA ACT GAC AAA CTA GCT CTC CCG ATG AGC CCC AGC CCG CTT AGC CCG     2069
Glu Thr Asp Lys Leu Ala Leu Pro Met Ser Pro Ser Pro Leu Ser Pro
505                 510                 515                 520

AGC CCC ATC CCC AGC CCC AAC GCG AAA CTT GAG AAT TCC GCT CTC CTG     2117
Ser Pro Ile Pro Ser Pro Asn Ala Lys Leu Glu Asn Ser Ala Leu Leu
                525                 530                 535

ACG GTG GAG CCT TCC CCA CAG GAT TTG CTA TTT AAG TGG CTT GAC AAC     2165
Thr Val Glu Pro Ser Pro Gln Asp Leu Leu Phe Lys Trp Leu Asp Asn
            540                 545                 550

TGG GCC ACC AAA GAA CTT GAA CTT CAC CTT TTA GGA TTT GAG CTG TTC     2213
Trp Ala Thr Lys Glu Leu Glu Leu His Leu Leu Gly Phe Glu Leu Phe
        555                 560                 565

TGG AAC ACA TTG CTG CAC TTT GGA AAG TCA AAA TCA AGT GCC AGT GGC     2261
Trp Asn Thr Leu Leu His Phe Gly Lys Ser Lys Ser Ser Ala Ser Gly
    570                 575                 580

GCC CTT TCC ATA GAG AAT TTG CCC AGC TTT GCT TTA AAA GAT GTC TTG     2309
Ala Leu Ser Ile Glu Asn Leu Pro Ser Phe Ala Leu Lys Asp Val Leu
585                 590                 595                 600

TTT TTT ATA TAC ACA TAATCAATAG GTCCAATCTG CTCTCAAGGC CTTGGTCCTG     2364
Phe Phe Ile Tyr Thr
                605
```

-continued

```
GTGGGATTCC TTCACCAATT ACTTTAATTA AAAATGGCTG CAACTGTAAG AACCCTTGTC   2424

TGATATATTT GCAACTATGC TCCCATTTAC AAATGTACCT TCTAATGCTC AGTTGCCAGG   2484

TTCCAATGCA AAGGTGGCGT GGACTCCCTT TGTGTGGGTG GGGTTTGTGG GTAGTGGTGA   2544

AGGACCGATA TCAGAAAAAT GCCTTCAAGT GTACTAATTT ATTAATAAAC ATTAGGTGTT   2604

TGTTACTTAA AAAAAAAAAA AAAAGGGCGG CCGC                               2638
```

(2) INFORMATION FOR SEQ ID NO:23:

(i) SEQUENCE CHARACTERISTICS:
(A) LENGTH: 605 amino acids
(B) TYPE: amino acid
(D) TOPOLOGY: linear (ii) MOLECULE TYPE: protein (xi) SEQUENCE DESCRIPTION: SEQ ID NO:23:

```
Met Gly Thr Ser Pro Ser Ser Ser Thr Ala Leu Ala Ser Cys Ser Arg
  1               5                  10                  15

Ile Ala Arg Arg Ala Thr Ala Thr Met Ile Ala Gly Ser Leu Leu Leu
             20                  25                  30

Leu Gly Phe Leu Ser Thr Thr Thr Ala Gln Pro Glu Gln Lys Ala Ser
         35                  40                  45

Asn Leu Ile Gly Thr Tyr Arg His Val Asp Arg Ala Thr Gly Gln Val
     50                  55                  60

Leu Thr Cys Asp Lys Cys Pro Ala Gly Thr Tyr Val Ser Glu His Cys
 65                  70                  75                  80

Thr Asn Thr Ser Leu Arg Val Cys Ser Ser Cys Pro Val Gly Thr Phe
                 85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
        115                 120                 125

Arg Glu Cys Thr Cys Pro Pro Gly Met Phe Gln Ser Asn Ala Thr Cys
    130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
        195                 200                 205

Asn Val Cys Gly Thr Leu Pro Ser Phe Ser Ser Ser Thr Ser Pro Ser
    210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Gly Met Asn Ser Thr Glu Ser
                245                 250                 255

Asn Ser Ser Ala Ser Val Arg Pro Lys Val Leu Ser Ser Ile Gln Glu
            260                 265                 270

Gly Thr Val Pro Asp Asn Thr Ser Ser Ala Arg Gly Lys Glu Asp Val
        275                 280                 285

Asn Lys Thr Leu Pro Asn Leu Gln Val Val Asn His Gln Gln Gly Pro
    290                 295                 300
```

-continued

```
His His Arg His Ile Leu Lys Leu Leu Pro Ser Met Glu Ala Thr Gly
305                 310                 315                 320

Gly Glu Lys Ser Ser Thr Pro Ile Lys Gly Pro Lys Arg Gly His Pro
                325                 330                 335

Arg Gln Asn Leu His Lys His Phe Asp Ile Asn Glu His Leu Pro Trp
            340                 345                 350

Met Ile Val Leu Phe Leu Leu Leu Val Leu Val Val Ile Val Val Cys
        355                 360                 365

Ser Ile Arg Lys Ser Ser Arg Thr Leu Lys Lys Gly Pro Arg Gln Asp
    370                 375                 380

Pro Ser Ala Ile Val Glu Lys Ala Gly Leu Lys Lys Ser Met Thr Pro
385                 390                 395                 400

Thr Gln Asn Arg Glu Lys Trp Ile Tyr Tyr Cys Asn Gly His Gly Ile
                405                 410                 415

Asp Ile Leu Lys Leu Val Ala Ala Gln Val Gly Ser Gln Trp Lys Asp
            420                 425                 430

Ile Tyr Gln Phe Leu Cys Asn Ala Ser Glu Arg Glu Val Ala Ala Phe
        435                 440                 445

Ser Asn Gly Tyr Thr Ala Asp His Glu Arg Ala Tyr Ala Ala Leu Gln
    450                 455                 460

His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
                485                 490                 495

Leu Met Glu Asp Thr Thr Gln Leu Glu Thr Asp Lys Leu Ala Leu Pro
            500                 505                 510

Met Ser Pro Ser Pro Leu Ser Pro Ser Pro Ile Pro Ser Pro Asn Ala
        515                 520                 525

Lys Leu Glu Asn Ser Ala Leu Leu Thr Val Glu Pro Ser Pro Gln Asp
    530                 535                 540

Leu Leu Phe Lys Trp Leu Asp Asn Trp Ala Thr Lys Glu Leu Glu Leu
545                 550                 555                 560

His Leu Leu Gly Phe Glu Leu Phe Trp Asn Thr Leu Leu His Phe Gly
                565                 570                 575

Lys Ser Lys Ser Ser Ala Ser Gly Ala Leu Ser Ile Glu Asn Leu Pro
            580                 585                 590

Ser Phe Ala Leu Lys Asp Val Leu Phe Phe Ile Tyr Thr
        595                 600                 605
```

(2) INFORMATION FOR SEQ ID NO:24:

(i) SEQUENCE CHARACTERISTICS:
- (A) LENGTH: 1815 base pairs
- (B) TYPE: nucleic acid
- (C) STRANDEDNESS: single
- (D) TOPOLOGY: linear (ii) MOLECULE TYPE: cDNA (ix) FEATURE:
- (A) NAME/KEY: CDS
- (B) LOCATION: 1..1815

(xi) SEQUENCE DESCRIPTION: SEQ ID NO:24:

```
ATG GGG ACC TCT CCG AGC AGC AGC ACC GCC CTC GCC TCC TGC AGC CGC       48
Met Gly Thr Ser Pro Ser Ser Ser Thr Ala Leu Ala Ser Cys Ser Arg
  1               5                  10                  15
```

-continued

```
ATC GCC CGC CGA GCC ACA GCC ACG ATG ATC GCG GGC TCC CTT CTC CTG        96
Ile Ala Arg Arg Ala Thr Ala Thr Met Ile Ala Gly Ser Leu Leu Leu
            20                  25                  30

CTT GGA TTC CTT AGC ACC ACC ACA GCT CAG CCA GAA CAG AAG GCC TCG       144
Leu Gly Phe Leu Ser Thr Thr Thr Ala Gln Pro Glu Gln Lys Ala Ser
        35                  40                  45

AAT CTC ATT GGC ACA TAC CGC CAT GTT GAC CGT GCC ACC GGC CAG GTG       192
Asn Leu Ile Gly Thr Tyr Arg His Val Asp Arg Ala Thr Gly Gln Val
    50                  55                  60

CTA ACC TGT GAC AAG TGT CCA GCA GGA ACC TAT GTC TCT GAG CAT TGT       240
Leu Thr Cys Asp Lys Cys Pro Ala Gly Thr Tyr Val Ser Glu His Cys
 65                  70                  75                  80

ACC AAC ACA AGC CTG CGC GTC TGC AGC AGT TGC CCT GTG GGG ACC TTT       288
Thr Asn Thr Ser Leu Arg Val Cys Ser Ser Cys Pro Val Gly Thr Phe
                85                  90                  95

ACC AGG CAT GAG AAT GGC ATA GAG AAA TGC CAT GAC TGT AGT CAG CCA       336
Thr Arg His Glu Asn Gly Ile Glu Lys Cys His Asp Cys Ser Gln Pro
            100                 105                 110

TGC CCA TGG CCA ATG ATT GAG AAA TTA CCT TGT GCT GCC TTG ACT GAC       384
Cys Pro Trp Pro Met Ile Glu Lys Leu Pro Cys Ala Ala Leu Thr Asp
        115                 120                 125

CGA GAA TGC ACT TGC CCA CCT GGC ATG TTC CAG TCT AAC GCT ACC TGT       432
Arg Glu Cys Thr Cys Pro Pro Gly Met Phe Gln Ser Asn Ala Thr Cys
    130                 135                 140

GCC CCC CAT ACG GTG TGT CCT GTG GGT TGG GGT GTG CGG AAG AAA GGG       480
Ala Pro His Thr Val Cys Pro Val Gly Trp Gly Val Arg Lys Lys Gly
145                 150                 155                 160

ACA GAG ACT GAG GAT GTG CGG TGT AAG CAG TGT GCT CGG GGT ACC TTC       528
Thr Glu Thr Glu Asp Val Arg Cys Lys Gln Cys Ala Arg Gly Thr Phe
                165                 170                 175

TCA GAT GTG CCT TCT AGT GTG ATG AAA TGC AAA GCA TAC ACA GAC TGT       576
Ser Asp Val Pro Ser Ser Val Met Lys Cys Lys Ala Tyr Thr Asp Cys
            180                 185                 190

CTG AGT CAG AAC CTG GTG GTG ATC AAG CCG GGG ACC AAG GAG ACA GAC       624
Leu Ser Gln Asn Leu Val Val Ile Lys Pro Gly Thr Lys Glu Thr Asp
        195                 200                 205

AAC GTC TGT GGC ACA CTC CCG TCC TTC TCC AGC TCC ACC TCA CCT TCC       672
Asn Val Cys Gly Thr Leu Pro Ser Phe Ser Ser Ser Thr Ser Pro Ser
    210                 215                 220

CCT GGC ACA GCC ATC TTT CCA CGC CCT GAG CAC ATG GAA ACC CAT GAA       720
Pro Gly Thr Ala Ile Phe Pro Arg Pro Glu His Met Glu Thr His Glu
225                 230                 235                 240

GTC CCT TCC TCC ACT TAT GTT CCC AAA GGC ATG AAC TCA ACA GAA TCC       768
Val Pro Ser Ser Thr Tyr Val Pro Lys Gly Met Asn Ser Thr Glu Ser
                245                 250                 255

AAC TCT TCT GCC TCT GTT AGA CCA AAG GTA CTG AGT AGC ATC CAG GAA       816
Asn Ser Ser Ala Ser Val Arg Pro Lys Val Leu Ser Ser Ile Gln Glu
            260                 265                 270

GGG ACA GTC CCT GAC AAC ACA AGC TCA GCA AGG GGG AAG GAA GAC GTG       864
Gly Thr Val Pro Asp Asn Thr Ser Ser Ala Arg Gly Lys Glu Asp Val
        275                 280                 285

AAC AAG ACC CTC CCA AAC CTT CAG GTA GTC AAC CAC CAG CAA GGC CCC       912
Asn Lys Thr Leu Pro Asn Leu Gln Val Val Asn His Gln Gln Gly Pro
    290                 295                 300

CAC CAC AGA CAC ATC CTG AAG CTG CTG CCG TCC ATG GAG GCC ACT GGG       960
His His Arg His Ile Leu Lys Leu Leu Pro Ser Met Glu Ala Thr Gly
305                 310                 315                 320

GGC GAG AAG TCC AGC ACG CCC ATC AAG GGC CCC AAG AGG GGA CAT CCT      1008
Gly Glu Lys Ser Ser Thr Pro Ile Lys Gly Pro Lys Arg Gly His Pro
                325                 330                 335
```

```
AGA CAG AAC CTA CAC AAG CAT TTT GAC ATC AAT GAG CAT TTG CCC TGG     1056
Arg Gln Asn Leu His Lys His Phe Asp Ile Asn Glu His Leu Pro Trp
            340                 345                 350

ATG ATT GTG CTT TTC CTG CTG CTG GTG CTT GTG GTG ATT GTG GTG TGC     1104
Met Ile Val Leu Phe Leu Leu Leu Val Leu Val Val Ile Val Val Cys
        355                 360                 365

AGT ATC CGG AAA AGC TCG AGG ACT CTG AAA AAG GGG CCC CGG CAG GAT     1152
Ser Ile Arg Lys Ser Ser Arg Thr Leu Lys Lys Gly Pro Arg Gln Asp
    370                 375                 380

CCC AGT GCC ATT GTG GAA AAG GCA GGG CTG AAG AAA TCC ATG ACT CCA     1200
Pro Ser Ala Ile Val Glu Lys Ala Gly Leu Lys Lys Ser Met Thr Pro
385                 390                 395                 400

ACC CAG AAC CGG GAG AAA TGG ATC TAC TAC TGC AAT GGC CAT GGT ATC     1248
Thr Gln Asn Arg Glu Lys Trp Ile Tyr Tyr Cys Asn Gly His Gly Ile
                405                 410                 415

GAT ATC CTG AAG CTT GTA GCA GCC CAA GTG GGA AGC CAG TGG AAA GAT     1296
Asp Ile Leu Lys Leu Val Ala Ala Gln Val Gly Ser Gln Trp Lys Asp
            420                 425                 430

ATC TAT CAG TTT CTT TGC AAT GCC AGT GAG AGG GAG GTT GCT GCT TTC     1344
Ile Tyr Gln Phe Leu Cys Asn Ala Ser Glu Arg Glu Val Ala Ala Phe
        435                 440                 445

TCC AAT GGG TAC ACA GCC GAC CAC GAG CGG GCC TAC GCA GCT CTG CAG     1392
Ser Asn Gly Tyr Thr Ala Asp His Glu Arg Ala Tyr Ala Ala Leu Gln
    450                 455                 460

CAC TGG ACC ATC CGG GGC CCC GAG GCC AGC CTC GCC CAG CTA ATT AGC     1440
His Trp Thr Ile Arg Gly Pro Glu Ala Ser Leu Ala Gln Leu Ile Ser
465                 470                 475                 480

GCC CTG CGC CAG CAC CGG AGA AAC GAT GTT GTG GAG AAG ATT CGT GGG     1488
Ala Leu Arg Gln His Arg Arg Asn Asp Val Val Glu Lys Ile Arg Gly
                485                 490                 495

CTG ATG GAA GAC ACC ACC CAG CTG GAA ACT GAC AAA CTA GCT CTC CCG     1536
Leu Met Glu Asp Thr Thr Gln Leu Glu Thr Asp Lys Leu Ala Leu Pro
            500                 505                 510

ATG AGC CCC AGC CCG CTT AGC CCG AGC CCC ATC CCC AGC CCC AAC GCG     1584
Met Ser Pro Ser Pro Leu Ser Pro Ser Pro Ile Pro Ser Pro Asn Ala
        515                 520                 525

AAA CTT GAG AAT TCC GCT CTC CTG ACG GTG GAG CCT TCC CCA CAG GAT     1632
Lys Leu Glu Asn Ser Ala Leu Leu Thr Val Glu Pro Ser Pro Gln Asp
    530                 535                 540

TTG CTA TTT AAG TGG CTT GAC AAC TGG GCC ACC AAA GAA CTT GAA CTT     1680
Leu Leu Phe Lys Trp Leu Asp Asn Trp Ala Thr Lys Glu Leu Glu Leu
545                 550                 555                 560

CAC CTT TTA GGA TTT GAG CTG TTC TGG AAC ACA TTG CTG CAC TTT GGA     1728
His Leu Leu Gly Phe Glu Leu Phe Trp Asn Thr Leu Leu His Phe Gly
                565                 570                 575

AAG TCA AAA TCA AGT GCC AGT GGC GCC CTT TCC ATA GAG AAT TTG CCC     1776
Lys Ser Lys Ser Ser Ala Ser Gly Ala Leu Ser Ile Glu Asn Leu Pro
            580                 585                 590

AGC TTT GCT TTA AAA GAT GTC TTG TTT TTT ATA TAC ACA                 1815
Ser Phe Ala Leu Lys Asp Val Leu Phe Phe Ile Tyr Thr
        595                 600                 605
```

(2) INFORMATION FOR SEQ ID NO:25:

(i) SEQUENCE CHARACTERISTICS:
(A) LENGTH: 86 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:25:

```
Pro Ala Thr Leu Tyr Ala Val Val Glu Asn Val Pro Pro Leu Arg Trp
1               5                   10                  15

Lys Glu Phe Val Arg Arg Leu Gly Leu Ser Asp His Glu Ile Asp Arg
            20                  25                  30

Leu Glu Leu Gln Asn Gly Arg Cys Leu Arg Glu Ala Gln Tyr Ser Met
        35                  40                  45

Leu Ala Thr Trp Arg Arg Arg Thr Pro Arg Arg Glu Ala Thr Leu Glu
    50                  55                  60

Leu Leu Gly Arg Val Leu Arg Asp Met Asp Leu Leu Gly Cys Leu Glu
65                  70                  75                  80

Asp Ile Glu Glu Ala Leu
                85
```

(2) INFORMATION FOR SEQ ID NO:26:

(i) SEQUENCE CHARACTERISTICS:
(A) LENGTH: 85 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:26:

```
Ser Lys Tyr Ile Thr Thr Ile Ala Gly Val Met Thr Leu Ser Gln Val
1               5                   10                  15

Lys Gly Phe Val Arg Lys Asn Gly Val Asn Glu Ala Lys Ile Asp Glu
            20                  25                  30

Ile Lys Asn Asp Asn Val Gln Asp Thr Ala Glu Gln Lys Val Gln Leu
        35                  40                  45

Leu Arg Asn Trp His Gln Leu His Gly Lys Lys Glu Ala Tyr Asp Thr
    50                  55                  60

Leu Ile Lys Asp Leu Lys Lys Ala Asn Leu Cys Thr Leu Ala Glu Lys
65                  70                  75                  80

Ile Gln Thr Ile Ile
                85
```

(2) INFORMATION FOR SEQ ID NO:27:

(i) SEQUENCE CHARACTERISTICS:
(A) LENGTH: 91 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:27:

```
Ser Leu Lys Asp Gln Gln Thr Phe Ala Arg Ser Val Gly Leu Lys Trp
1               5                   10                  15

Arg Lys Val Gly Arg Ser Leu Gln Arg Gly Cys Arg Ala Leu Arg Asp
            20                  25                  30

Pro Ala Leu Asp Ser Leu Ala Tyr Glu Tyr Glu Arg Glu Gly Leu Tyr
        35                  40                  45

Glu Gln Ala Phe Gln Leu Leu Arg Arg Phe Val Gln Ala Glu Gly Arg
    50                  55                  60
```

Arg Ala Thr Leu Gln Arg Leu Val Glu Ala Leu Glu Glu Asn Glu Leu
65 70 75 80

Thr Ser Leu Ala Glu Asp Leu Leu Gly Leu Thr
85 90

(2) INFORMATION FOR SEQ ID NO:28:

(i) SEQUENCE CHARACTERISTICS:
(A) LENGTH: 85 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:28:

Leu Cys Ala Ala Phe Asn Val Ile Cys Asp Asn Val Gly Lys Asp Trp
1 5 10 15

Arg Arg Leu Ala Arg Gln Leu Lys Val Ser Asp Thr Lys Ile Asp Ser
20 25 30

Ile Glu Asp Arg Tyr Pro Arg Asn Leu Thr Glu Arg Val Arg Glu Ser
35 40 45

Leu Arg Ile Trp Lys Asn Thr Glu Lys Glu Asn Ala Thr Val Ala His
50 55 60

Leu Val Gly Ala Leu Arg Ser Cys Gln Met Asn Leu Val Ala Asp Leu
65 70 75 80

Val Gln Glu Val Gln
85

(2) INFORMATION FOR SEQ ID NO:29:

(i) SEQUENCE CHARACTERISTICS:
(A) LENGTH: 87 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:29:

Thr Asp Lys His Leu Asp Pro Ile Arg Glu Asn Leu Gly Lys His Trp
1 5 10 15

Lys Asn Cys Ala Arg Lys Leu Gly Phe Thr Gln Ser Gln Ile Asp Glu
20 25 30

Ile Asp His Asp Tyr Glu Arg Asp Gly Leu Lys Glu Lys Val Tyr Gln
35 40 45

Met Leu Gln Lys Trp Val Met Arg Glu Gly Ile Lys Gly Ala Thr Val
50 55 60

Gly Lys Leu Ala Gln Ala Leu His Gln Cys Ser Arg Ile Asp Leu Leu
65 70 75 80

Ser Ser Leu Ile Tyr Val Ser
85

(2) INFORMATION FOR SEQ ID NO:30:

(i) SEQUENCE CHARACTERISTICS:
(A) LENGTH: 84 amino acids
(B) TYPE: amino acid
(D) TOPOLOGY: linear -continued

```
    (ii) MOLECULE TYPE: peptide

     (v) FRAGMENT TYPE: internal

    (xi) SEQUENCE DESCRIPTION: SEQ ID NO:30:

Gly Ile Asp Ile Leu Lys Leu Val Ala Ala Gln Val Gly Ser Gln Trp
1               5                   10                  15

Lys Asp Ile Tyr Gln Phe Leu Cys Asn Ala Ser Glu Arg Glu Val Ala
            20                  25                  30

Ala Phe Ser Asn Gly Tyr Thr Ala Asp His Glu Arg Ala Tyr Ala Ala
        35                  40                  45

Leu Gln His Trp Thr Ile Arg Gly Pro Glu Ala Ser Leu Ala Gln Leu
    50                  55                  60

Ile Ser Ala Leu Arg Gln His Arg Arg Asn Asp Val Val Glu Lys Ile
65                  70                  75                  80

Arg Gly Leu Met


(2) INFORMATION FOR SEQ ID NO:31:

     (i) SEQUENCE CHARACTERISTICS:
          (A) LENGTH: 84 amino acids
          (B) TYPE: amino acid
          (D) TOPOLOGY: linear

    (ii) MOLECULE TYPE: peptide

     (v) FRAGMENT TYPE: internal

    (xi) SEQUENCE DESCRIPTION: SEQ ID NO:31:

Gly Ile Asp Ile Leu Lys Leu Val Ala Ala Gln Val Gly Ser Gln Trp
1               5                   10                  15

Lys Asp Ile Tyr Gln Phe Leu Cys Asn Ala Ser Glu Arg Glu Val Ala
            20                  25                  30

Ala Phe Ser Asn Gly Tyr Thr Ala Asp His Glu Arg Ala Tyr Ala Ala
        35                  40                  45

Leu Gln His Trp Thr Ile Arg Gly Pro Glu Ala Ser Leu Ala Gln Leu
    50                  55                  60

Ile Ser Ala Leu Arg Gln His Arg Arg Asn Asp Val Val Glu Lys Ile
65                  70                  75                  80

Arg Gly Leu Met
```

MOLECULES OF THE TNF RECEPTOR SUPERFAMILY AND USES THEREFOR

CROSS-REFERENCETO RELATED APPLICATIONS

The present application is a continuation-in-part of prior-filed application U.S. patent application Ser. No. 08/938,896, entitled "Novel Molecules of the TNF Receptor Superfamily and Uses Therefor", filed Sep. 26, 1997. The contents of the above-referenced patent application is incorporated herein by this reference in its entirety.

BACKGROUND OF THE INVENTION

The tumor necrosis factor receptor (TNFR) superfamily of proteins encompasses over a dozen members, most of which are type I transmembrane proteins, related by the presence of conserved cysteine-rich repeats (CRRs) in their N-terminal cysteine-rich domains (CRDs). Members of the TNFR superfamily include TNFRI (p55), TNFR2 (p75), TNFR3 (TNF-RP), Fas (also known as CD95 and Apol ), OX-40, 41 -BB, CD40, CD30, CD27, OPG, and p75 NGFR. (Smith et al. (1993) *Cell* 76:959–962; Armitage, R. J. (1994) *Curr. Opin. Immunol.* 6:407–413; Gruss et al. (1995) *Blood* 85, 3378–3404; Baker et al. (1996) *Oncogene* 12:1–9; and Simonet et al. (1997) *Cell* 89:309–319.) A TNFR superfamily member is typically a membrane-bound, trimeric or multimeric complex which is stabilized via intracysteine disulfide bonds that are formed between the cysteine-rich domains of individual subunit members (Banner et al. (1993) *Cell* 73:431–445). The proteins themselves do not have intrinsic catalytic activity, rather they function via association with other proteins to transduce cellular signals.

Most members of the TNFR superfamily recognize ligands that play critical roles as costimulators in immune responses. However, a subset of TNFR superfamily members have been determined to play a key role in the extracellular regulation of cell death. Induction of cell death requires a unique cytoplasmic motif which was originally identified in TNFRI and Fas and termed the "death domain" (Tartaglia et al. (1993) *Cell* 74:845–853 and Itoh and Nagata (1993) *J. Biol. Chem.* 268:10932–10937). Using the yeast two-hybrid method to clone genes encoding proteins that associate with the cytoplasmic domains of TNFRL or Fas, three dramatically different genes were identified (TRADD in Hsu et al (1995) Cell 81:495–504; FADD in Chinnaiyan et al. (1995) *Cell* 81:501–512; and RIP in Stanger et al. (1995) *Cell* 81:512–523). FADD was independently cloned with the same strategy, and termed MORT1 (Boldin et al. (1995) *J. Biol. Chem.* 270:7795–7798.) In fact, the only structural similarity between these proteins was the shared motif that has homology with the death domains of the TNFRI and Fas receptors. Death domains have recently been identified in a variety of proteins including, for example, the ankyrins, the *Drosophila* proteins PELLE and TUBE, DAP kinase, mouse myD88. (For review see Feinstein and Kimchi (1995) *Trends. Biochem. Sci.* 20:342–344; Golstein et al. (1995) *Cell* 81:185–186; Cleveland and Ihle (1995) *Cell* 81:479–482; and Hofinan and Tschopp (1995) *FEBS Lett.* 371:321–323). Moreover, the death domain has been implicated in protein:protein interactions between two proteins each containing such a domain. Such a death domain:death domain interaction is believed to be a crucial component of the cellular signal transduction pathways that lead to cell death, thus, implicating members of the TNFR superfamily in a wide range of signal transduction with appreciably diverse outcomes.

Aside from the membrane-bound forms of TNFR superfamily proteins that function as cellular signal transducers, a functional TNFR superfamily protein can also exist in a soluble form. Soluble versions of the superfamily bind cognate ligands and influence bioavailability. For instance, the osteoprotegerin protein family exists as a soluble protein (Simonet et al. (1997) *Cell* 89:309–319). Many soluble forms of the TNFR have been identified. Certain soluble TNFRs are elevated in disease states such as lupus and rheumatoid arthritis (Gabay et al. (1997) *J. Rheumatol.* 24(2):303–308). The soluble superfamily members lack the transmembrane domain characteristic of the majority of superfamily members due to either proteolytic cleavage or, at least in one instance, to alternative splicing (Gruss et al. (1995) *Blood* 85, 3378–3404).

Given the important role of proteins of the TNFR superfamily, including both soluble as well as membrane-bound family members, in a wide range of cellular signal transduction pathways, there exists a need for identifying novel members of the TNFR superfamily as well as for modulators of such molecules for use in regulating a variety of cellular responses.

SUMMARY OF THE INVENTION

The present invention is based, at least in part, on the discovery of novel molecules of the TNF receptor superfamily, referred to herein as TNF receptor-like "TRL" nucleic acid and protein molecules. The TRL molecules of the present invention are useful as modulating agents in regulating a variety of cellular processes. Accordingly, in one aspect, this invention provides isolated nucleic acid molecules encoding TRL proteins or biologically active portions thereof, as well as nucleic acid fragments suitable as primers or hybridization probes for the detection of TRL-encoding nucleic acids. In one embodiment, an isolated nucleic acid molecule of the present invention preferably encodes a TRL protein which includes a cysteine-rich domain, a C-terminal unique domain and is membrane bound or secreted. In another embodiment, the nucleic acid molecule is a naturally occurring nucleotide sequence.

In another embodiment, a nucleic acid molecule of the invention is 60% homologous to the nucleotide sequence shown in SEQ ID NO: 1, SEQ ID NO:3, SEQ ID NO:22, the nucleotide sequence of the DNA insert of the plasmid deposited with ATCC as Accession Number 98649, or a complement thereof and, preferably, encodes a TRL protein. In yet another embodiement, the isolated nucleic acid molecule is 60% homologous to the nucleotide sequence shown in SEQ ID NO:5, SEQ ID NO:6, SEQ ID NO:24, or a complement thereof and, preferably, encodes a TRL protein. In a preferred embodiment, the isolated nucleic acid molecule encodes the amino acid sequence of human or mouse TRL protein.

In another embodiment, the isolated nucleic acid includes a nucleotide sequence encoding a protein having an amino acid sequence sufficiently homologous to a cysteine-rich domain amino acid sequence of SEQ ID NO:2, SEQ ID NO:4, or SEQ ID NO:23 and, preferably, encodes a TRL protein. In a preferred embodiment, the nucleic acid molecule has the nucleotide sequence shown in SEQ ID NO:5, SEQ ID NO:6, or SEQ ID NO:24. In another preferred embodiment, the nucleic acid molecule has the nucleotide sequence shown in SEQ ID NO: 1, SEQ ID NO:3, SEQ ID NO:22, or the nucleotide sequence of the DNA insert of the plasmid deposited with ATCC as Accession Number 98649.

Another embodiment of the invention features isolated nucleic acid molecules which specifically detect TRL nucleic acid molecules relative to nucleic acid molecules encoding other TNFR superfamily molecules. For example, in one embodiment, the nucleic acid molecule hybridizes under stringent conditions to a nucleic acid molecule comprising the nucleotide sequence shown in nucleotides 480 to 1165 of SEQ ID NO: I or nucleotides 455 to 2155 of SEQ ID NO:3. In another embodiment, the nucleic acid molecule is at least 500 nucleotides in length and hybridizes under stringent conditions to a nucleic acid molecule comprising the nucleotide sequence shown in SEQ ID NO:1, SEQ ID NO:3, SEQ ID NO:22, the nucleotide sequence of the DNA insert of the plasmid deposited with ATCC as Accession Number 98649, or a complement thereof In a preferred embodiment, an isolated nucleic acid molecule comprises nucleotides 344–2062 of SEQ ID NO: 1 or a complement thereof. In another embodiment, the nucleic acid molecule firther comprises nucleotides 1–343 of SEQ ID NO: 1. In yet another preferred embodiment, the nucleic acid molecule further comprises nucleotides 2063–3331 of SEQ ID NO:1.

In another preferred embodiment of the invention, an isolated nucleic acid molecule comprises nucleotides 190–948 of SEQ ID NO:3 or a complement thereof. In another embodiment, the nucleic acid molecule further comprises nucleotides 1–189 of SEQ ID NO:3. In yet another preferred embodiment, the nucleic acid molecule further comprises nucleotides 949–2612 of SEQ ID NO:3.

In another preferred embodiment of the invention, an isolated nucleic acid molecule comprises nucleotides 510–2324 of SEQ ID NO:22 or a complement thereof. In another embodiment, the nucleic acid molecule further comprises nucleotides 1–509 of SEQ ID NO:22. In yet another preferred embodiment, the nucleic acid molecule further comprises nucleotides 2325–2638 of SEQ ID NO:22.

Another embodiment the invention provides an isolated nucleic acid molecule which is antisense to the coding strand of a TRL nucleic acid.

Another aspect of the invention provides a vector comprising a nucleic acid molecule of the invention, preferably a TRL nucleic acid molecule. In certain embodiments, the vector is a recombinant expression vector. In another embodiment the invention provides a host cell containing a vector of the invention. The invention also provides a method for producing TRL protein by culturing in a suitable medium, a host cell of the invention containing a recombinant expression vector such that TRL protein is produced.

Another aspect of this invention features isolated or recombinant proteins and polypeptides, preferably TRL proteins and polypeptides. In one embodiment, the isolated protein, preferably a TRL protein, has a cysteine-rich domain, a C-terminal unique domain and is membrane bound or secreted. In another embodiment, an isolated protein, preferably a TRL protein, has an amino acid sequence sufficiently homologous to a cysteine-rich domain amino acid sequence of SEQ ID NO:2, SEQ ID NO:4, or SEQ ID NO:23. In another embodiment, the invention features fragments of the proteins having the amino acid sequence of SEQ ID NO:2, SEQ ID NO:4, or SEQ ID NO:23, wherein the fragment comprises at least 15 contiguous amino acids of the amino acid sequence of SEQ ID NO:2, SEQ ID NO:4, SEQ ID NO:23, or an amino acid sequence encoded by the DNA insert of the plasmid deposited with the ATCC as Accession No. 98649. In a preferred embodiment, the protein has the amino acid sequence of SEQ ID NO:2, SEQ ID NO:4, or SEQ ID NO:23.

Another embodiment of the invention features isolated proteins, preferably TRL proteins, having an amino acid sequence at least about 60% homologous to the amino acid sequence of SEQ ID NO:2, SEQ ID NO:4, or SEQ ID NO:23. Yet another embodiment of the invention features isolated protein, preferably TRL proteins, which are encoded by nucleic acid molecules having a nucleotide sequence at least about 60% homologous to a nucleotide sequence of SEQ ID NO:5, SEQ ID NO:6, SEQ ID NO:1, SEQ ID NO:3, SEQ ID NO:22, the nucleotide sequence of the DNA insert of the plasmid deposited with ATCC as Accession Number 98649, or a complement thereof. This invention further features isolated proteins, preferably TRL proteins, which are encoded by a nucleic acid molecules having a nucleotide sequence which hybridizes under stringent hybridization conditions to a nucleic acid molecule comprising the nucleotide sequence of SEQ ID NO:5, SEQ ID NO:6, SEQ ID NO:1, SEQ ID NO:3, SEQ ID NO:22, or the nucleotide sequence of the DNA insert of the plasmid deposited with ATCC as Accession Number 98649.

The proteins of the present invention, preferably TRL proteins, or biologically active portions thereof, can be operatively linked to a non-TRL polypeptide to form fusion proteins, preferably TRL fusion proteins. The invention further features antibodies that specifically bind TRL proteins, such as monoclonal or polyclonal antibodies. In addition, the proteins of the invention or biologically active portions thereof can be incorporated into pharmaceutical compositions, which optionally include pharmaceutically acceptable carriers.

In another aspect, the present invention provides a method for detecting the presence of TRL activity or expression in a biological sample by contacting the biological sample with an agent capable of detecting an indicator of TRL activity such that the presence of TRL activity is detected in the biological sample.

In another aspect, the invention provides a method for modulating TRL activity comprising contacting a cell capable of expressing TRL with an agent that modulates TRL activity such that TRL activity in the cell is modulated. In one embodiment, the agent inhibits TRL activity. In another embodiment, the agent stimulates TRL activity. In one embodiment, the agent is an antibody that specifically binds to TRL protein. In another embodiment, the agent modulates expression of TRL by modulating transcription of a TRL gene or translation of a TRL mRNA. In yet another embodiment, the agent is a nucleic acid molecule having a nucleotide sequence that is antisense to the coding strand of the TRL MRNA or the TRL gene.

In one embodiment, the methods of the present invention are used to treat a subject having a disorder characterized by aberrant TRL protein or nucleic acid expression or activity by administering an agent which is a TRL modulator to the subject. In one embodiment, the TRL modulator is a TRL protein. In another embodiment the TRL modulator is a TRL nucleic acid molecule. In yet another embodiement, the TRL modulator is a peptide, peptidomimetic, or other small molecule. In a preferred embodiment, the disorder characterized by aberrant TRL protein or nucleic acid expression is a proliferative or differentiative disorder.

The present invention also provides a diagnostic assay for identifying the presence or absence of a genetic lesion characterized by at least one of (i) aberrant modification or mutation of a gene encoding a TRL protein; (ii) misregulation of said gene; and (iii) aberrant post-translational modification of a TRL protein, wherein a wild-type form of said gene encodes an protein with a TRL activity.

In another aspect, the invention provides a method for identifying a compound that binds to or modulates the activity of a TRL protein, by providing a indicator composition comprising a TRL protein having TRL activity, contacting the indicator composition with a test compound, and determining the effect of the test compound on TRL activity in the indicator composition to identify a compound that modulates the activity of a TRL protein.

Other features and advantages of the invention will be apparent from the following detailed description and claims.

BRIEF DESCRIPTION OF THE DRAWINGS

FIGS. 1A–E depicts the cDNA sequence and predicted amino acid sequence of murine TRL. The nucleotide sequence corresponds to nucleic acids 1 to 3331 of SEQ ID NO:1. The amino acid sequence corresponds to amino acids 1 to 573 of SEQ ID NO:2.

FIGS. 2A–C depicts the cDNA sequence and predicted amino acid sequence of human TRL I. The nucleotide sequence corresponds to nucleic acids 1 to 2612 of SEQ ID NO:3. The amino acid sequence corresponds to amino acids 1 to 273 of SEQ ID NO:4.

FIGS. 3A–G depicts an alignment of the amino acid sequences of human TRL I (corresponding to amino acids 1 to 273 of SEQ ID NO:4), human TRL II (corresponding to amino acids 1 to 605 of SEQ ID NO:23), murine TRL (corresponding to amino acids 1 to 573 of SEQ ID NO:2, human TNFR2 precursor (Swiss-ProtTM Accession No. P20333) (corresponding to amino acids 1 to 461 of SEQ ID NO:7), murine TNFR2 precursor (Swiss-Prot™ Accession No. P25119) (corresponding to amino acids 1 to 474 of SEQ ID NO:8), soluble TNFR2 precursor (Swiss-ProtTM Accession No. P25943) (corresponding to amino acids 1 to 325 of SEQ ID NO:9), human CD40 receptor precursor (Swiss-Prot™ Accession No. P25942) (corresponding to amino acids 1 to 277 of SEQ ID NO:10), murine CD40 receptor precursor (Swiss-Prot™ Accession No. P27512) (corresponding to amino acids 1 to 289 of SEQ ID NO:I 1), human osteoprotegerin (Swiss-Prot™ Accession No. U94332) (corresponding to amino acids 1 to 401 of SEQ ID NO:12), and murine osteoprotegerin (Swiss-Prot™ Accession No. U94331) (corresponding to amino acids 1 to 401 of SEQ ID NO:13).

FIGS. 4A–D depicts the cDNA sequence and predicted amino acid sequence of human TRL II. The nucleotide sequence corresponds to nucleic acids 1 to 2638 of SEQ ID NO:22. The amino acid sequence corresponds to amino acids 1 to 605 of SEQ ID NO:23.

FIGS. 5A–B depicts an alignment of the amino acid sequences of human TRL II (corresponding to amino acids 1 to 605 of SEQ ID NO:23), human TRL I (corresponding to amino acids 1 to 273 of SEQ ID NO:4), and murine TRL (corresponding to amino acids 1 to 573 of SEQ ID NO:2.

FIG. 6 depicts an alignment of the amino acid sequences of the human TNFRI (Swiss-Prot™ Accession No.P19438) death domain (corresponding to amino acids 356–441 of human TNFRI or, alternatively, corresponding to amino acids 1–86 of SEQ ID NO:25), the human Fas (Swiss-Prot™ Accession No. P25445) death domain (corresponding to amino acids 230–314 of human Fas or, alternatively, corresponding to amino acids 1–85 of SEQ ID NO:26), the human TRADD (GenBank™Accession No. L41690) death domain (corresponding to amino acids 231–321 human TRADD or, alternatively, corresponding to amino acids 1–91 of SEQ ID NO:27), the human FADD (EMBL™ Accession No. X84709) death domain (corresponding to amino acids 97–181 of human FADD or, alternatively, corresponding to amino acids 1–85 of SEQ ID NO:28), the human RIP (Swiss-Protm Accession No. U25994) death domain (corresponding to amino acids 284–370 of human RIP or, alternatively, corresponding to amino acids 1–87 of SEQ ID NO:29, the human TRL II death domain (corresponding to amino acids 415–498 of SEQ ID NO:23 or alternatively, amino acids 1–84 of SEQ ID NO:30), and the mouse TRL death domain (corresponding to amino acids 333–416 of SEQ ID NO:2 or alternatively, amino acids 1–84 of SEQ ID NO:31). Identical or similar amino acids are indicated in bold. Highly conserved amino acids are indicated by astrices.

DETAILED DESCRIPTION OF THE INVENTION

The present invention is based on the discovery of novel molecules of the TNF receptor superfamily, referred to herein as TRL protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defmed herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

In one embodiment, an isolated protein of the invention, preferably a TRL protein, is identified based on the presence of at least one "cysteine-rich domain" in the protein or corresponding nucleic acid molecule. As used herein, the term "cysteine-rich domain" refers to a protein domain having an amino acid sequence of at least about preferably at least about 30, more preferably at least about 35–40 amino acid residues, of which at least about 2, preferably at least about 3, more preferably at least about 4, 5 or 6 amino acids are the amino acid residue cysteine. Cysteine-rich domains having lengths of 45–50 or 60 amino acid residues and having up to 7, 8, 9 or 10 cysteine residues are also within the scope of this invention. In one embodiment, an isolated protein, preferably a TRL protein, includes a cysteine rich domain having at least about 20%, preferably at least about 30%, and more preferably about 40% amino acid sequence homology to a TNFR cysteine-rich domain (also referred to as a cysteine-rich repeat or "CRR"), such as the TNFR cysteine-rich domain of SEQ ID NO:2, SEQ ID NO:4, or SEQ ID NO:23 (e.g., amino acid residues 39–77, 78–119, 120–164, and 165–203 of murine TNFR2 or amino acid residues 39–76, 77–118, 119–162, and 163–201 of human TNFR2, respectively). Preferably, the isolated protein includes at least two cysteine-rich domains, more preferably at least three cysteine-rich domains, and more preferably at least four or five cysteine-rich domains. For example, in one embodiment, the isolated protein is a TRL protein which contains two or more cysteine-rich domains and has at least about 20%, more preferably about 30%, and even more preferably about 40% homology to a TNFR cysteine-rich domain of SEQ ID NO:2, SEQ ID NO:4, or SEQ ID NO:23 (e.g., amino acid residues 39–203 of murine TNFR2 or amino acid residues 39–201 of human TNFR2, respectively).

Preferred molecules of the present invention have an amino acid sequence sufficiently homologous to a cysteine rich domain amino acid sequence of SEQ ID NO:2, SEQ ID NO:4, or SEQ ID NO:23 or a nucleotide sequence sufficiently homologous to a nucleotide sequence encoding a cysteine rich domain of SEQ ID NO:2, SEQ ID NO:4, or SEQ ID NO:23. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least about 50% homology, preferably 60% homology, more preferably 70%–80%, and even more preferably 90–95% homology across the amino acid sequences of the domains and contain at least one and preferably two structural domains or motifs, are defined herein as sufficiently homologous. Furthermore, amino acid or nucleotide sequences which share at least 50%, preferably 60%, more preferably 70–80% or 90–95% homology and share a common functional activity are defined herein as sufficiently homologous. In one embodiment, the a TRL protein contains a cysteine-rich domain and has a TRL activity.

As used interchangeably herein a "TRL activity", "biological activity of TRL" or "functional activity of TRL", refers to an activity exerted by a TRL protein, polypeptide or nucleic acid molecule on a TRL responsive cell as determined in vivo, or in vitro, according to standard techniques. In one embodiment, a TRL activity is a direct activity, such as an association with or an enzymatic activity on a second protein. In another embodiment, a TRL activity is an indirect activity, such as a cellular signaling activity mediated by interaction of the TRL protein with a second protein. In a preferred embodiment, a TRL activity is at least one or more of the following activities: (i) formation of a homogeneous multimeric signaling complex with like TRL proteins; (ii) formation of a heterogeneous multimeric signaling complex with other TNFR superfamily proteins or other cell-surface proteins; (iii) complex formation between a membrane-bound TRL protein and a cytokine; (iv) complex formation between a soluble TRL protein and a cognate ligand; (v) interaction of a TRL protein with an intracellular protein having substantial homology to the TNFR-associated proteins; (vi) interaction of a TRL protein with a TNFR-associated protein; and (vii) interaction of a TRL protein with other cellular proteins including cytoplasmic proteins (e.g. SH2 domain-containing proteins or a second death domain-containing protein) or cytoskeletal proteins. In yet another preferred embodiment, a TRL activity is at least one or more of the following activities: (i) modulation of cellular signal transduction; (ii) regulation of cellular proliferation; (iii) regulation of cellular differentiation; (iv) regulation of cell survival or apoptosis; and (v) modulation of a cell involved in the immune response.

Accordingly, another embodiment of the invention features isolated TRL proteins and polypeptides having a TRL activity. Preferred proteins are TRL proteins having at least one cysteine-rich domain (and preferably two or more cysteine-rich domains) and, preferably, a TRL activity. In another preferred embodiment, the isolated protein, preferably a TRL protein, has at least one cysteine-rich domain (and preferably two or more cysteine-rich domains), a TRL activity and an amino acid sequence sufficiently homologous to an amino acid sequence of SEQ ID NO:2, SEQ ID NO:4, or SEQ ID NO:23.

Another embodiment of the invention features molecules, preferably TRL molecules, which contain a C-terminal unique domain. The term "C-terminal unique domain" as used herein, refers to a protein domain of a TRL protein family member (or TNFR protein superfamily member) which includes amino acid residues C-terminal to the C-terninus of a cysteine-rich domain in the amino acid sequence of the TRL protein (or TNFR protein superfamily member), e.g., a protein domain which includes amino acid residues from the C-terminus of the cysteine-rich domain to the C-terminal amino acid residue of the amino acid sequence of the protein. A C-terminal unique domain is sufficiently homologous between TRL protein family members such that the domain is at least about 40%, preferably about 50%, more preferably about 60%, even more preferably about 70%, 80%, or 90% homologous. As defined herein, a C-terminal unique domain of a TRL protein family member, however, is not sufficiently homologous to a C-terminal unique domain of a member of another protein family, such as a TNFR protein family.

A C-terminal unique domain of a TRL protein family member can further comprise a "death domain". As referred to herein, a death domain comprises about 50–100, prefereably 60–90, more prefereably 70–80 amino acids residues and can be localized near the C-terminal end of a naturally-occurring, death-domain-containing protein. For example, the C-terminus of a death domain located near the C-termninal end of a protein can be located at least about 2–200 amino acid residues from the C-terminus of the protein. Sequence homology among death domains is found at both at the C-terminal and N-terminal end of the death domain, with the intervening middle region frequently containing amino acid insertions or deletions. An alignment of several death domains is provided in FIG. 6. There are several amino acid positions within the domain that are highly conserved among death domain-containing family members, in particular, the tryptophans and leucine indicated by astrices in FIG. 6. In a preferred embodiment, the death domain has at least 2, preferably 3 leucines which are conserved. In another preferred embodiment, the death domain has at least 1, preferably 2 tryptophans which are conserved. A death domain is further predicted to have an overall α-helical structure.

Accordingly, in one embodiment, proteins of the invention, preferably TRL proteins, contain at least one cysteine-rich domain (and preferably two or more cysteine-rich domains) and have an amino acid sequence sufficiently homologous to a C-terminal unique domain amino acid sequence of SEQ ID NO:2, SEQ ID NO:4, or SEQ ID NO:23. In another preferred embodiment, the isolated protein, preferably a TRL protein, has at least one cysteine-rich domain (and preferably two or more cysteine-rich domains), an amino acid sequence sufficiently homologous to a C-terminal unique domain amino acid sequence of SEQ ID NO:2, SEQ ID NO:4, or SEQ ID NO:23 and a TRL activity. In another preferred embodiment, the isolated protein, preferably a TRL protein, has at least one cysteine-rich domain (and preferably two or more cysteine-rich domains), an amino acid sequence sufficiently homologous to a C-terminal unique domain amino acid sequence of SEQ ID NO:2, SEQ ID NO:4, or SEQ ID NO:23, wherein the C-terminal unique domain contains a death domain. In another preferred embodiment, the isolated protein, preferably a TRL protein, has at least one cysteine-rich domain (and preferably two or more cysteine-rich domains), an amino acid sequence sufficiently homologous to a C-terminal unique domain amino acid sequence of SEQ ID NO:2, SEQ ID NO:4, or SEQ ID NO:23, wherein the C-terminal unique domain contains a death domain, and has a TRL activity.

In yet another embodiment of the invention, the isolated protein and nucleic acid molecules, preferably TRL molecules, contain a transmembrane domain. As used herein, the term "transmembrane domain" refers to an amino acid sequence having at least about 10, preferably about 13, preferably about 16, more preferably about 19, and even more preferably about 21, 23, 25, 30, 35 or 40 amino acid residues, of which at least about 60–70%, preferably about 80% and more preferably about 90% of the amino acid residues contain non-polar side chains, for example, alanine, valine, leucine, isoleucine, proline, phenylalanine, tryptophan, and methionine. A transmembrane domain is lipophillic in nature. For example, a transmembrane domain can be found at about amino acids 352–370 of SEQ ID NO:23 (Trp352 to Ile370 of the human TRL II amino acid sequence).

Yet another embodiment of the invention features TRL molecules which contain a signal sequence. As used herein, a "signal sequence" refers to a peptide of about 20–30 amino acid residues in length which occurs at the N-terminus of secretory and integral membrane proteins and which contains a majority of hydrophobic amino acid residues. For example, a signal sequence contains at least about 15–45 amino acid residues, preferably about 20–40 amino acid residues, more preferably about 25–35 amino acid residues, and more preferably about 28–32 amino acid residues, and has at least about 40–70%, preferably about 50–65%, and more preferably about 55–60% hydrophobic amino acid residues (e.g., Alanine, Valine, Leucine, Isoleucine, Phenylalanine, Tyrosine, Tryptophan, or Proline). Such a "signal sequence", also referred to in the art as a "signal peptide", serves to direct a protein containing such a sequence to a lipid bilayer. For example, a signal sequence can be found about amino acids 1–41 of SEQ ID NO:23 (Metl to Ala4l of the human TRL II amino acid sequence.)

In a particularly preferred embodiment, the TRL protein and nucleic acid molecules of the present invention are human TRL molecules. A nucleotide sequence of the isolated human TRL I cDNA and the predicted amino acid sequence of the human TRL I protein are shown in FIG. 2A–C and in SEQ ID NOs:3 and 4, respectively. In addition, the nucleotide sequence corresponding to the coding region of the human TRL I cDNA (nucleotides 190–948) is represented as SEQ ID NO:6.

A 4.2 kb TRL mRNA transcript is expressed in human tissues including heart, brain, placenta, lung, liver, skeletal muscle, kidney, pancreas, spleen, thymus, prostate, testis, ovary, small intestine, colon, and peripheral blood lymphocytes, with more pronounced expression observed in human kidney, brain, placenta, and colon. Chromosomal mapping indicates that the human TRL gene is located on chromosome 6p25.

The human TRL I cDNA, which is approximately 2612 nucleotides in length, encodes a protein having a molecular weight of approximately 27 kDa (excluding post-translational modifications) and which is approximately 253 amino acid residues in length. The human TRL I protein contains four cysteine-rich domains. A TRL cysteine rich domain can be found at least, for example, from about amino acids 47–89 of SEQ ID NO:4 (Ala47 to Ser89 of the human TRL I amino acid sequence); from about amino acids 90–131 of SEQ ID NO:4 (Ser90 to Cysl 31 of the human TRL I amino acid sequence); from about amino acids 132–169 of SEQ ID NO:4 (Thr132 to Lysl69 of the human TRL I amino acid sequence); and from about amino acids 170–212 of SEQ ID NO:4 (Gln170 to Gly212 of the human TRL I amino acid sequence.) The human TRL I protein is a secreted protein which lacks a transmembrane domain, however the N-terminal cysteine-rich domain shares significant homology with a membrane bound form of TRL. The human TRL I protein further contains a signal sequence at about amino acids 1–41 of SEQ ID NO:4 [Met] to Ala41 of the human TRL I amino acid sequence.) The prediction of such a signal peptide can be made utilizing the computer algorithm SIGNALP (Henrik, et al. (1997) Protein Engineering 10:1–6).

A nucleotide sequence of the isolated human TRL II cDNA and the predicted amino acid sequence of the human TRL II protein are shown in FIG. 4 and in SEQ ID NOs:23 and 24, respectively. In addition, the nucleotide sequence corresponding to the coding region of the human TRL 11 cDNA (nucloetides 510–2324) is represented as SEQ ID NO:25.

The human TRL II cDNA, which is approximately 2638 nucleotides in length, encodes a protein having a molecular weight of approximately 66.2 kDa (excluding post-translational modifications) and which is approximately 605 amino acid residues in length. A plasmid containing the full length nucleotide sequence encoding human TRL II (clone designation ephT75L) was deposited under the provisions of the Budapest Treaty with the American Type Culture Collection (ATCC), 10801 University Blvd., Manessas, Va., 02110-2209 USA, on Feb. 6, 1998 and assigned Accession Number 98649. The human TRL II protein contains four cysteine-rich domains. A TRL cysteine rich domain can be found at least, for example, from about amino acids 47–89 of SEQ ID NO:23 (Ala47 to Ser89 of the human TRL II amino acid sequence); from about amino acids 90–131 of SEQ ID NO:23 (Ser90 to Cys 131 of the human TRL 11 amino acid sequence); from about amino acids 132–169 of SEQ ID NO:23 (Thr132 to Lys169 of the human TRL II amino acid sequence); and from about amino acids 170–212 of SEQ ID NO:23 (Gln170 to Gly212 of the human TRL II amino acid sequence.) The human TRL II protein contains three potential protein kinase C phosphorylation sites at amino acids 441, 467 and 506 of SEQ ID NO 23. The human TRL II protein is a membrane-bound protein which contains a ransmembrane domain at about amino acids 352–370 of SEQ ID NO:23 (Trp352 to Ile370 of the human TRL II amino acid sequence). The human TRL II protein further contains a signal sequence at about amino acids 1–41 of SEQ ID NO:23 (Met1 to Ala4l of the human TRL II amino acid sequence.) The prediction of such a signal peptide can be made utilizing the computer algorithm SIGNALP (Henrik, et al. (1997) *Protein Engineering* 10: 1–6). The C-terrninal unique region of human TRL II contains a death domain at amino acids 415–498 of SEQ ID NO:23.

In another preferred embodiment, the TRL protein and nucleic acid molecules of the present invention are murine TRL molecules. A murine TRL nucleic acid molecule was identified from a primary murine megakaryocyte cDNA library (described in further detail in Example 1). The nucleotide sequence of the isolated murine TRL cDNA and the predicted amino acid sequence of the murine TRL protein are shown in FIG. 1A–E and in SEQ ID NOs: 1 and 2, respectively. In addition, the coding region of murine TRL cDNA (corresponding to nucleotides 344–2062) is depicted as SEQ ID NO:5.

A 4.2 kb TRL MRNA transcript is expressed in mouse tissues including heart, brain, spleen, lung, liver, skeletal muscle, kidney, and testis, with more pronounced expression observed in mouse kidney and brain. Chromosomal mapping indicates that the murine TRL gene is located 12cM distal of D17MIT48 and 20cM proximal of D17MIT9. This region is syntenic to 6p21 in human.

The murine TRL gene, which is approximately 3331 nucleotides in length, encodes a protein having a molecular weight of approximately 63 kDa (excluding post-translational modifications) and which is approximately 573 amino acid residues in length. The murine TRL protein contains at least three cysteine-rich domains. A TRL cysteine-rich domain can be found at least, for example, from about amino acids 8–49 of SEQ ID NO:2 (Ser8 to Cys49 of the murine TRL amino acid sequence); from about amino acids 50–87 of SEQ ID NO:2 (Ile50 to Lys87 of the murine TRL amino acid sequence); from about amino acids 88–130 of SEQ ID NO:2 (Gln88 to Glyl 30 of the murine TRL amino acid sequence). The murine TRL protein is a membrane-bound protein which contains a transmembrane domain at about amino acids 270–288 of SEQ ID NO:2 (Trp270 to Ile288 of the murine TRL amino acid sequence). The C-terminal unique region of murine TRL contains a death domain at amino acids 333–416 of SEQ ID NO:2.

An alignment of the human TRL I and murine TRL amino acid sequences to other members of the TNFR superfamily of proteins is presented in FIG. 3A–G. The figure depicts an alignment of the amino acid sequences of human TRL (corresponding to amino acids 1 to 273 of SEQ ID NO:4), murine TRL (corresponding to amino acids 1 to 573 of SEQ ID NO:2, human TNFR2 precursor (Swiss-Prot™ Accession No. P20333), murine TNFR2 precursor (Swiss-Prot™ Accession No. P25119), soluble TNFR2 precursor (Swiss-Prot™ Accession No. P25943), human CD40 receptor precursor (Swiss-Prot™ Accession No. P25942), murine CD40 receptor precursor (Swiss-Prot™ Accession No. P27512), human osteoprotegerin (Swiss-Prot™ Accession No. U94332), and murine osteoprotegerin (Swiss-Prot™ Accession No. U9433 1). A signal sequence is designated by bold characters. Cysteine-rich domains are designated alternatively by italicized characters or by underlined, italicized characters. A transmembrane domain is indicated by bold, underlined characters.

An alignment of the human TRL I, human TRL II, and murine TRL amino acid sequences is presented in FIGS. 5A–B. A signal sequence is designated by bold characters. Cysteine-rich domains are designated alternatively by italicized characters or by underlined, italicized characters. A transmembrane domain is indicated by bold, underlined characters.

Various aspects of the invention are described in further detail in the following subsections:

I. Isolated Nucleic Acid Molecules

One aspect of the invention pertains to isolated nucleic acid molecules that encode TRL proteins or biologically active portions thereof, as well as nucleic acid fragments sufficient for use as hybridization probes to identify TRL-encoding nucleic acids (e.g., TRL mRNA) and fragments for use as PCR primers for the amplification or mutation of TRL nucleic acid molecules. As used herein, the term "nucleic acid molecule" is intended to include DNA molecules (e.g., cDNA or genomic DNA) and RNA molecules (e.g., MRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated TRL nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO: 1, SEQ ID NO:3, SEQ ID NO:22, the DNA insert of the plasmid deposited with ATCC as Accession Number 98649, or a portion of these nucleotide molecules, can be isolated using standard molecular biology techniques and the sequence information provided herein. Using all or portion of the nucleic acid sequences of SEQ ID NO: 1, SEQ ID NO:3, SEQ ID NO:22, or the DNA insert of the plasmid deposited with ATCC as Accession Number 98649 as a hybridization probe, TRL nucleic acid molecules can be isolated using standard hybridization and cloning techniques (e.g., as described in Sambrook, J., Fritsh, E. F., and Maniatis, T. Molecular Cloning: A Laboratory Manual. 2nd, ed, Cold Spring Harbor Laboratory, Cold Spring Harbor Laboratory Press, Cold Spring Harbor, N.Y., 1989),.

Moreover, a nucleic acid molecule encompassing all or a portion of SEQ ID NO: 1, SEQ ID NO:3, SEQ ID NO:22, or the DNA insert of the plasmid deposited with ATCC as Accession Number 98649 can be isolated by the polymerase chain reaction using synthetic oligonucleotide primers designed based upon the sequence of SEQ ID NO:1, SEQ ID NO:3, SEQ ID NO:22, or the DNA insert of the plasmid deposited with ATCC as Accession Nunber 98649. For example, a portion of SEQ ID NO:3 was isolated using oligonucleotide primers T75 pwzf and T75 pwzr, based upon the sequence of SEQ ID NO:3 as described in detail in EXAMPLE 5.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to TRL nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO: 1. The sequence of SEQ ID NO: 1 corresponds to the murine TRL cDNA. This cDNA comprises sequences encoding the murine TRL protein (i.e., "the coding region", from nucleotides 344 to 2062), as well as 5' untranslated sequences (nucleotides 1 to 343) and 3' untranslated sequences (nucleotides 2063to 3331). Alternatively, the nucleic acid molecule can comprise only the coding region of SEQ ID NO: 1 (e.g., nucleotides 344 to 2065).

In another preferred embodiment, an isolated nucleic acid molecule of the invention comprises the nucleotide sequence shown in SEQ ID NO:3. The sequence of SEQ ID NO:3 corresponds to the human TRL I cDNA. This cDNA comprises sequences encoding the human TRL I protein (i.e., "the coding region", from nucleotides 190 to 948), as well as 5' untranslated sequences (nucleotides 1 to 189) and 3' untranslated sequences (nucleotides 948 to 2612). Alternatively, the nucleic acid molecule can comprise only the coding region of SEQ ID NO:3 (e.g., nucleotides 190 to 948).

In another preferred embodiment, an isolated nucleic acid molecule of the invention comprises the nucleotide sequence shown in SEQ ID NO:22. The sequence of SEQ ID NO:22 corresponds to the human TRL II cDNA. This cDNA comprises sequences encoding the human TRL II protein (i.e., "the coding region", from nucleotides 510–2324), as well as 5' untranslated sequences (nucleotides 1 to 509) and 3' untranslated sequences (nucleotides 2325 to 2638). Alternatively, the nucleic acid molecule can comprise only the coding region of SEQ ID NO:22 (e.g., nucleotides 510 to 2324).

In another preferred embodiment, an isolated nucleic acid molecule of the invention comprises a nucleic acid molecule which is a complement of the nucleotide sequence shown in SEQ ID NO: 1, SEQ ID NO:3, SEQ ID NO:5, SEQ ID NO:6, the DNA insert of the plasmid deposited with ATCC as Accession Number 98649, or a portion of either of these nucleotide sequences. A nucleic acid molecule which is complementary to the nucleotide sequence shown in SEQ ID NO: 1, SEQ ID NO: 3, SEQ ID NO:5, SEQ ID NO:6, or the DNA insert of the plasmid deposited with ATCC as Accession Number 98649is one which is sufficiently complementary to the nucleotide sequence shown in SEQ ID NO:1, SEQ ID NO:3, SEQ ID NO:5, SEQ ID NO:6, the DNA insert of the plasmid deposited with ATCC as Accession Number 98649, such that it can hybridize to the nucleotide sequence shown in SEQ ID NO: 1, SEQ ID NO:3, SEQ ID NO:5, SEQ ID NO:6, the DNA insert of the plasmid deposited with ATCC as Accession Number 98649, thereby forming a stable duplex.

In still another preferred embodiment, an isolated nucleic acid molecule of the present invention comprises a nucleotide sequence which is at least about 60–65%, preferably at least about 70–75%, more preferable at least about 80–85%, and even more preferably at least about 90–95% or more homologous to the nucleotide sequence shown in SEQ ID NO: 1, the nucleotide sequence shown in SEQ ID NO:3, the nucleotide sequence shown in SEQ ID NO:5, the nucleotide sequence shown in SEQ ID NO:6, the nucleotide sequence of the DNA insert of the plasmid deposited with ATCC as Accession Number 98649, or a portion of any of these nucleotide sequences.

Moreover, the nucleic acid molecule of the invention can comprise only a portion of the nucleic acid sequence of SEQ ID NO: 1, SEQ ID NO:3, SEQ ID NO:22, or the DNA insert of the plasmid deposited with ATCC as Accession Number 98649, (or SEQ ID NO:5, SEQ ID NO:6, or SEQ ID NO:24) for example a fragment which can be used as a probe or primer or a fragment encoding a biologically active portion of TRL. The nucleotide sequence determined from the cloning of the murine and human TRL genes allows for the generation of probes and primers designed for use in identifying and/or cloning TRL homologues in other cell types, e.g. from other tissues, as well as TRL homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of SEQ ID NO: 1, SEQ ID NO:3, SEQ ID NO:22, or the DNA insert of the plasmid deposited with ATCC as Accession Number 98649 (or SEQ ID NO:5, SEQ ID NO:6, or SEQ ID NO:24) sense, of an anti-sense sequence of SEQ ID NO: 1, SEQ ID NO:3, SEQ ID NO:22, or the DNA insert of the plasmid deposited with ATCC as Accession Number 98649, or of a naturally occurring mutant of either SEQ ID NO: 1, SEQ ID NO:3, SEQ ID NO:22, or the DNA insert of the plasmid deposited with ATCC as Accession Number 98649.

Probes based on the either the murine or human TRL nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a TRL protein, such as by measuring a level of a TRL-encoding nucleic acid in a sample of cells from a subject e.g., detecting TRL rnRNA levels or determining whether a genomic TRL gene has been mutated or deleted.

A nucleic acid fragment encoding a "biologically active portion of TRL" can be prepared by isolating a portion of SEQ ID NO:1, SEQ ID NO:3, SEQ ID NO:5, or SEQ ID NO:6, which encodes a polypeptide having a TRL biological activity (the biological activities of the TRL proteins have previously been described), expressing the encoded portion of TRL protein (e.g., by recombinant expression in vitro) and assessing the activity of the encoded portion of TRL. For example, a nucleic acid fragment encoding a biologically active portion of murine TRL encompasses at least nucleic acids 365–490, 491–604, or 605–783 of SEQ ID NO: 1 (encoding a murine TRL CRD). Moreover, a nucleic acid fragment encoding a biologically active portion of murine TRL encompasses at least nucleic acids 1151–1207 of SEQ ID NO: 1 (encoding a TRL transmembrane domain). Alternatively, a nucleic acid fragment encoding a biologically active portion of human TRL encompasses at least nucleic acids 328–456, 457–582, 583–696, or 697–825 of SEQ ID NO:3 (encoding a human TRL CRD). Moreover, a nucleic acid fragment encoding a biologically active portion of human TRL encompasses at least nucleic acids 190–312 of SEQ ID NO:3 (encoding a TRL signal sequence). Alternatively, a nucleic acid fragment encoding a biologically active portion of human TRL II encompasses at least nucleic acids 648–776, 777–902, 903–1016, or 1017–1145 of SEQ ID NO:22 (encoding a human TRL II CRD). Moreover, a nucleic acid fragment encoding a biologically active portion of human TRL encompasses at least nucleic acids 510–632 of SEQ ID NO:3 (encoding a TRL signal sequence).

The invention further encompasses nucleic acid molecules that differ from the nucleotide sequence shown in SEQ ID NO:1, SEQ ID NO:3, SEQ ID NO:22, or the DNA insert of the plasmid deposited with ATCC as Accession Number 98649 (and portions thereof, e.g., SEQ ID NO:5, or SEQ ID NO:6) due to degeneracy of the genetic code and thus encode the same TRL protein as that encoded by the nucleotide sequence shown in SEQ ID NO: 1, SEQ ID NO:3, SEQ ID NO:22, or the DNA insert of the plasmid deposited with ATCC as Accession Number 98649. In another embodiment, an isolated nucleic acid molecule of the invention has a nucleotide sequence encoding a protein having an amino acid sequence shown in SEQ ID NO:2, SEQ ID NO:4, or SEQ ID NO:23.

In addition to the murine and human TRL nucleotide sequences shown in SEQ ID NO: 1,SEQ ID NO:3, and SEQ ID NO:22, it will be appreciated by those skilled in the art that DNA sequence polymorphisms that lead to changes in the amino acid sequences of TRL may exist within a population (e.g., the human population). Such genetic polymorphism in the TRL gene may exist among individuals within a population due to natural allelic variation. As used herein, the terms "gene" and "recombinant gene" refer to nucleic acid molecules comprising an open reading frame encoding a TRL protein, preferably a mammalian TRL protein. Such natural allelic variations can typically result in 1–5% variance in the nucleotide sequence of the TRL gene. Any and all such nucleotide variations and resulting amino acid polymorphisms in TRL that are the result of natural allelic variation and that do not alter the functional activity of TRL are intended to be within the scope of the invention.

Moreover, nucleic acid molecules encoding TRL proteins from other species, and thus which have a nucleotide sequence which differs from the murine and human sequences of SEQ ID NO:1, SEQ ID NO:3, or SEQ ID NO:22, are intended to be within the scope of the invention. Nucleic acid molecules corresponding to natural allelic variants and homologues of the TRL cDNAs of the invention can be isolated based on their homology to the murine or human TRL nucleic acids disclosed herein using the murine or human cDNAs, or a portion of either sequence, as a hybridization probe according to standard hybridization techniques under stringent hybridization conditions. For example, a soluble murine TRL cDNA can be isolated based on its homology to murine membrane-bound or human soluble TRL. Likewise, a membrane-bound human TRL cDNA can be isolated based on its homology to soluble human TRL or murine membrane bound TRL.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO: 1. In other embodiment, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2× SSC, 0.1% SDS at 50–65° C. Preferably, an isolated nucleic acid molecule of the invention that hybridizes under stringent conditions to the sequence of SEQ ID NO: I, SEQ ID NO:3, or SEQ IN NO:22 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the TRL sequence that may exist in the population, the skilled artisan will further appreciate that changes can be introduced by mutation into the nucleotide sequence of SEQ ID NO: 1, SEQ ID NO:3, or SEQ ID NO:2 thereby leading to changes in the amino acid sequence of the encoded TRL protein, without altering the functional ability of the TRL protein. For example, nucleotide substitutions leading to amino acid substitutions at "non-essential" amino acid residues can be made in the sequence of SEQ ID NO: I, SEQ ID NO:3, SEQ ID NO:22, or the DNA insert of the plasmid deposited with ATCC as Accession Number 98649. A "non-essential" amino acid residue is a residue that can be altered from the wild-type sequence of TRL (e.g., the sequence of SEQ ID NO:2, SEQ ID NO:4, or SEQ ID NO:23) without altering the biological activity, whereas an "essential" amino acid residue is required for biological activity. For example, amino acid residues of TRL that are conserved among the murine and human family members of this invention (as indicated by the alignment and comparison of the amino acid sequences of SEQ ID NOs:2 and 4 presented as FIGS. 3A–G or by the alignment and comparison of the amino acid sequences of SEQ ID NO:s 2, 4, and 23 presented as FIGS. 5A–G) are predicted to be essential in TRL and thus are not likely to be amenable to alteration. Furthermore, amino acid residues that are conserved among the TRL proteins of the present invention, as well as among the TNFR2, OPG, and CD40 protein families (as indicated by the alignment presented as FIG. 3) are predicted to be particularly unamenable to alteration (For example, all proteins of the TNFR2, OPG, and CD40 families, as well as the TRL proteins of the present invention, contain at least four cysteine residues among the CRR domains (the CRD domains for murine and human TRL have been previously described, the CRD domains of the TNFR2, OPG, and CD40 families are as follows: amino acids 39–76, 77–118, 119–162, and 163–201 of huTNFR2; amino acids 39–77, 78–119, 120–164, 165–203 of muTNFR2; amino acids 27–62,63–104, 105–147, and 148–186 of soluble TNFR2; amino acids 25–60, 61–103, 104–144, and 145–187 of huCD40R; amino acids 25–60, 61–103, 104–144, and 145–187 of muCD40R; and amino acids 22–64, 65–105, 106–142, and 143–194 of both huOPG and muOPG.

In addition, the amino acid sequence of human TRL I has two predicted N-glycosylation sites corresponding to amino acids 82–84 and 141–143 of SEQ ID NO:4 and the amino acid sequence of human TRL II amino acid sequence has 6 predicted N-glycosylation sites corresponding to amino acids 82–84, 141–143, 252–254, 257–259, 278–280, and 289–291. The human TRL II amino acid sequence further has three putative protein kinase C phosphorylation sites corresponding to amino acids Ser44 1, Thr467, and Thr506 and the murine TRL amino acid sequence has four putative protein kinase C phosphorylation sites corresponding to amino acids Ser291, Thr 294, Thr 385, and Thr 424 which are not likely to be amenable to alteration. Furthermore, the death domains of human TRL II and murine TRL have conserved amino acid residues as indicated in FIG. 6 which are not likely to be amenable to alteration.

Moreover, structure/function and crystallographic analyses of various members 5' of the TNFR superfamily have identified residues and/or regions that are important for the activity of these proteins. Thus, these highly conserved regions in TNFR superfamily proteins are not likely to be amenable to mutation. Other amino acid residues, however, (e.g., those that are not conserved or only semi-conserved among members of the TNFR superfamily) may not be essential for activity and thus are likely to be amenable to alteration.

Accordingly, another aspect of the invention pertains to nucleic acid molecules encoding TRL proteins that contain changes in amino acid residues that are not essential for activity. Such TRL proteins differ in amino acid sequence from SEQ ID NO:2, SEQ ID NO:4, or SEQ ID NO:23 yet retain biological activity. In one embodiment, the isolated nucleic acid molecule comprises a nucleotide sequence encoding a protein, wherein the protein comprises an amino acid sequence at least about 60% homologous to the amino acid sequence of SEQ ID NO:2, SEQ ID NO:4, or SEQ ID NO:23. Preferably, the protein encoded by the nucleic acid molecule is at least about 70% homologous to SEQ ID NO:2, SEQ ID NO:4, or SEQ ID NO:23, more preferably at least about 80% homologous to SEQ ID NO:2, SEQ ID NO:4, or SEQ ID NO:23, even more preferably at least about 90% homologous to SEQ ID NO:2, SEQ ID NO:4, or SEQ ID NO:23, and most preferably at least about 95% homologous to SEQ ID NO:2, SEQ ID NO:4, or SEQ ID NO:23.

An isolated nucleic acid molecule encoding a TRL protein homologous to the protein of SEQ ID NO:2, SEQ ID NO:4, or SEQ ID NO:23 can be created by introducing one or more nucleotide substitutions, additions or deletions into the nucleotide sequence of SEQ ID NO:1, SEQ ID NO:3, SEQ ID NO:22, or the DNA insert of the plasmid deposited with ATCC as Accession Number 98649 such that one or more amino acid substitutions, additions or deletions are introduced into the encoded protein. Mutations can be introduced into SEQ ID NO: 1, SEQ ID NO:3, SEQ ID NO:22, or the DNA insert of the plasmid deposited with ATCC as Accession Number 98649 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in TRL is preferably replaced with another amino acid residue from the same side chain family. Alternatively, in another embodiment, mutations can be introduced randomly along all or part of a TRL coding sequence, such as by saturation mutagenesis, and the resultant mutants can be screened for TRL biological activity activity to identify mutants that retain activity. Following mutagenesis of SEQ ID NO: 1, SEQ ID NO:3, SEQ ID NO:5, or SEQ ID NO:6, the encoded protein can be expressed recombinantly and the activity of the protein can be determined.

In a preferred embodiment, a mutant TRL protein can be assayed for (1) the ability to form protein:protein interactions with other TNFR superfamily proteins, other cell-surface proteins, or biologically active portions thereof; (2) complex formation between a mutant TRL protein and a TRL ligand; (3) the ability of a mutant TRL protein to bind to an intracellular target protein or biologically active portion thereof; (e.g. SH2 domain-containing proteins or cytoskeletal proteins). In yet another preferred embodiment, a mutant TRL can be assayed for the ability to (1) modulate cellular signal transduction; (2) regulate cellular proliferation; (3) regulate cellular differentiation; (4) regulate cell survival or apoptosis; and (5) modulate a cell involved in the immune response.

In addition to the nucleic acid molecules encoding TRL proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire TRL coding strand, or to only a portion thereof. In one embodiment, an antisense nucleic acid molecule is antisense to a "coding region" of the coding strand of a nucleotide sequence encoding TRL. The term "coding region" refers to the region of the nucleotide sequence comprising codons which are translated into amino acid residues (e.g., the coding region of murine TRL corresponds to SEQ ID NO:5 and the coding region of human TRL corresponds to SEQ ID NO:6). In another embodiment, the antisense nucleic acid molecule is antisense to a "noncoding region" of the coding strand of a nucleotide sequence encoding TRL. The term "noncoding region" refers to 5' and 3' sequences which flank the coding region that are not translated into amino acids (i.e., also referred to as 5' and 3' untranslated regions).

Given the coding strand sequences encoding TRL disclosed herein (e.g., SEQ ID NO:5, SEQ ID NO:6, or SEQ ID NO:24), antisense nucleic acids of the invention can be designed according to the rules of Watson and Crick base pairing. The antisense nucleic acid molecule can be complementary to the entire coding region of TRL mRNA, but more preferably is an oligonucleotide which is antisense to only a portion of the coding or noncoding region of TRL mRNA. For example, the antisense oligonucleotide can be complementary to the region surrounding the translation start site of TRL MRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a TRL protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol Ill promoter are preferred.

In yet another embodiment, the antisense nucleic acid molecule of the invention is an a-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) *Nucleic Acids Res.* 15:6131–6148) or a himeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave TRL MRNA transcripts to thereby inhibit translation of TRL mRNA. A ribozyme having specificity for a TRL-encoding nucleic acid can be designed based upon the nucleotide sequence of a TRL cDNA disclosed herein (i.e., SEQ ID NO: 1). For example, a derivative of a *Tetrahymena* L-19 IVS RNA can be constructed in which the nucleotide sequence of the active site is complementary to the nucleotide sequence to be cleaved in a TRL-encoding MRNA. See, e.g., Cech et al. U.S. Pat. No. 4,987,071; and Cech et al. U.S. Pat. No. 5,116,742. Alternatively, TRL mRNA can be used to select a catalytic RNA having a specific ribonuclease activity from a pool of RNA molecules. See, e.g., Bartel, D. and Szostak, J. W. (1993) *Science* 261:1411–1418.

Alternatively, TRL gene expression can be inhibited by targeting nucleotide sequences complementary to the regulatory region of the TRL (e.g., the TRL promoter and/or enhancers) to form triple helical structures that prevent transcription of the TRL gene in target cells. See generally, Helene, C. (1991) *Anticancer Drug Des.* 6(6):569–84; Helene, C. et al. (1992) *Ann. NY: Acad. Sci.* 660:27–36; and Maher, L.J. (1992) Bioassays 14(12):807–15.

In preferred embodiments, the nucleic acids of TRL can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. PNAS 93: 14670–675.

PNAs of TRL can be used therapeutic and diagnostic applications. For example, PNAs can be used as antisense or antigene agents for sequence-specific modulation of gene expression by, e.g., inducing trascription or translation arrest or inhibiting replication. PNAs of TRL can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) supra); or as probes or primers for DNA sequence and hybridization (Hyrup B. et al. (1996) supra; Perry-O'Keefe supra).

In another embodiment, PNAs of TRL can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of TRL can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Research* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxythymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric moleclues can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. W088/09810, published Dec. 15, 1988) or the blood-brain barrier (see, e.g., PCT Publication No. W089/10134, published Apr. 25, 1988). In addition, oligonucleotides can be modified with hybridization-triggered cleavage agents (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated TRL Proteins and Anti-TRL Antibodies

One aspect of the invention pertains to isolated TRL proteins, and biologically active portions thereof, as well as polypeptide fragments suitable for use as immunogens to raise anti-TRL antibodies. In one embodiment, native TRL proteins can be isolated from cells or tissue sources by an appropriate purification scheme using standard protein purification techniques. In another embodiment, TRL proteins are produced by recombinant DNA techniques. Alternative to recombinant expression, a TRL protein or polypeptide can be synthesized chemically using standard peptide synthesis techniques.

An "isolated" or "purified" protein or biologically active portion thereof is substantially free of cellular material or other contaminating proteins from the cell or tissue source from which the TRL protein is derived, or substantially free from chemical precursors or other chemicals when chemically synthesized. The language "substantially free of cellular material" includes preparations of TRL protein in which the protein is separated from cellular components of the cells from which it is isolated or recombinantly produced. In one embodiment, the language "substantially free of cellular material" includes preparations of TRL protein having less than about 30% (by dry weight) of non-TRL protein (also referred to herein as a "contaminating protein" ), more preferably less than about 20% of non-TRL protein, still more preferably less than about 10% of non-TRL protein, and most preferably less than about 5% non-TRL protein. When the TRL protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of TRL protein in which the protein is separated from chemical precusors or other chemicals which are involved in the synthesis of the protein. In one embodiment, the language "substantially free of chemical precursors or other chemicals" includes preparations of TRL protein having less than about 30% (by dry weight) of chemical precursors or non-TRL chemicals, more preferably less than about 20% chemical precursors or non-TRL chemicals, still more preferably less than about 10% chemical precursors or non-TRL chemicals, and most preferably less than about 5% chemical precursors or non-TRL chemicals.

Biologically active portions of a TRL protein include peptides comprising amino acid sequences sufficiently homologous to or derived from the amino acid sequence of the TRL protein, e.g., the amino acid sequence shown in SEQ ID NO:2, SEQ ID NO:4, or SEQ ID NO:23, which include less amino acids than the flill length TRL proteins, and exhibit at least one activity of a TRL protein. Typically, biologically active portions comprise a domain or motif with at least one activity of the TRL protein. A biologically active portion of a TRL protein can be a polypeptide which is, for example, 10, 25, 50, 100 or more amino acids in length.

In one embodiment, a biologically active portion of a TRL protein comprises at least one CRD characteristic of the TNFR superfamily of proteins. In another embodiment, a biologically active portion of a TRL protein comprises at least a transmembrane domain. In yet another embodiment, a biologically active portion of a TRL protein comprises at least a signal sequence.

In an alternative embodiment, a biologically active portion of a TRL protein comprises at least a C-terminal unique domain of a TRL protein. In another embodiment, a biologically active portion of a TRL protein comprises at least a C-terminal unique domain which contains a death domain. In another embodiment, a biologically active portion of a TRL protein comprises at least a death domain. In yet another embodiment, a biologically active portion of a TRL protein comprises the N-terminal portion of a TRL molecule containing at least one, preferably two, more preferably three and even more preferably four CRDs, but is missing a substantial portion of the TRL C-terminal unique domain. Such a preferred TRL molecule is referred to as a "TRL extracellular domain". For example, preferred TRL extracellular domains contain at least about amino acids 1–290, 1–270, 50–270, 88–270, or 131–270 of SEQ ID NO:2, at least about amino acids 1–212,48–212, 90–212, 131–212 of SEQ ID NO:4, or at least about 1–370, 1–351, 47–370, 90–370, 132–370, or 170–370.

It is to be understood that a preferred biologically active portion of a TRL protein of the present invention may contain at least one of the above-identified structural domains. A more preferred biologically active portion of a TRL protein may contain at least two of the above-identified structural domains. An even more preferred biologically active portion of a TRL protein may contain at least three of the above-identified structural domains. A particularly preferred biologically active portion of a TRL protein of the present invention may contain at least four of the above-identified structural domains. A more particularly preferred biologically active portion of a TRL protein may have at least five of the above-identified structural domains. Finally, a most preferred biologically active portion of a TRL protein may contain at least six of the above-identified structural domains.

Moreover, other biologically active portions, in which other regions of the protein are deleted, can be prepared by recombinant techniques and evaluated for one or more of the functional activities of a native TRL protein.

In a preferred embodiment, the TRL protein has an amino acid sequence shown in SEQ ID NO:2, SEQ ID NO:4, or SEQ ID NO:23. In other embodiments, the TRL protein is substantially homologous to SEQ ID NO:2, SEQ ID NO:4, or SEQ ID NO:23 and retains the finctional activity of the protein of SEQ ID NO:2, SEQ ID NO:4, or SEQ ID NO:23 yet differs in amino acid sequence due to natural allelic variation or mutagenesis, as described in detail in subsection 11 below. Accordingly, in another embodiment, the TRL protein is a protein which comprises an amino acid sequence at least about 60% homologous to the amino acid sequence of SEQ ID NO:2, SEQ ID NO:4, or SEQ ID NO:23 and retains the functional activity of the TRL proteins of SEQ ID NO:2, SEQ ID NO:4, or SEQ ID NO:23. Preferably, the protein is at least about 70% homologous to SEQ ID NO:2, SEQ ID NO:4, or SEQ ID NO:23, more preferably at least about 80% homologous to SEQ ID NO:2, SEQ ID NO:4, or SEQ ID NO:23, even more preferably at least about 90% homologous to SEQ ID NO 2 or SEQ ID NO:4, and most preferably at least about 95% or more homologous to SEQ ID NO:2, SEQ ID NO:4, or SEQ ID NO:23.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the TRL amino acid sequence of SEQ ID NO:2 having 573 amino acid residues, at least 172, preferably at least 229, more preferably at least 287, even more preferably at least 344, and even more preferably at least 401, 458 or 516 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity" ). The percent homology between the two sequences is a function of the number of identical positions shared by the sequences (i.e., % homology=# of identical positions/total # of positions×100).

The comparison of sequences and determination of percent homology between two sequences can be accomplished using a mathematical algorithim. A preferred, non-limiting example of a mathematical algorithim utilized for the comparison of sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. BLAST nucleotide searches can be performed with the NBLAST program, score=100, wordlength=12 to obtain nucleotide sequences homologous to TRL nucleic acid molecules of the invention. BLAST protein searches can be performed with the XBLAST program, score=50, wordlength=3 to obtain amino acid sequences homologous to TRL protein molecules of the invention. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the ALIGN algorithm of Myers and Miller, CABIOS (1989). When utilizing the ALIGN program for comparing amino acid sequences, a PAM120 weight residue table, a gap length penalty of 12, and a gap penalty of 4 can be used.

The invention also provides TRL chimeric or fusion proteins. As used herein, a TRL "chimeric protein" or "fusion protein" comprises a TRL polypeptide operatively linked to a non-TRL polypeptide. A "TRL polypeptide" refers to a polypeptide having an amino acid sequence corresponding to TRL, whereas a "non-TRL polypeptide" refers to a polypeptide having an amino acid sequence corresponding to a protein which is not substantially homologous to the TRL protein, e.g., a protein which is different from the TRL protein and which is derived from the same or a different organism. Within a TRL fusion protein the TRL polypeptide can correspond to all or a portion of a TRL protein. In a preferred embodiment, a TRL fusion protein comprises at least one biologically active portion of a TRL protein. In another preferred embodiment, a TRL fusion protein comprises at least two biologically active portions of a TRL protein. In another preferred embodiment, a TRL fusion protein comprises at least three biologically active portions of a TRL protein. Within the fusion protein, the term "operatively linked" is intended to indicate that the TRL polypeptide and the non-TRL polypeptide are fused in-frame to each other. The non-TRL polypeptide can be fused to the N-terminus or C-terminus of the TRL polypeptide.

For example, in one embodiment a TRL fusion protein comprises the extracellular domain of a TRL protein operably linked to the intercellular portion of a second protein known to be involved in cellular signaling. In another embodiment, a TRL fusion protein comprises a TRL C-terminal unique domain opreably linked to the extracellular domain of a second protein known to be involved in cellular signaling. Such fusion proteins can be further utilized in screening assays for compounds which modulate TRL activity (such assays are described in detail below).

In yet another embodiment, the fusion protein is a GST-TRL fusion protein in which the TRL sequences are fused to the C-terminus of the GST sequences. Such fusion proteins can facilitate the purification of recombinant TRL.

In another embodiment, the fusion protein is a TRL protein containing a heterologous signal sequence at its N-terminus. For example, the native TRL signal sequence (i.e, about amino acids 1 to 41 of SEQ ID NO:4) can be removed and replaced with a signal sequence from another protein. In certain host cells (e.g., mammalian host cells), expression and/or secretion of TRL can be increased through use of a heterologous signal sequence.

In yet another embodiment, the fusion protein is a TRL-immunoglobulin fusion protein in which the TRL sequences comprising primarily the TNFR-like CRD are fused to sequences derived from a member of the immunoglobulin protein family. Soluble derivatives have also been made of cell surface glycoproteins in the immunoglobulin gene superfamily consisting of an extracellular domain of the cell surface glycoprotein fused to an immunoglobulin constant (Fc) region (see e.g., Capon, D. J. et al. (1989) *Nature* 337:525–531 and Capon U.S. Pat. No. 5,116,964 and 5,428,130 [CD4-IgGl constructs]; Linsley, P.S. et al. (1991) J. Exp. Med. 173:721–730 [a CD28-IgGl construct and a B7–1-IgGI construct]; and Linsley, P. S. et al. (1991) *J. Exp. Med* 174:561–569 and U.S. Pat. No. 5,434,131[a CTLA4-IgGl]). Such fusion proteins have proven useful for modulating receptor-ligand interactions. Soluble derivatives of cell surface proteins of the TNFR superfamily proteins have been made consisting of an extracellular domain of the cell surface receptor fused to an immunoglobulin constant (Fc) region (See for example Moreland et al. (1997) N. Engl. J. Med. 337(3):141–147; van der Poll et al. (1997) Blood 89(10):3727–3734; and Ammnann et al. (1997) J. Clin. Invest. 99(7):1699–1703.)

The TRL-immunoglobulin fusion proteins of the invention can be incorporated into pharmaceutical compositions and administered to a subject to inhibit an interaction between a TRL ligand and a TRL protein on the surface of a cell, to thereby suppress TRL-mediated signal transduction in vivo. The TRL-immunoglobulin fusion proteins can be used to affect the bioavailability of a TRL cognate ligand. Inhibition of the TRL ligand/TRL interaction may be useful therapeutically for both the treatment of proliferative and differentiative disorders, as well as modulating (e.g. promoting or inhibiting) cell survival. Moreover, the TRL-immunoglobulin fusion proteins of the invention can be used as immunogens to produce anti-TRL antibodies in a subject, to purify TRL ligands and in screening assays to identify molecules which inhibit the interaction of TRL with a TRL ligand.

Preferably, a TRL chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology,* eds. Ausubel et al. John Wiley & Sons: 1992). Moreover, many expression vectors are commercially available that already encode a fusion moiety (e.g., a GST polypeptide). A TRL-encoding nucleic acid can be cloned into such an expression vector such that the fusion moiety is linked in-frame to the TRL protein.

The present invention also pertains to variants of the TRL proteins which function as either TRL agonists (mimetics) or as TRL antagonists. Variants of the TRL protein can be generated by mutagenesis, e.g., discrete point mutation or truncation of the TRL protein. An agonist of the TRL protein can retain substantially the same, or a subset, of the biological activities of the naturally occurring form of the TRL protein.

An antagonist of the TRL protein can inhibit one or more of the activities of the naturally occurring form of the TRL protein by, for example, competitively binding to a downstream or upstream member of a cellular signaling cascade which includes the TRL protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the TRL proteins.

In one, variants of the TRL protein which function as either TRL agonists (mimetics) or as TRL antagonists can be identified by screening combinatorial libraries of mutants, e.g., truncation mutants, of the TRL protein for TRL protein agonist or antagonist activity. In one embodiment, a variegated library of TRL variants is generated by combinatorial mutagenesis at the nucleic acid level and is encoded by a variegated gene library. A variegated library of TRL variants can be produced by, for example, enzymatically ligating a mixture of synthetic oligonucleotides into gene sequences such that a degenerate set of potential TRL sequences is expressible as individual polypeptides, or alternatively, as a set of larger fusion proteins (e.g., for phage display) containing the set of TRL sequences therein. There are a variety of methods which can be used to produce libraries of potential TRL variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential TRL sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the TRL protein coding sequence can be used to generate a variegated population of TRL fragments for screening and subsequent selection of variants of a TRL protein. In one embodiment, a library of coding sequence fragments can be generated by treating a double stranded PCR fragment of a TRL coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the TRL protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of TRL proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify TRL variants (Arkin and Yourvan (1992) *PNAS* 89:7811–7815; Delgrave et al. (1993) *Protein Engineering* 6(3):327–331).

In one embodiment, cell based assays can be exploited to analyze a variegated TRL library. For example, a library of expression vectors can be transfected into a cell line which ordinarily responds to a particular cytokine in a TRL-dependent manner. The transfected cells are then contacted with the cytokine and the effect of expression of the mutant on signaling by the cytokine can be detected, e.g. by measuring NF-κB activity or cell survival. Plasmid DNA can then be recovered from the cells which score for inhibition, or alternatively, potentiation of cytokine induction, and the individual clones further characterized.

An isolated TRL protein, or a portion or fragment thereof, can be used as an immunogen to generate antibodies that bind TRL using standard techniques for olyclonal and monoclonal antibody preparation. The full-length TRL protein can be sed or, alternatively, the invention provides antigenic peptide fragments of TRL for use as immunogens. The antigenic peptide of TRL comprises at least 8 amino acid residues of the amino acid sequence shown in SEQ ID NO:2, SEQ ID NO:4, or SEQ ID NO:23 and encompasses an epitope of TRL such that an antibody raised against the peptide forms a specific immune complex with TRL. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of TRL that are located on the surface of the protein, e.g., hydrophilic regions. A hydrophobicity analysis of the murine TRL protein sequence indicates 3 hydrophilic regions that are preferred for use as antigenic peptides:

amino acid residues 10–35, amino acid residues 70–95, and amino acid residues 190–220 of SEQ ID NO: 2. A hydrophobicity analysis of the human TRL I protein sequence indicates 3 hydrophilic regions that are preferred for use as antigenic peptides: amino acid residues 91–112, amino acid residues 51–75, and amino acid residues 224–250 of SEQ ID NO: 4.

A TRL immunogen typically is used to prepare antibodies by immunizing a suitable subject, (e.g., rabbit, goat, mouse or other mammal) with the immunogen. An appropriate immunogenic preparation can contain, for example, recombinantly expressed TRL protein or a chemically synthesized TRL polypeptide. The preparation can further include an adjuvant, such as Freund's complete or incomplete adjuvant, or similar immunostimulatory agent. Immunization of a suitable subject with an immunogenic TRL preparation induces a polyclonal anti-TRL antibody response.

Accordingly, another aspect of the invention pertains to anti-TRL antibodies. The term "antibody" as used herein refers to immunoglobulin molecules and immunologically active portions of immunoglobulin molecules, i.e., molecules that contain an antigen binding site which specifically binds (immunoreacts with) an antigen, such as TRL. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind TRL. The term "monoclonal antibody" or "monoclonal antibody composition", as used herein, refers to a population of antibody molecules that contain only one species of an antigen binding site capable of immunoreacting with a particular epitope of TRL. A monoclonal antibody composition thus typically displays a single binding affinity for a particular TRL protein with which it immunoreacts.

Polyclonal anti-TRL antibodies can be prepared as described above by immunizing a suitable subject with a TRL immunogen. The anti-TRL antibody titer in the immunized subject can be monitored over time by standard techniques, such as with an enzyme linked immunosorbent assay (ELISA) using immobilized TRL. If desired, the antibody molecules directed against TRL can be isolated from the mammal (e.g., from the blood) and further purified by well known techniques, such as protein A chromatography to obtain the IgG fraction. At an appropriate time after immunization, e.g., when the anti-TRL antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* .255:4980–83; Yeh et al. (1976) *PNAS* 76:2927–3 1; and Yeh et al. (1 982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy,* Alan R. Liss, Inc., pp. 77–96) or trioma techniques. The technology for producing monoclonal antibody hybridomas is well known (see generally R. H. Kenneth, in Monoclonal Antibodies: A New Dimension In Biological Analyses, Plenum Publishing Corp., New York, New York (1980); E. A. Lerner (1981) Yale J. Biol. Med., 54:387–402; M. L. Gefter et al. (1977) Somatic Cell Genet. 3:231–36). Briefly, an immortal cell line (typically a myeloma) is fused to lymphocytes (typically splenocytes) from a mammal immunized with a TRL immunogen as described above, and the culture supernatants of the resulting hybridoma cells are screened to identify a hybridoma producing a monoclonal antibody that binds TRL.

Any of the many well known protocols used for fusing lymphocytes and immortalized cell lines can be applied for the purpose of generating an anti-TRL monoclonal antibody (see, e.g., G. Galfre et al. (1977) *Nature* 266:55052; Gefter et al. *Somatic Cell Genet.,* cited supra; Lemer, *Yale J. Biol. Med.,* cited supra; Kenneth, *Monoclonal Antibodies,* cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium" ). Any of a number of myeloma cell lines can be used as a fusion partner according to standard techniques, e.g., the P3-NSI/1-Ag4–1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG" ). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind TRL, e.g., using a standard ELISA assay.

Alternative to preparing monoclonal antibody-secreting hybridomas, a monoclonal anti-TRL antibody can be identified and isolated by screening a recombinant combinatorial immunoglobulin library (e.g., an antibody phage display library) with TRL to thereby isolate immunoglobulin library members that bind TRL. Kits for generating and screening phage display libraries are commercially available (e.g., the Pharmacia *Recombinant Phage Antibody System,* Catalog No. 27-9400-01; and the Stratagene SurfZAP™Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clarkson et al. (1991) *Nature* 352:624–628; Gram et al. (1992) PNAS 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-TRL antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041 –1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) Science 229:1202–1207; Oi et al. (1986) BioTechniques 4:214; Winter U.S. Pat. No. 5,225,539; Jones et al. (1986) Nature 321:552–525; Verhoeyan et al. (1988) Science 239:1534; and Beidler et al. (1988) J Immunol. 141:40534060.

An anti-TRL antibody (e.g., monoclonal antibody) can be used to isolate TRL by standard techniques, such as affinity chromatography or immunoprecipitation. An anti-TRL antibody can facilitate the purification of natural TRL from cells and of recombinantly produced TRL expressed in host cells. Moreover, an anti-TRL antibody can be used to detect TRL protein (e.g., in a cellular lysate or cell supernatant) in order to evaluate the abundance and pattern of expression of the TRL protein. Anti-TRL antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding TRL (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are are referred to herein as "expression vectors" . In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., TRL proteins, mutant forms of TRL, fusion proteins, etc.).

The recombinant expression vectors of the invention can be designed for expression of TRL in prokaryotic or eukaryotic cells. For example, TRL can be expressed in bacterial cells such as E. coli, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fuision moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

In a preferred embodiment, exemplified in Example 5, the coding sequence of human TRL (i.e., encompassing amino acids 1 to 253) is cloned into a pCD5 expression vector to create a vector encoding a TRL-Ig fusion protein. In an alternative preferred embodiment, also exemplified in Example 5, the coding sequence of a form of human TRL lacking the signal sequence (i.e., encompassing amino acids 42 to 253) is cloned into a pPicZ expression vector (InVitrogen) downstream and in frame with a yeast-derived signal sequence. In yet another preferred embodiment, also exemplified in Example 5, the coding sequence of human TRL (i.e., encompassing amino acids 1 to 253) is cloned into a retroviral expression vector, pWZLBlastEC. The fusion proteins can be purified utilizing methods well known in the art of protein purification. Purified fusion proteins can be utilized in TRL activity assays, in TRL ligand binding (e.g. direct assays or competitive assays described in detail below), to generate antibodies specific for TRL proteins, as examples. In a preferred embodiment, a TRL fusion expressed in a retroviral expression vector of the present invention can be utilized to infect bone marrow cells which are subsequently transplanted into irradiated recipients. The pathology of the subject recipient is then examined after sufficient time has passed (e.g six (6) weeks).

Examples of suitable inducible non-fusion *E. coli* expression vectors include pTrc (Amann et al., (1988) *Gene* 69:301–315) and pET 1 ld (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET ld vector relies on transcription from a T7 gn10-lac fusion promoter mediated by a coexpressed viral RNA polymerase (T7 gn1). This viral polymerase is supplied by host strains BL21 (DE3) or HMS 1 74(DE3) from a resident X prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the TRL expression vector is a yeast expression vector. Examples of vectors for expression in yeast *S. cerivisae* include pYepSec 1 (Baldari, et al., (1987) *Embo J.* 6:229–234), pMFa (Kuijan and Herskowitz, (1982) *Cell* 30:93314 943), pJRY88 (Schultz et al., (1987) *Gene* 54:113–123), pYES2 (Invitrogen Corporation, San Diego, CA), and picZ (InVitrogen Corp, San Diego, Calif.).

Alternatively, TRL can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the a-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to TRL mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics,* Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, TRL protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding TRL or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) TRL protein. Accordingly, the invention further provides methods for producing TRL protein using the host cells of the invention. In one embodiment, the method comprises culturing the host cell of invention (into which a recombinant expression vector encoding TRL has been introduced) in a suitable medium such that TRL protein is produced. In another embodiment, the method further comprises isolating TRL from the medium or the host cell.

The host cells of the invention can also be used to produce nonhuman transgenic animals. For example, in one embodiment, a host cell of the invention is a fertilized oocyte or an embryonic stem cell into which TRL-coding sequences have been introduced. Such host cells can then be used to create non-human transgenic animals in which exogenous TRL sequences have been introduced into their genome or homologous recombinant animals in which endogenous TRL sequences have been altered. Such animals are useful for studying the function and/or activity of TRL and for identifying and/or evaluating modulators of TRL activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a manmnal, more preferably a mouse, in which an endogenous TRL gene has been altered by homologous recombination between the endogenous gene and an exogenous DNA molecule introduced into a cell of the animal, e.g., an embryonic cell of the animal, prior to development of the animal.

A transgenic animal of the invention can be created by introducing TRL-encoding nucleic acid into the male pronuclei of a fertilized oocyte, e.g., by microinjection, retroviral infection, and allowing the oocyte to develop in a pseudopregnant female foster animal. The human TRL cDNA sequence of SEQ ID NO: 1, SEQ ID NO:22, or the DNA insert of the plasmid deposited with ATCC as Accession Number 98649 can be introduced as a transgene into the genome of a non-human animal. Alternatively, a nonhuman homologue of the human TRL gene, such as the mouse TRL gene can be used as a transgene. Intronic sequences and polyadenylation signals can also be included in the transgene to increase the efficiency of expression of the transgene. A tissue-specific regulatory sequence(s) can be operably linked to the TRL transgene to direct expression of TRL protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the TRL transgene in its genome and/or expression of TRL mRNA in tissues or cells of the animals. A transgenic founder animal can then be used to breed additional animals carrying the transgene. Moreover, transgenic animals carrying a transgene encoding TRL can further be bred to other transgenic animals carrying other transgenes.

To create a homologous recombinant animal, a vector is prepared which contains at least a portion of a TRL gene into which a deletion, addition or substitution has been introduced to thereby alter, e.g., finctionally disrupt, the TRL gene. The TRL gene can be a human gene (e.g., the cDNA of SEQ ID NO:3 or SEQ ID NO:22), but more preferably, is a non-human homologue of a human TRL gene. For example, a mouse TRL gene of SEQ ID NO: 1 can be used to construct a homologous recombination vector suitable for altering an endogenous TRL gene in the mouse genome. In a preferred embodiment, the vector is designed such that, upon homologous recombination, the endogenous TRL gene is finctionally disrupted (i.e., no longer encodes a functional protein; also referred to as a "knock out" vector). Alternatively, the vector can be designed such that, upon homologous recombination, the endogenous TRL gene is mutated or otherwise altered but still encodes functional protein (e.g., the upstream regulatory region can be altered to thereby alter the expression of the endogenous TRL protein). In the homologous recombination vector, the altered portion of the TRL gene is flanked at its 5' and 3' ends by additional nucleic acid of the TRL gene to allow for homologous recombination to occur between the exogenous TRL gene carried by the vector and an endogenous TRL gene in an embryonic stem cell. The additional flanking TRL nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced TRL gene has homologously recombined with the endogenous TRL gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach,* E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinion in Biotechnology 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/l7oxP recombinase system, see, e.g., Lakso et al. (1992) *PNAS* 89:6232–6236. Another example of a recombinase system is the FLP recombinase system of Saccharomyces cerevisiae (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813. In brief, a cell, e.g., a somatic cell, from the transgenic animal can be isolated and induced to to exit the growth cycle and enter Go phase. The quiescent cell can then be fused, e.g., through the use of electrical pulses, to an enucleated oocyte from an animal of the same species from which the quiescent cell is isolated. The recontructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The TRL nucleic acid molecules, TRL proteins, and anti-TRL antibodies (also referred to herein as "active compounds" ) of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifingal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradernal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, NJ) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a TRL protein or anti-TRL antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and filsidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a TRL protein of the invention has the following activities: (i) formation of a homogeneous multimeric signaling complex with like TRL proteins; (ii) formation of a heterogeneous multimeric signaling complex with other TNFR superfamily proteins or other cell-surface proteins; (iii) complex formation between a membrane-bound TRL protein and a cytokine; (iv) complex formation between a soluble TRL protein and a cognate ligand; (v) interaction of a TRL protein with an intracellular protein having substantial homology to the TNFR-associated proteins; (vi) interaction of a TRL protein with a TNFR-associated protein; and (vii) interaction of a TRL protein with other cellular proteins including cytoplasmic proteins (e.g. SH2 domain-containing proteins or a second death domain-containing protein) or cytoskeletal proteins and can thus be used to (i) modulate cellular signal transduction; (ii) regulate cellular proliferation; (iii) regulate cellular differentiation; (iv) regulate cell survival or apoptosis; or (v) modulate a cell involved in the immune response., either in vitro or in vivo. The isolated nucleic acid molecules of the invention can be used to express TRL protein (e.g., via a recombinant expression vector in a host cell in gene therapy applications), to detect TRL MRNA (e.g., in a biological sample) or a genetic lesion in a TRL gene, and to modulate TRL activity, as described further below. In addition, the TRL proteins can be used to screen drugs or compounds which modulate the TRL activity as well as to treat disorders characterized by insufficient or excessive production of TRL protein or production of TRL protein forms which have decreased or abherrent activity compared to TRL wild type protein (e.g. proliferative disorders such as cancer or inflammatory diseases such as arthritis). Moreover, soluble forms of the TRL protein can be used to bind ligands of membrane-bound TRL and influence bioavailability. In addition, the anti-TRL antibodies of the invention can be used to detect and isolate TRL proteins and modulate TRL activity.

A. Screening Assays:

The invention provides a method (also referred to herein as a "screening assay" ) for identifying modulators, i.e., candidate or test compounds or agents (e.g., peptides, peptidomimetics, small molecules or other drugs) which bind to TRL proteins or have a stimulatory or inhibitory effect on, for example, TRL expression or TRL activity.

In one embodiment, the invention provides assays for screening candidate or test compounds which bind to or modulate the activity of the membrane-bound form of a TRL protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med Chem.* 37:2678; Cho et al. (1993) *Science* 261:1303; Carrell et al. (1994)*Angew. Chem. Int. Ed. Engl.* 33:2059; Carell et al. (1994) *Angew. Chem. Int. Ed. Engl.* 33:2061; and in Gallop et al. (1994) *J. Med Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad Sci.* 87:6378–6382); (Felici (1991) *J. Mol. Biol.* 222:301–310); (Ladner supra.).

In one embodiment, an assay is a cell-based assay in which a cell which expresses a membrane-bound form of TRL protein, or a biologically active portion thereof, on the cell surface is contacted with a test compound and the ability of the test compound to bind to a TRL protein determined. The cell, for example, can of mammalian origin or a yeast cell. Determining the ability of the test compound to bind to the TRL protein can be accomplished, for example, by coupling the test compound with a radioisotope or enzymatic label such that binding of the test compound to the TRL protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., TRL ligand) to interact with a TRL protein without the labeling of any of the interactants. For example, a microphysiometer can be used to detect the interaction of a compound with its cognate receptor without the labeling of either the compound or the receptor. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, the assay comprises contacting a cell which expresses a membrane-bound form of TRL protein, or a biologically active portion thereof, on the cell surface with a known compound which binds TRL to form an assay mixture, contacting the assay mixture with a test compound, and determining the ability of the test compound to interact with a TRL protein, wherein determining the ability of the test compound to interact with a TRL protein comprises determining the ability of the test compound to preferentially bind to TRL or a biologically active portion thereof as compared to the known compound.

In another embodiment, an assay is a cell-based assay comprising contacting a cell expressing a membrane-bound form of TRL protein, or a biologically active portion thereof, on the cell surface with a test compound and determining the ability of the test compound to modulate (e.g. stimulate or inhibit) the activity of the TRL protein or biologically active portion thereof. Determining the ability of the test compound to modulate the activity of TRL or a biologically active portion thereof can be accomplished, for example, by determining the ability of the TRL protein to bind to or interact with a TRL target molecule. As used herein, a "target molecule" is a molecule with which a TRL protein binds or interacts in nature, for example, a molecule on the surface of a cell which expresses a TRL protein, a molecule on the surface of a second cell, a molecule in the extracellular milieu, a molecule associated with the internal surface of a cell membrane or a cytoplasmic molecule. A TRL target molecule can be a non-TRL molecule or a TRL protein or polypeptide of the present invention. In one embodiment, a TRL target molecule is a component of a signal transduction pathway which facilitates transduction of an extracellular signal (e.g. a signal generated by binding of a compound to a membrane-bound TRL molecule) through the cell membrane and into the cell. The target, for example, can be a second intercellular protein which has catalytic activity or a protein which facilitates the association of downstream signaling molecules with TRL. Alternatively, the target molecule can be a substrate for a catalytic activity of the TRL protein.

Determining the ability of the TRL protein to bind to or interact with a TRL target molecule can be accomplished by one of the methods described above for determining direct binding. In a preferred embodiment, determining the ability of the TRL protein to bind to or interact with a TRL target molecule can be accomplished by determining the activity of the target molecule. For example, the activity of the target molecule can be determined by detecting induction of a cellular second messenger of the target (i.e. intracellular $Ca^{2+}$, diacylglycerol, $1P_3$, etc.), detecting catalytic/enzymatic activity of the target an appropriate substrate, detecting the induction of a reporter gene (comprising a TRL-responsive regulatory element operatively linked to a nucleic acid encoding a detectable marker, e.g. luciferase), or detecting a cellular response, for example, cell survival, cellular differentiation, or cell proliferation.

In yet another embodiment, an assay of the present invention is a cell-free assay comprising contacting a TRL protein or biologically active portion thereof with a test compound and determining the ability of the test compound to bind to the TRL protein or biologically active portion thereof. Binding of the test compound to the TRL protein can be determined either directly or indirectly as described above. In a preferred embodiment, the assay comprises contacting the TRL protein or biologically active portion thereof with a known compound which binds TRL to form an assay mixture, contacting the assay mixture with a test compound, and determining the ability of the test compound to interact with a TRL protein, wherein determining the ability of the test compound to interact with a TRL protein comprises determining the ability of the test compound to preferentially bind to TRL or biologically active portion thereof as compared to the known compound.

In another embodiment, an assay is a cell-free assay comprising contacting TRL protein or biologically active portion thereof with a test compound and determining the ability of the test compound to modulate (e.g. stimulate or inhibit) the activity of the TRL protein or biologically active portion thereof. Determining the ability of the test compound to modulate the activity of TRL can be accomplished, for example, by determining the ability of the TRL protein to bind to a TRL target molecule by one of the methods described above for determining direct binding. Determining the ability of the TRL protein to bind to a TRL target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of TRL can be accomplished by determining the ability of the TRL protein further modulate a TRL target molecule. For example, the catalytic/enzymatic activity of the target molecule on an appropriate substrate can be determined as previously described.

In yet another embodiment, the cell-free assay comprises contacting the TRL protein or biologically active portion thereof with a known compound which binds TRL to form an assay mixture, contacting the assay mixture with a test compound, and determining the ability of the test compound to interact with a TRL protein, wherein determining the ability of the test compound to interact with a TRL protein comprises determining the ability of the TRL protein to preferentially bind to or modulate the activity of a TRL target molecule.

The cell-free assays of the present invention are amenable to use of both the soluble form or the membrane-bound form of TRL. In the case of cell-free assays comprising the membrane-bound form of TRL, it may be desirable to utilize a solubilizing such that the membrane-bound form of TRL is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]- 1-propane sulfonate (CHAPS), 3-[(3-cholamidopropyl)dimethylamminio]-2-hydroxy-1-propane sulfonate (CHAPSO), or N-dodecyl=N, N-dimethyl-3-ammonio-1-propane sulfonate.

In more than one embodiment of the above assay methods of the present invention, it may be desirable to immobilize either TRL or its target molecule to facilitate separation of complexed from uncomplexed forms of one or both of the proteins, as well as to accommodate automation of the assay. Binding of a test compound to TRL, or interaction of TRL with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/ TRL fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or TRL protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of TRL binding or activity determined using standard techniques.

Other techniques for immobilizing proteins on matrices can also be used in the screening assays of the invention. For example, either TRL or its target molecule can be immobilized utilizing conjugation of biotin and streptavidin. Biotinylated TRL or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with TRL or target molecules but which do not interfere with binding of the TRL protein to its target molecule can be derivatized to the wells of the plate, and unbound target or TRL trapped in the wells by antibody conjugation. Methods for detecting such complexes, in addition to those described above for the GST-immobilized complexes, include immunodetection of complexes using antibodies reactive with the TRL or target molecule, as well as enzyme-linked assays which rely on detecting an enzymatic activity associated with the TRL or target molecule.

In another embodiment, modulators of TRL expression are identified in a method wherein a cell is contacted with a candidate compound and the expression of TRL mRNA or protein in the cell is determined. The level of expression of TRL MRNA or protein in the presence of the candidate compound is compared to the level of expression of TRL mRNA or protein in the absence of the candidate compound. The candidate compound can then be identified as a modulator of TRL expression based on this comparison. For example, when expression of TRL mRNA or protein is greater (statistically significantly greater) in the presence of the candidate compound than in its absence, the candidate compound is identified as a stimulator of TRL mRNA or protein expression. Alternatively, when expression of TRL MRNA or protein is less (statistically significantly less) in the presence of the candidate compound than in its absence, the candidate compound is identified as an inhibitor of TRL mRNA or protein expression. The level of TRL mRNA or protein expression in the cells can be determined by methods described herein for detecting TRL mRNA or protein.

In yet another aspect of the invention, the TRL proteins can be used as "bait proteins" in a two-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; lwabuchi et al. (1993) *Oncogene* 8:1693–1696; and Brent WO94/10300), to identify other proteins, which bind to or interact with TRL ("TRL-binding proteins" or "TRL-bp" ) and modulate TRL activity. Such TRL-binding proteins are also likely to be involved in the propagation of signals by the TRL proteins as, for example, upstream or downstream elements of the TRL pathway.

The two-hybrid system is based on the modular nature of most transcription factors, which consist of separable DNA-binding and activation domains. Briefly, the assay utilizes two different DNA constructs. In one construct, the gene that codes for TRL is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a TRL-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with TRL.

This invention further pertains to novel agents identified by the above-described screening assays. Accordingly, it is within the scope of this invention to further use an agent identified as described herein in an appropriate animal model. For example, an agent identified as described herein (e.g., a TRL modulating agent, an antisense TRL nucleic acid molecule, a TRL-specific antibody, or a TRL-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the TRL nucleotide sequences, described herein, can be used to map the location of the TRL genes on a chromosome. The mapping of the TRL sequences to chromosomes is an important first step in correlating these sequences with genes associated with disease.

Briefly, TRL genes can be mapped to chromosomes by preparing PCR primers (preferably 15–25 bp in length) from the TRL nucleotide sequences. Computer analysis of the TRL sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the TRL sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the TRL nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *PNAS,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the TRL gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The TRL sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the TRL nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The TRL nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO: 1, can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from TRL nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial TRL Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO: 1, SEQ ID NO:3, or SEQ ID NO:22 are particularly appropriate for this use as greater numbers of polymorphisms occur in the noncoding regions, making it easier to differentiate individuals using this technique. Examples of polynucleotide reagents include the TRL nucleotide sequences or portions thereof, e.g., fragments derived from the noncoding regions of SEQ ID NO: 1, SEQ ID NO:3, or SEQ ID NO:22, having a length of at least bases, preferably at least 30 bases.

The TRL nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such TRL probes can be used to identify tissue by species and/or by organ type.

In a similar fashion, these reagents, e.g., TRL primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trails are used for prognostic (predictive) purposes to thereby treat an individual prophylactically. Accordingly, one aspect of the present invention relates to diagnostic assays for determining TRL protein and/or nucleic acid expression as well as TRL activity, in the context of a biological sample (e.g., blood, serum, cells, tissue) to thereby determine whether an individual is afflicted with a disease or disorder, or is at risk of developing a disorder, associated with aberrant TRL expression or activity. The invention also provides for prognostic (or predictive) assays for determining whether an individual is at risk of developing a disorder associated with TRL protein, nucleic acid expression or activity. For example, mutations in a TRL gene can be assayed in a biological sample. Such assays can be used for prognostic or predictive purpose to thereby phophylactically treat an individual prior to the onset of a disorder characterized by or associated with TRL protein, nucleic acid expression or activity.

Another aspect of the invention pertains to monitoring the influence of agents (e.g., drugs, compounds) on the expression or activity of TRL in clinical trials.

These and other agents are described in further detail in the following sections.

1. Diagnostic Assays:

An exemplary method for detecting the presence or absence of TRL protein or nucleic acid in a biological sample involves obtaining a biological sample from a test subject and contacting the biological sample with a compound or an agent capable of detecting TRL protein or nucleic acid (e.g., mRNA, genomic DNA) that encodes TRL protein such that the presence of TRL is detected in the biological sample. A preferred agent for detecting TRL MRNA or genomic DNA is a labeled nucleic acid probe capable of hybridizing to TRL MRNA or genomic DNA. The nucleic acid probe can be, for example, the full-length TRL cDNA of SEQ ID NO: 1 or SEQ ID NO:3, or a portion thereof, such as an oligonucleotide of at least 15, 30, 50, 100, 250 or 500 nucleotides in length and sufficient to specifically hybridize under stringent conditions to TRL mRNA or genomic DNA. Other suitable probes for use in the diagnostic assays of the invention are described herein.

A preferred agent for detecting TRL protein is a labeled antibody capable of binding to TRL protein. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect TRL mRNA or protein in a biological sample in vitro as well as in vivo. For example, in vitro techniques for detection of TRL MRNA include Northern hybridizations and in situ hybridizations. In vitro techniques for detection of TRL protein include enzyme linked immunosorbent assays (ELISAs), Western blots, immunoprecipitations and immunofluorescence. In vitro techniques for detection of TRL genomic DNA include Southern hybridizations. Furthermore, in vivo techniques for detection of TRL protein include introducing into the subject a labeled anti-TRL antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a tissue sample isolated by conventional means from a subject.

In another embodiment, the methods further involve obtaining a control biological sample from a control subject, contacting the control sample with a compound or agent capable of detecting TRL protein, mRNA, or genomic DNA, such that the presence of TRL protein, mRNA or genomic DNA is detected in the biological sample, and comparing the presence of TRL protein, mRNA or genomic DNA in the control sample with the presence of TRL protein, MRNA or genomic DNA in the test sample.

The invention also encompasses kits for detecting the presence of TRL in a biological sample. For example, the kit can comprise a labeled compound or agent capable of detecting TRL protein or mRNA in a biological sample; means for determining the amount of TRL in the sample; and means for comparing the amount of TRL in the sample with a standard. The compound or agent can be packaged in a suitable container. The kit can flirther comprise instructions for using the kit to detect TRL MRNA or protein.

2. Prognostic Assays

The diagnostic methods described herein can furthermore be utilized to identify subjects having or at risk of developing a disease or disorder associated with aberrant TRL expression or activity. For example, the assays described herein, such as the preceding diagnostic assays or the following assays, can be utilized to identify a subject having or at risk of developing a disorder associated with TRL protein, nucleic acid expression or activity such as cancer. Alternatively, the prognostic assays can be utilized to identify a subject having or at risk for developing cancer. Thus, the present invention provides a method for identifying a disease or disorder associated with aberrant TRL expression or activity in which a test sample is obtained from a subject and TRL protein or nucleic acid (e.g, rnRNA, genomic DNA) is detected, wherein the presence of TRL protein or nucleic acid is diagnostic for a subject having or at risk of developing a disease or disorder associated with aberrant TRL expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant TRL expression or activity. For example, such methods can be used to determine whether a subject can be effectively treated with an agent for cancer. Thus, the present invention provides methods for determining whether a subject can be effectively treated with an agent for a disorder associated with aberrant TRL expression or activity in which a test sample is obtained and TRL protein or nucleic acid expression or activity is detected (e.g., wherein the abundance of TRL protein or nucleic acid expression or activity is diagnostic for a subject that can be administered the agent to treat a disorder associated with aberrant TRL expression or activity.)

The methods of the invention can also be used to detect genetic alterations in a TRL gene, thereby determining if a subject with the altered gene is at risk for a disorder characterized by aberrant cell proliferation and/or differentiation. In preferred embodiments, the methods include detecting, in a sample of cells from the subject, the presence or absence of a genetic alteration characterized by at least one of an alteration affecting the integrity of a gene encoding a TRL-protein, or the mis-expression of the TRL gene. For example, such genetic alterations can be detected by ascertaining the existence of at least one of I) a deletion of one or more nucleotides from a TRL gene; 2) an addition of one or more nucleotides to a TRL gene; 3) a substitution of one or more nucleotides of a TRL gene, 4) a chromosomal rearrangement of a TRL gene; 5) an alteration in the level of a messenger RNA transcript of a TRL gene, 6) aberrant modification of a TRL gene, such as of the methylation pattern of the genomic DNA, 7) the presence of a non-wild type splicing pattern of a messenger RNA transcript of a TRL gene, 8) a non-wild type level of a TRL-protein, 9) allelic loss of a TRL gene, and 10) inappropriate post-translational modification of a TRL-protein. As described herein, there are a large number of assay techniques known in the art which can be used for detecting alterations in a TRL gene. A preferred biological sample is a tissue or serum sample isolated by conventional means from a subject.

In certain embodiments, detection of the alteration involves the use of a probe/primer in a polymerase chain reaction (PCR) (see, e.g. U.S. Pat. No. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the TRL-gene (see Abravaya et al. (1995) *Nucleic Acids Res* .23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a TRL gene under conditions such that hybridization and amplification of the TRL-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a TRL gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in TRL can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in TRL can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the TRL gene and detect mutations by comparing the sequence of the sample TRL with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the TRL gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type TRL sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in TRL cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a TRL sequence, e.g., a wild-type TRL sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in TRL genes. For example, single strand conformation polymorphism (SSCP) may be used to detect differences in electrophoretic mobility between mutant and wild type nucleic acids (Orita et al. (1989) *Proc Natl. Acad Sci USA:* 86:2766, see also Cotton (1993) *Mutat Res* 285:125–144; and Hayashi (1992) Genet Anal Tech Appi 9:73–79). Single-stranded DNA fragments of sample and control TRL nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) *Proc. Natl Acad Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natil. Acad Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a TRL gene.

Furthermore, any cell type or tissue in which TRL is expressed may be utilized in the prognostic assays described herein.

3. Monitorinp of Effects During Clinical Trials

Monitoring the influence of agents (e.g., drugs, compounds) on the expression or activity of a TRL protein (e.g., modulation of an inflammatory response) an be applied not only in basic drug screening, but also in clinical trials. For example, the effectiveness of an agent determined by a screening assay as described herein to increase TRL gene expression, protein levels, or upregulate TRL activity, can be monitored in clinical trails of subjects exhibiting decreased TRL gene expression, protein levels, or downregulated TRL activity. Alternatively, the effectiveness of an agent determined by a screening assay to decrease TRL gene expression, protein levels, or downregulate TRL activity, can be monitored in clinical trails of subjects exhibiting increased TRL gene expression, protein levels, or upregulated TRL activity. In such clinical trials, the expression or activity of a TRL gene, and preferably, other genes that have been implicated in, for example, a proliferative disorder can be used as a "read out" or markers of the phenotype of a particular cell.

For example, and not by way of limitation, genes, including TRL, that are modulated in cells by treatment with an agent (e.g., compound, drug or small molecule) which modulates TRL activity (e.g., identified in a screening assay as described herein) can be identified. Thus, to study the effect of agents on proliferative disorders, for example, in a clinical trial, cells can be isolated and RNA prepared and analyzed for the levels of expression of TRL and other genes implicated in the proliferative disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of TRL or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a TRL protein, mRNA, or genomic DNA in the preadministration sample; (iii) obtaining one or more post-administration samples from the subject; (iv) detecting the level of expression or activity of the TRL protein, mRNA, or genomic DNA in the post-administration samples; (v) comparing the level of expression or activity of the TRL protein, MRNA, or genomic DNA in the pre-administration sample with the TRL protein, mRNA, or genomic DNA in the post administration sample or samples; and (vi) altering the administration of the agent to the subject accordingly. For example, increased administration of the agent may be desirable to increase the expression or activity of TRL to higher levels than detected, i.e., to increase the effectiveness of the agent. Alternatively, decreased administration of the agent may be desirable to decrease expression or activity of TRL to lower levels than detected, i.e. to decrease the effectiveness of the agent. According to such an embodiment, TRL expression or activity may be used as an indicator of the effectiveness of an agent, even in the absence of an observable phenotypic response.

C. Methods of Treatment

The present invention provides for both prophylactic and therapeutic methods of treating a subject at risk of (or susceptible to) a disorder or having a disorder associated with aberrant TRL expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the TRL molecules of the present invention or TRL modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant TRL expression or activity, by administering to the subject a TRL or an agent which modulates TRL expression or at least one TRL activity. Subjects at risk for a disease which is caused or contributed to by aberrant TRL expression or activity can be identified by, for example, any or a combination of diagnostic or prognostic assays as described herein. Administration of a prophylactic agent can occur prior to the manifestation of symptoms characteristic of the TRL aberrancy, such that a disease or disorder is prevented or, alternatively, delayed in its progression. Depending on the type of TRL aberrancy, for example, a TRL, TRL agonist or TRL antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating TRL expression or activity for therapeutic purposes. Accordingly, in an exemplary embodiment, the modulatory method of the invention involves contacting a cell with a TRL or agent that modulates one or more of the activities of TRL protein activity associated with the cell. An agent that modulates TRL protein activity can be an agent as described herein, such as a nucleic acid or a protein, a naturally-occurring target molecule of a TRL protein (e.g., a naturally-occurring cognate ligand of a TRL protein), a TRL antibody, a TRL agonist or antagonist, a peptidomimetic of a TRL agonist or antagonist, or other small molecule. In one embodiment, the agent stimulates one or more TRL protein activity. Examples of such stimulatory agents include active TRL protein and a nucleic acid molecule encoding TRL that has been introduced into the cell. In another embodiment, the agent inhibits one or more TRL protein activity. Examples of such inhibitory agents include antisense TRL nucleic acid molecules and anti-TRL antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a TRL protein or nucleic acid molecule. In one embodiment, the method involves administering an agent (e.g., an agent identified by a screening assay described herein), or combination of agents that modulates (e.g., upregulates or downregulates) TRL expression or activity. In another embodiment, the method involves administering a TRL protein or nucleic acid molecule as therapy to compensate for reduced or aberrant TRL expression or activity.

Stimulation of TRL activity is desirable in situations in which TRL is abnormally downregulated and/or in which increased TRL activity is likely to have a beneficial effect. One example of such a situation is where a subject has a disorder characterized by abherrent cell proliferation (e.g. cancer). Another example of such a situation is where the subject has a inflammaroty disease (e.g. arthritis).

3. Pharmacozenomics

The TRL molecules of the present invention, as well as agents, or modulators which have a stimulatory or inhibitory effect on TRL activity (e.g., TRL gene expression) as identified by a screening assay described herein can be administered to individuals to treat (prophylactically or therapeutically) disorders (e.g, prostrate cancer) ssociated with aberrant TRL activity. In conjunction with such treatment, harmacogenomics (i.e., the study of the relationship between an individual's genotype nd that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a TRL molecule or TRL modulator as well as tailoring the dosage and/or therapeutic regimen of treatment with a TRL molecule or TRL modulator.

Pharmacogenomics deals with clinically significant hereditary variations in the response to drugs due to altered drug disposition and abnormal action in affected persons. See e.g., Eichelbaum, M., *Clin Exp Pharmacol Physiol,* 1996, 23(10–11) :983–985 and Linder, M. W., *Clin Chem,* 1997, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitroflirans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a TRL protein or TRL receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2CI9 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a TRL molecule or TRL modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a TRL molecule or TRL modulator, such as a modulator identified by one of the exemplary screening assays described herein.

This invention is fuirther illustrated by the following examples which should not be construed as limiting. The contents of all references, patents and published patent applications cited throughout this application are incorporated herein by reference.

EXAMPLES

Example 1: Isolation And Charactejrization of Murine And Human TRL cDNAs

In this example, the isolation and characterization of the genes encoding murine and human TRL (also referred to as "TANGO 75") is described.

Isolation of the murine TRL cDNA

Poly A+RNA from primary murine megakaryocyte cells was used to construct a cDNA library. The CDNA library was constructed by first and second strand synthesis as recommended by the manufacturer for the Gibco BRL kit SuperScript Plasmid System for cDNA Synthesis and Plasmid Cloning (Gibco/BRL; Bethesda Md.). cDNAs were ligated into the pMET vector and subject to hightroughput random sequencing using automated fluorescent dideoxynucleotide sequencing and dye primer chemistry (Applied Biosystems Inc., Foster City Calif.).

Isolation of the human TRL cDNA

The human gene was found through homology with the murine gene. A GenBank™ search of the dbEST database utilizing a mouse megakaryocyte partial TRL cDNA (corresponding to the first 402 nucleotides of SEQ ID NO: 1) revealed a human cDNA clone with between 80–89% nucleotide identity to the murine partial cDNA. This 452bp EST (homosapien clone 280262 3' /EST N49208) represents a reversed clone and was not annotated. BlastX searching (BLAST™ searching utilizing a nucleotide sequence against a protein database) using this sequence revealed no proteins having obvious homology. The homosapien clone 280262 was purchased from Research Genetics (Huntsville, AL) as part of the IMAGE Consortium. Both the human and mouse clone were fully sequenced (SEQ ID NO:l and SEQ ID NO:3) and represent alternate splice forms of the same gene.

A GenBank™ search using the human TRL I nucleotide sequence of SEQ ID NO:3 revealed EST N49208, which is 452 nucleotides in length, is 97% identical to nucleotides 23–452 of the human TRL I nucleotide sequence depicted in FIGS. 2A–C and SEQ ID NO:3. The reverse complement of EST N50261, which is 438 nucleotides in length, is 99% identical to nucleotides 2161–2598 of the human TRL I nucleotide sequence which corresponds to the 3' untranslated region of the gene.

A GenBankTM search using the murine TRL nucleotide sequence of SEQ ID NO: 1 revealed eight EST sequences, four human AA351536, D59902, AA35723 1, and AA374471) and four mouse (AA239755, AA271351, AA072902, and R74815) which were similar to different regions of the nucleotide sequence of SEQ ID NO: 1. The EST sequences having greater than 80% identity are listed in Table 1 as well as the nucleotides of SEQ ID NO: 1 to which each EST sequence corresponds. As no reading frame can be determined from an EST (such as the an EST identified in the above database searches), an amino acid sequence encoded by the EST cannot be determined.

Example 2: Distribution Of TRL mRNA In Mouse And Human Tissues

An ~1.2 kb EcoRI/XhoI fragment from human TRL (that corresponds to the open reading frame) was used as a probe for Northern blots. The fragment was labeled using the Prime It kit from Stratagene (La Jolla, Calif.) and then hybridized to multi-tissue northern blots from Clontech (Palo Alto, Calif.) as recommended by the manufacturer. In human an approximate 4.2 kb transcript was detected in most tissues but was more prominently expressed in kidney, brain, placenta and colon. In mouse, a 4.2 kb transcript was also found in most tissues and was most prominently expressed in kidney and brain.

Example 3: Chromosomal Mapping Of The Murine And Human TRL Genes

This Example describes the chromosomal mapping of the human and murine TRL genes.

Chromosomal Mapping of the human TRL Gene

Oligos used:

T75F2

5' - tccctgacaacacaagctca (SEQ ID NO: 14)

T75R3

5' - tccatttctcccggttctg (SEQ ID NO: 15)

A number of oligonucleotide primers were designed unique to the human 3' UTR, which allowed mapping using the Stanford Human Genome Center's G3 radiation hybrid panel, and the Whitehead Institute/MIT Center for Genome Research's GENEBRIDGE 4 radiation hybrid panel (Research Genetics, Huntsville, Ala.). These maps were built with STSs, ESTs, polymorphic markers and genes. The approximate location of the human TRL gene was determined to be on Chromosome 6p25 by Stanford panel. The LOD score from the Whitehead panel was not as good as the Stanford panel.

An aliquot of DNA (10ul) from the radiation hybrid panels was amplified for 30 cycles on an MJ Research thermocycler in a 20ul reaction containing: 500ng primers, 2.5U Taq (Perkin Elmer) and final buffer concentrations of 0.2mM dNTPs, 1.5mM $MgCl_2$. (PCR Program: Step 1 95° C. 2min., Step 2 95° C. 1 min., Step 3 60° C. 1 min., Step 4 72° C. 1 min., Goto Step 2 a 29 times, 4° C. indefinite.) PCR products were analyzed by electrophoresis through 1.5% agarose gels.

Chromosomal Mapping of the murine TRL Gene

The TRL gene was mapped utilizing the Mus spretus/C57BL/6J backcross. T75 is located 12cM distal of Dl 7MIT48 and 20cM proximal of D I7MIT9. This region is syntenic to 6p21 in human. PCR primers were used to amplify mouse genomic DNA using standard techniques. Primers were designed from noncoding sequences of murine T75 and were as follows:

Forward Primer:

5" CCATGTTGACCGTACCAC3' (SEQ ID NO: 16)

Reverse Primer:

5' GCACTCTCGGTCAGTCAA3' (SEQ IDNO:17)

Amplification conditions were 35 cycles at 95° C. for 40 seconds, 55° C. for 50 seconds and 72° C. for 50 seconds. Samples were run on denaturing 10% SSCP gel at 3W and 4° C. for 16 hours.

Example 4: Characterization Of TRL Proteins

In this example, the predicted amino acid sequnces of the murine and human TRL proteins were compared to amino acid sequences of known proteins and various motifs were identified. In addition, the hydrophobicity of the murine and human TRL proteins were predicted.

The murine TRL cDNA encodes a protein of 573 amino acids (predicted MW of 63kDa, not including post-translational modifications), with a predicted transmembrane sequence (aa270–288). The human TRL cDNA encodes a 253 amino acid protein with a predicted molecular weight of 27kDa (not including post-translational modifications). A signal peptide is predicted to exist from aa 141, using the prediction program SIGNALP (Henrik Nielsen, Jacob Engelbrecht, Soren Brunak and Gunnar von Heijne "Identification of prokaryotic and eukaryotic signal peptides and prediction of their cleavage sites." (1997) Protein Engineering 10, 1–6). The human TRL I protein appears to be secreted and there is no evidence of a transmembrane domain.

Alignment of the murine and human TRL proteins using GAP alignment tool of the GCG package (Genetic Computer Group, Madison, Wisc.) reveals that the two proteins are 81% identical (86% similarity) over the amino acids encoding the cysteine-rich domains (mouse aa 1–171; human aa 83–253). At the nucleotide level the two cDNA's are 64.5% identical, although there are two regions of high homology (approx 870%) corresponding to nucleotides 191–842 in mouse (nt 283–934 in human) and nucleotides 890–1602 (nt 942–1654 in human).

It is an tic ipated that both splice forms (soluble and m embrane bound) of the protein are present in human and mouse. Both proteins contain the cysteine patterning characteristic to members of the TNFR family.

Example 5: Preparation Of TRL Protein.

Recombinant TRL was produced in Pichiapastoris. A form lacking the signal sequence (aa 42–253) was cloned into pPicZ (Invitrogen, San Diego, Calif.) in frame with a yeast signal sequence using the following primers;

t75Rl5p; 5' TTTT GAATTCCAGCCAGAACAGAAGG CCTCGA3' (SEQ ID NO:18) and t75xba3p; 5' TTTTTCTAGATACCTTTGGTCTTTGG-GAAC3' (SEQID NO:19)

Transformation, expression and purification of the recombinant protein was then performed essentially as described by the manufacturer (Invitrogen, San Diego, Calif.).

In another example the full op en read ing frame (ORF) of human TRL I (aa 1 -253) was expressed as an Fc fusion in pCD5.

A further example is the over-production of full length human TRL in vivo mediated by retroviral infection. The sequence for human TRL (aa 1–253) was amplified using the following primers;

T75pwzf; 5' AAAAAAGAATTCGCCGCCATGGGGAC-CTCT 3' (SEQ ID NO:20) and

T75pwzr; 5° CTTGTCGTCGTCGTCCTTGTAGTCGTAC-CTTTG 3' (SEQ ID NO:2 1)

The reverse primer places an epitope tag (Flag sequence) on the 3, end of the protein. Amplified products were then subdloned into the retroviral pWZLB last vector, and sequence verified. Bone marrow infected with the retrovirus is then transplanted into irradiated mouse recipients and pathology reviewed after 6 weeks.

Example 6: Isolation of Human TRIL 11 CDNA and Characterization of Corresponding Protein A human Hela cell cDNA library was screened as described in Maniatis, T. *Molecular Cloning: A Laboratory Manual.* 2nd, ed, Cold Spring Harbor Laboratory, Cold Spring Har bor Laboratory Press, Cold Spring Harbor, N.Y. (1989) for alternate splice forms of TRL with a 1.3 kb fragment encompassing the 5' end of the mouse TRL cDNA. A 2.6 kb cDNA clone was isolated and fuilly sequenced and the nucleotide sequence is set forth in SEQ ID NO:22. This clone encodes a protein of 605 amino acids with a predicted molecular weight of 66.2 kDa, including signal peptide and without posttranslational modifications. The signal peptide is encoded by amino acids 1–41 of human TRL II (SEQ ID NO:23) and a putatitive transmembrane domain exists between amino acids 352 and 370. In the extracellular region of the molecule there are 6 potential N-linked glycosylation sites centered at amino acids 82, 141, 252, 257, 278 and 289. A putative death-domain exists (PROSITE: PDOC50017) in the intracellular region of the molecule at about amino acids 415–498. There are 3 potential protein kinase C phosphorylation sites at amino acids 441, 467 and 506.

Example 7: Apopotic Effect of TRL II Protein.

To ascertain if the clone containing full-length human TRL II could induce apoptotic signal, an over-expression model similar to that described by Kumar et al (1994) was used. Briefly the SW480 colorectal carcinoma cell line was plated into 6-well tissue culture plates at a density of $4 \times 10^5$ cells/well. The next day cells were transfected with the reporter gene pSVO (Clontech) and test construct (human TRL II) or control construct (pMET), using lipofectamine (GIBCO). 36 hours post-transfection the cells were fixed and stained for β-gal activity and the percentage of cells expressing B-gal ascertained. The percentage of β-gal positive staining cells in control plates was approximately 18.8% whereas in plates transfected with human TRL II, only 9.1% of cells that were β-gal positive. This decrease is statistically significant. Additional experiments indicate that overexpression of TRL II is capable of inducing cell death in SW480 cells.

Equivalents Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule comprising a nucleotide sequence which encodes a polypeptide comprising an amino acid sequence having at least 90% identity to a TNF receptor-like (TRL) amino acid sequence selected from the group consisting of: SEQ ID NO:2, SEQ ID NO: 23, SEQ ID NO: 23 without amino acids 1 to 41; and an amino acid sequence encoded by the cDNA insert of the plasmid deposited with ATCC as Accession Number 98649, wherein the percent identity is over the entire length of the amino acid sequences when aligned for comparison purposes.

2. The nucleic acid molecule of claim 1, which encodes an amino acid sequence which comprises a death domain.

3. The nucleic acid molecule of claim 2, wherein the death domain comprises amino acid residues 333 to 416 of SEQ ID NO:2 or amino acid residues 415 to 498 of SEQ ID NO:23.

4. An isolated nucleic acid molecule comprising a nucleotide sequence which encodes a polypeptide comprising the amino acid sequence of SEQ ID NO:2.

5. An isolated nucleic acid molecule comprising a nucleotide sequence which encodes a polypeptide comprising the amino acid sequence of SEQ ID NO:23.

6. An isolated nucleic acid molecule comprising a nucleotide sequence which encodes a polypeptide comprising the amino acid sequence of SEQ ID NO:23 without amino acids 1 to 41.

7. An isolated nucleic acid molecule comprising a nucleotide sequence which encodes a mature polypeptide encoded by the cDNA insert of the plasmid deposited with ATCC as Accession Number 98649.

8. An isolated nucleic acid molecule comprising a nucleotide sequence encoding a polypeptide consisting of the amino acid sequence selected from the group consisting of the amino acid sequence of SEQ ID NO:2, SEQ ID NO: 23, SEQ ID NO: 23 without amino acid residues 1 to 41, and an amino acid sequence encoded by the cDNA insert of the plasmid deposited with ATCC as Accession Number 98649.

9. An isolated nucleic acid molecule comprising a nucleotide sequence having at least 90% [identical] identity to a nucleotide sequence selected from the group consisting of SEQ ID NO:5 and SEQ ID NO: 24, wherein the percent identity is over the entire length of the nucleotide sequences when aligned for comparison purposes.

10. An isolated nucleic acid molecule comprising the nucleotide sequence of SEQ ID NO: 1.

11. An isolated nucleic acid molecule comprising the nucleotide sequence of SEQ ID NO:5.

12. An isolated nucleic acid molecule comprising the nucleotide sequence of SEQ ID NO:22.

13. An isolated nucleic acid molecule comprising the nucleotide sequence of SEQ ID NO: 24.

14. An isolated nucleic acid molecule comprising the nucleotide sequence of the cDNA insert of the plasmid deposited with ATCC as Accession Number 98649.

15. An isolated nucleic acid molecule consisting of the nucleotide sequence selected from the group consisting of SEQ ID NO: 1, SEQ ID NO:5, SEQ ID NO: 22, SEQ ID NO: 24, and the nucleotide sequence of the cDNA insert of the plasmid deposited with ATCC as Accession Number 98649.

16. The nucleic acid molecule as in any one of claims 1 to 15, further comprising nucleic acid sequences which are heterologous to the nucleic acid molecule as in any one of claims 1 to 15.

17. A vector comprising the nucleic acid molecule as in any one of claims 1 to 15.

18. A vector comprising the nucleic acid molecule of claim 16.

19. The vector of claim 17, which includes nucleic acid sequences which regulate expression of a polypeptide encoded by the nucleic acid molecule.

20. The vector of claim 18, which includes nucleic acid sequences which regulate expression of a polypeptide encoded by the nucleic acid molecule.

21. A host cell comprising the vector of claim 17.

22. A host cell comprising the vector of claim 18.

23. A host cell comprising the nucleic acid molecule as in any one of claims 1 to 15.

24. The host cell of claim 21 which is a mammalian host cell.

25. The host cell of claim 22 which is a mammalian host cell.

26. The host cell of claim 23 which is a mammalian host cell.

27. A method for producing a polypeptide comprising culturing the host cell of claim 21 under conditions in which the nucleic acid molecule is expressed.

28. A method for producing a polypeptide comprising culturing the host cell of claim 22 under conditions in which the nucleic acid molecule is expressed.

29. A method for detecting the presence of a nucleic acid molecule of claim 1 in a sample comprising:

a) contacting the sample with a nucleic acid probe or primer which hybridizes to the nucleic acid molecule under hybridization conditions of 6× sodium chloride/sodium citrate (SSC) at 45° C., followed by washing in 0.2× SSC 0.1% SDS at 50° C.; and b) determining whether the nucleic acid probe or primer binds to the nucleic acid molecule in the sample to thereby detect the presence of the nucleic acid molecule in the sample.

30. The method of claim 29 wherein the sample comprises mRNA molecules and is contacted with a nucleic acid probe.

31. A kit comprising a nucleic acid probe or primer which hybridizes to a nucleic acid molecule of claim 1 under hybridization conditions of 6× sodium chloride/sodium citrate (SSC) at 45° C. followed by washing in 0.2× SSC, 0.1% SDS at 50° C. and instructions for use.

* * * * *